US012673209B2

(12) United States Patent
Mishra

(10) Patent No.: US 12,673,209 B2
(45) Date of Patent: Jul. 7, 2026

(54) APPARATUS FOR DELIVERING ENHANCED STIMULATION WAVEFORMS

(71) Applicant: Nalu Medical, Inc., Carlsbad, CA (US)

(72) Inventor: Lakshmi Narayan Mishra, Carlsbad, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 310 days.

(21) Appl. No.: 18/314,624

(22) Filed: May 9, 2023

(65) Prior Publication Data

US 2024/0139517 A1 May 2, 2024

Related U.S. Application Data

(63) Continuation of application No. PCT/US2021/058673, filed on Nov. 9, 2021.

(60) Provisional application No. 63/218,159, filed on Jul. 2, 2021, provisional application No. 63/112,055, filed on Nov. 10, 2020.

(51) Int. Cl.
*A61N 1/36* (2006.01)

(52) U.S. Cl.
CPC ..... *A61N 1/36139* (2013.01); *A61N 1/36178* (2013.01)

(58) Field of Classification Search
CPC ............ A61N 1/36139; A61N 1/36178; A61N 1/36071; A61N 1/365; A61N 1/37241; A61N 1/371
See application file for complete search history.

(56) References Cited

U.S. PATENT DOCUMENTS

| 3,835,833 | A | 9/1974 | Limoge |
| 3,902,501 | A | 9/1975 | Citron et al. |
| 3,939,843 | A | 2/1976 | Smyth et al. |
| | | (Continued) | |

FOREIGN PATENT DOCUMENTS

| AU | 2014233252 A1 | 11/2015 |
| EP | 1609501 A1 | 12/2005 |
| | (Continued) | |

OTHER PUBLICATIONS

Buhlmann, J. et al., "Modeling of a segmented electrode for desynchronizing deep brain stimulation" Frontiers in Neuroengineering (2011) vol. 4, Article 15, pp. 1-8.

(Continued)

*Primary Examiner* — Paula J Stice
(74) *Attorney, Agent, or Firm* — Nelson Mullins Riley & Scarborough LLP

(57) ABSTRACT

An apparatus for delivering stimulation energy to a patient is provided. The apparatus comprises an algorithm for determining a stimulation paradigm comprising one or more stimulation parameter settings, and an implantable system comprising an implantable device. The implantable device comprises at least one sensor for measuring evoked compound action potentials (eCAPs), muscle responses, and/or other neural responses, and multiple stimulation elements configured to deliver the stimulation energy to tissue based on the stimulation paradigm. The algorithm is configured to determine the stimulation paradigm based on the measured neural responses. Methods of delivering stimulation energy are also provided.

24 Claims, 11 Drawing Sheets

(56) References Cited

U.S. PATENT DOCUMENTS

| 4,033,357 A | 7/1977 | Helland et al. |
| 4,071,033 A | 1/1978 | Nawracaj et al. |
| 4,140,133 A | 2/1979 | Kastrubin et al. |
| 4,236,529 A | 12/1980 | Little |
| 4,262,678 A | 4/1981 | Stokes |
| 4,269,198 A | 5/1981 | Stokes |
| 4,301,815 A | 11/1981 | Doring |
| 4,324,251 A | 4/1982 | Mann |
| 4,407,303 A | 10/1983 | Akerstroem |
| 4,409,994 A | 10/1983 | Doring |
| 4,411,276 A | 10/1983 | Dickhudt et al. |
| 4,469,104 A | 9/1984 | Peers-Trevarton |
| 4,506,679 A | 3/1985 | Mann |
| 4,578,598 A | 3/1986 | Faulhaber |
| 4,582,069 A | 4/1986 | McArthur |
| 4,592,356 A | 6/1986 | Gutierrez |
| 4,627,438 A | 12/1986 | Liss et al. |
| 4,658,835 A | 4/1987 | Pohndorf |
| 4,716,888 A | 1/1988 | Wesner |
| 4,721,118 A | 1/1988 | Harris |
| 4,735,204 A | 4/1988 | Sussman et al. |
| 4,796,643 A | 1/1989 | Nakazawa et al. |
| 4,841,971 A | 6/1989 | Hess |
| 4,883,070 A | 11/1989 | Hanson |
| 4,898,173 A | 2/1990 | Daglow et al. |
| 4,922,908 A | 5/1990 | Morawetz et al. |
| 4,945,922 A | 8/1990 | Van Krieken |
| 4,957,118 A | 9/1990 | Erlebacher |
| 5,031,618 A | 7/1991 | Mullett |
| 5,131,389 A | 7/1992 | Giordani |
| 5,143,067 A | 9/1992 | Rise et al. |
| 5,193,539 A | 3/1993 | Schulman et al. |
| 5,201,312 A | 4/1993 | Schenck et al. |
| 5,257,634 A | 11/1993 | Kroll |
| 5,282,845 A | 2/1994 | Bush et al. |
| 5,300,107 A | 4/1994 | Stokes et al. |
| 5,395,328 A | 3/1995 | Ockuly et al. |
| 5,540,736 A | 7/1996 | Haimovich et al. |
| 5,545,206 A | 8/1996 | Carson |
| 5,662,697 A | 9/1997 | Li et al. |
| 5,735,887 A | 4/1998 | Barreras, Sr. et al. |
| 5,814,089 A | 9/1998 | Stokes et al. |
| 5,833,603 A | 11/1998 | Kovacs et al. |
| 5,868,741 A | 2/1999 | Chia et al. |
| 5,908,433 A | 6/1999 | Eager et al. |
| 5,957,965 A | 9/1999 | Moumane et al. |
| 6,021,354 A | 2/2000 | Warman et al. |
| 6,058,331 A | 5/2000 | King |
| 6,169,925 B1 | 1/2001 | Villaseca et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,275,737 B1 | 8/2001 | Mann |
| 6,304,786 B1 | 10/2001 | Heil, Jr. et al. |
| 6,324,434 B2 | 11/2001 | Coe et al. |
| 6,405,091 B1 | 6/2002 | Vachon et al. |
| 6,482,152 B2 | 11/2002 | Kim |
| 6,510,347 B2 | 1/2003 | Borkan |
| 6,516,227 B1 | 2/2003 | Meadows et al. |
| 6,522,926 B1 | 2/2003 | Kieval et al. |
| 6,561,975 B1 | 5/2003 | Pool et al. |
| 6,884,122 B2 | 4/2005 | Robinson et al. |
| 6,895,280 B2 | 5/2005 | Meadows et al. |
| 6,904,322 B2 | 6/2005 | Katsnelson |
| 6,909,917 B2 | 6/2005 | Woods et al. |
| 6,950,706 B2 | 9/2005 | Rodriguez et al. |
| 6,999,819 B2 | 2/2006 | Swoyer et al. |
| 7,092,763 B1 | 8/2006 | Griffith et al. |
| 7,096,070 B1 | 8/2006 | Jenkins et al. |
| 7,239,921 B2 | 7/2007 | Canfield et al. |
| 7,346,391 B1 | 3/2008 | Osorio et al. |
| 7,616,990 B2 | 11/2009 | Chavan et al. |
| 7,711,419 B2 | 5/2010 | Armstrong et al. |
| 7,717,848 B2 | 5/2010 | Heruth et al. |
| 7,734,340 B2 | 6/2010 | De Ridder |
| 7,734,354 B1 | 6/2010 | Cox |
| 7,742,818 B2 | 6/2010 | Dinsmoor et al. |
| 7,801,615 B2 | 9/2010 | Meadows et al. |
| 7,899,550 B1 | 3/2011 | Doan et al. |
| 7,912,555 B2 | 3/2011 | Swoyer et al. |
| 7,925,357 B2 | 4/2011 | Phillips et al. |
| 7,991,479 B2 | 8/2011 | Phillips et al. |
| 8,000,805 B2 | 8/2011 | Swoyer et al. |
| 8,036,756 B2 | 10/2011 | Swoyer et al. |
| 8,086,317 B2 | 12/2011 | Finch et al. |
| 8,140,163 B1 | 3/2012 | Daglow et al. |
| 8,170,675 B2 | 5/2012 | Alataris et al. |
| 8,224,453 B2 | 7/2012 | De Ridder |
| 8,260,424 B2 | 9/2012 | Moffitt et al. |
| 8,280,517 B2 | 10/2012 | Skelton et al. |
| 8,314,594 B2 | 11/2012 | Scott et al. |
| 8,334,677 B2 | 12/2012 | Single |
| 8,359,102 B2 | 1/2013 | Alataris et al. |
| 8,364,273 B2 | 1/2013 | De Ridder |
| 8,388,555 B2 | 3/2013 | Panken et al. |
| 8,401,655 B2 | 3/2013 | De Ridder |
| 8,401,666 B2 | 3/2013 | Skelton et al. |
| 8,423,147 B2 | 4/2013 | Alataris et al. |
| 8,433,415 B2 | 4/2013 | Leiter et al. |
| 8,437,853 B2 | 5/2013 | Inman et al. |
| 8,452,421 B2 | 5/2013 | Thenuwara et al. |
| 8,469,971 B2 | 6/2013 | Barker |
| 8,504,138 B1 | 8/2013 | Pivonka et al. |
| 8,504,150 B2 | 8/2013 | Skelton |
| 8,538,541 B2 | 9/2013 | Milojevic et al. |
| 8,579,834 B2 | 11/2013 | Davis et al. |
| 8,612,015 B2 | 12/2013 | Knifong, Sr. |
| 8,620,435 B2 | 12/2013 | Rooney et al. |
| 8,626,297 B2 | 1/2014 | Jaax et al. |
| 8,626,314 B2 | 1/2014 | Swoyer et al. |
| 8,634,928 B1 | 1/2014 | O'Driscoll et al. |
| 8,655,451 B2 | 2/2014 | Klosterman et al. |
| 8,688,217 B2 | 4/2014 | Aghassian et al. |
| 8,706,240 B2 | 4/2014 | Bradley et al. |
| 8,712,533 B2 | 4/2014 | Alataris et al. |
| 8,718,781 B2 | 5/2014 | Alataris et al. |
| 8,758,274 B2 | 6/2014 | Sahasrabudhe et al. |
| 8,768,472 B2 | 7/2014 | Fang et al. |
| 8,774,927 B2 | 7/2014 | Deridder |
| 8,792,988 B2 | 7/2014 | Alataris et al. |
| 8,798,773 B2 | 8/2014 | Mashiach |
| 8,834,392 B2 | 9/2014 | Panken et al. |
| 8,868,192 B2 | 10/2014 | Alataris et al. |
| 8,874,217 B2 | 10/2014 | Alataris et al. |
| 8,874,222 B2 | 10/2014 | Alataris et al. |
| 8,880,177 B2 | 11/2014 | Alataris et al. |
| 8,880,191 B2 | 11/2014 | Pyles et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,897,870 B2 | 11/2014 | De Ridder |
| 8,903,502 B2 | 12/2014 | Perryman et al. |
| 8,934,981 B2 | 1/2015 | De Ridder |
| 8,954,165 B2 | 2/2015 | Sharma et al. |
| 8,965,521 B2 | 2/2015 | Birkholz et al. |
| 8,972,502 B2 | 3/2015 | Beslic et al. |
| 9,020,590 B1 | 4/2015 | Honeycutt et al. |
| 9,031,664 B2 | 5/2015 | Trier |
| 9,044,612 B2 | 6/2015 | Mashiach et al. |
| 9,061,151 B2 | 6/2015 | Mashiach et al. |
| 9,106,203 B2 | 8/2015 | Kesler et al. |
| 9,138,582 B2 | 9/2015 | Doan et al. |
| 9,144,681 B2 | 9/2015 | Decre et al. |
| 9,149,210 B2 | 10/2015 | Sahasrabudhe et al. |
| 9,173,811 B2 | 11/2015 | Greiner et al. |
| 9,174,053 B2 | 11/2015 | Zhu |
| 9,220,897 B2 | 12/2015 | Perryman et al. |
| 9,254,393 B2 | 2/2016 | Perryman et al. |
| 9,272,081 B2 | 3/2016 | Cameron et al. |
| 9,327,125 B2 | 5/2016 | Alataris et al. |
| 9,327,126 B2 | 5/2016 | Alataris et al. |
| 9,327,127 B2 | 5/2016 | Alataris et al. |
| 9,333,357 B2 | 5/2016 | Alataris et al. |
| 9,333,358 B2 | 5/2016 | Alataris et al. |

(56)                References Cited

U.S. PATENT DOCUMENTS

| | | |
|---|---|---|
| 9,339,655 B2 | 5/2016 | Carbunaru |
| 9,393,420 B2 | 7/2016 | Almendinger et al. |
| 9,403,020 B2 | 8/2016 | Wingeier |
| 9,433,750 B2 | 9/2016 | Pivonka et al. |
| 9,440,084 B2 | 9/2016 | Davis et al. |
| 9,452,288 B2 | 9/2016 | Whitehurst et al. |
| 9,462,398 B2 | 10/2016 | DeRidder |
| 9,463,318 B2 | 10/2016 | Mashiach et al. |
| 9,480,842 B2 | 11/2016 | Alataris et al. |
| 9,533,155 B2 | 1/2017 | Jiang et al. |
| 9,555,248 B2 | 1/2017 | De Ridder |
| 9,555,257 B2 | 1/2017 | Mashiach et al. |
| 9,585,642 B2 | 3/2017 | Dinsmoor et al. |
| 9,622,700 B2 | 4/2017 | Sahasrabudhe et al. |
| 9,623,245 B2 | 4/2017 | King et al. |
| 9,623,253 B2 | 4/2017 | Perryman et al. |
| 9,643,010 B2 | 5/2017 | Ranu |
| 9,656,077 B2 | 5/2017 | De Ridder |
| 9,656,085 B2 | 5/2017 | Moffitt et al. |
| 9,656,089 B2 | 5/2017 | Yip et al. |
| 9,707,406 B1 | 7/2017 | Dellamano et al. |
| 9,717,921 B2 | 8/2017 | Perryman et al. |
| 9,731,140 B1 | 8/2017 | Perryman et al. |
| 9,764,135 B2 | 9/2017 | De Ridder |
| 9,770,592 B2 | 9/2017 | Lin et al. |
| 9,789,314 B2 | 10/2017 | Perryman et al. |
| 9,789,321 B2 | 10/2017 | Dixit et al. |
| 9,826,963 B2 | 11/2017 | Scott et al. |
| 9,833,629 B2 | 12/2017 | Dellamano et al. |
| 9,913,975 B2 | 3/2018 | Carbunaru et al. |
| 9,919,159 B2 | 3/2018 | Skelton et al. |
| 9,993,646 B2 | 6/2018 | Parramon et al. |
| 10,004,635 B2 | 6/2018 | Kahook |
| 10,016,603 B2 | 7/2018 | Sachs et al. |
| 10,016,608 B2 | 7/2018 | Peterson et al. |
| 10,016,615 B2 | 7/2018 | Simon et al. |
| 10,016,627 B2 | 7/2018 | Viitala et al. |
| 10,022,549 B2 | 7/2018 | Dellamano et al. |
| 10,022,552 B2 | 7/2018 | Stahler et al. |
| 10,035,017 B2 | 7/2018 | Thakkar et al. |
| 10,035,020 B2 | 7/2018 | Wang et al. |
| 10,052,481 B2 | 8/2018 | McClure et al. |
| 10,076,668 B2 | 9/2018 | De Ridder |
| 10,086,201 B2 | 10/2018 | Chang et al. |
| 10,092,758 B2 | 10/2018 | De Ridder |
| 10,149,976 B1 | 12/2018 | Andresen et al. |
| 10,207,118 B2 | 2/2019 | Skelton |
| 10,238,872 B2 | 3/2019 | Pivonka et al. |
| 10,238,874 B2 | 3/2019 | Perryman et al. |
| 10,245,436 B2 | 4/2019 | Perryman et al. |
| 10,272,239 B1 | 4/2019 | Andresen et al. |
| 10,315,039 B2 | 6/2019 | Perryman et al. |
| 10,320,232 B2 | 6/2019 | Pivonka et al. |
| 10,328,265 B2 | 6/2019 | Moffitt et al. |
| 10,335,596 B2 | 7/2019 | Yakovlev et al. |
| 10,335,599 B2 | 7/2019 | Zottola |
| 10,411,760 B2 | 9/2019 | Yakovlev et al. |
| 10,420,947 B2 | 9/2019 | Perryman et al. |
| 10,471,262 B2 | 11/2019 | Perryman et al. |
| 10,644,539 B2 | 5/2020 | Pivonka et al. |
| 10,682,521 B2 | 6/2020 | Jiang et al. |
| 10,849,643 B2 | 12/2020 | Castillo et al. |
| 10,898,719 B2 | 1/2021 | Pivonka et al. |
| 10,967,183 B2 | 4/2021 | Yakovlev et al. |
| 11,018,721 B2 | 5/2021 | Yakovlev et al. |
| 11,090,491 B2 | 8/2021 | Mishra et al. |
| 11,097,096 B2 | 8/2021 | Linden et al. |
| 11,133,709 B2 | 9/2021 | Pivonka et al. |
| 11,160,980 B2 | 11/2021 | Mishra et al. |
| 11,260,236 B2 | 3/2022 | Mathur et al. |
| 11,318,315 B2 | 5/2022 | Hartley et al. |
| 11,331,493 B2 | 5/2022 | Pivonka et al. |
| 11,451,265 B2 | 9/2022 | Yakovlev et al. |
| 11,511,121 B2 | 11/2022 | Sit et al. |
| 11,633,151 B2 | 4/2023 | Pivonka et al. |
| 11,766,561 B2 | 9/2023 | Mishra et al. |
| 11,826,569 B2 | 11/2023 | Mishra et al. |
| 11,938,327 B2 | 3/2024 | Hartley et al. |
| 12,186,563 B2 | 1/2025 | Yakovlev et al. |
| 12,201,829 B2 | 1/2025 | Linden et al. |
| 12,390,650 B2 | 8/2025 | Sit et al. |
| 12,502,543 B2 | 12/2025 | Pivonka et al. |
| 2002/0014039 A1 | 2/2002 | Merlet |
| 2002/0140399 A1 | 10/2002 | Echarri et al. |
| 2003/0018364 A1 | 1/2003 | Belden et al. |
| 2003/0135253 A1 | 7/2003 | Kokones et al. |
| 2004/0059392 A1 | 3/2004 | Parramon et al. |
| 2004/0088024 A1 | 5/2004 | Firlik et al. |
| 2004/0093039 A1 | 5/2004 | Schumert |
| 2004/0106954 A1 | 6/2004 | Whitehurst et al. |
| 2004/0215287 A1 | 10/2004 | Swoyer et al. |
| 2004/0215306 A1 | 10/2004 | Heil et al. |
| 2005/0043765 A1 | 2/2005 | Williams et al. |
| 2005/0075696 A1 | 4/2005 | Forsberg et al. |
| 2005/0151696 A1 | 7/2005 | Govari et al. |
| 2005/0222656 A1 | 10/2005 | Wahlstrand et al. |
| 2005/0245989 A1 | 11/2005 | Davis |
| 2005/0278000 A1 | 12/2005 | Strother et al. |
| 2005/0288596 A1 | 12/2005 | Eigler et al. |
| 2006/0074458 A1 | 4/2006 | Imran |
| 2006/0095078 A1 | 5/2006 | Tronnes |
| 2006/0122653 A1 | 6/2006 | Bradley et al. |
| 2006/0149330 A1 | 7/2006 | Mann et al. |
| 2006/0217782 A1 | 9/2006 | Boveja et al. |
| 2006/0224225 A1 | 10/2006 | Ransbury et al. |
| 2006/0253174 A1 | 11/2006 | King |
| 2006/0265057 A1 | 11/2006 | Greenberg et al. |
| 2007/0021802 A1 | 1/2007 | Heruth et al. |
| 2007/0032734 A1 | 2/2007 | Najafi et al. |
| 2007/0049986 A1 | 3/2007 | Imran |
| 2007/0049989 A1 | 3/2007 | Rossing et al. |
| 2007/0100411 A1 | 5/2007 | Bonde |
| 2007/0123952 A1 | 5/2007 | Strother et al. |
| 2007/0142874 A1 | 6/2007 | John |
| 2007/0156205 A1 | 7/2007 | Larson et al. |
| 2007/0255368 A1 | 11/2007 | Bonde et al. |
| 2007/0270928 A1 | 11/2007 | Erlebacher |
| 2007/0288076 A1 | 12/2007 | Bulkes et al. |
| 2008/0103569 A1 | 5/2008 | Gerber |
| 2008/0103570 A1 | 5/2008 | Gerber |
| 2008/0103578 A1 | 5/2008 | Gerber |
| 2008/0132981 A1 | 6/2008 | Gerber |
| 2008/0146871 A1 | 6/2008 | Arneson et al. |
| 2008/0161803 A1 | 7/2008 | Oral et al. |
| 2008/0269591 A1 | 10/2008 | Halperin et al. |
| 2008/0300654 A1 | 12/2008 | Lambert et al. |
| 2008/0300656 A1 | 12/2008 | Donders et al. |
| 2008/0300660 A1 | 12/2008 | John |
| 2008/0319492 A1 | 12/2008 | Katsnelson |
| 2009/0082829 A1 | 3/2009 | Panken et al. |
| 2009/0082835 A1 | 3/2009 | Jaax et al. |
| 2009/0088817 A1 | 4/2009 | Starkebaum et al. |
| 2009/0088819 A1 | 4/2009 | Starkebaum et al. |
| 2009/0112282 A1 | 4/2009 | Kast et al. |
| 2009/0171408 A1 | 7/2009 | Solem |
| 2009/0204170 A1 | 8/2009 | Hastings et al. |
| 2009/0216296 A1 | 8/2009 | Meskens |
| 2009/0224361 A1 | 9/2009 | Liu et al. |
| 2009/0275956 A1 | 11/2009 | Burnes et al. |
| 2009/0281597 A1 | 11/2009 | Parramon et al. |
| 2009/0319005 A1 | 12/2009 | Lineaweaver |
| 2010/0010383 A1 | 1/2010 | Skelton et al. |
| 2010/0010392 A1 | 1/2010 | Skelton et al. |
| 2010/0036454 A1 | 2/2010 | Bennett et al. |
| 2010/0048062 A1 | 2/2010 | Cappa et al. |
| 2010/0069996 A1 | 3/2010 | Strahl |
| 2010/0076525 A1 | 3/2010 | Skelton et al. |
| 2010/0082087 A1 | 4/2010 | Silipo et al. |
| 2010/0114189 A1 | 5/2010 | Donofrio et al. |
| 2010/0125312 A1 | 5/2010 | Stevenson et al. |
| 2010/0161002 A1 | 6/2010 | Aghassian et al. |
| 2010/0201368 A1 | 8/2010 | Doerr et al. |
| 2010/0249888 A1 | 9/2010 | Glenn et al. |
| 2010/0274314 A1 | 10/2010 | Alataris et al. |

(56)                    References Cited

U.S. PATENT DOCUMENTS

| | | |
|---|---|---|
| 2010/0274316 A1 | 10/2010 | Alataris et al. |
| 2010/0274318 A1 | 10/2010 | Walker et al. |
| 2010/0305663 A1 | 12/2010 | Aghassian |
| 2010/0331925 A1 | 12/2010 | Peterson |
| 2011/0034886 A1 | 2/2011 | Elbe et al. |
| 2011/0046697 A1 | 2/2011 | Gerber et al. |
| 2011/0054583 A1 | 3/2011 | Litt et al. |
| 2011/0093032 A1 | 4/2011 | Boggs, II et al. |
| 2011/0106214 A1 | 5/2011 | Carbunaru et al. |
| 2011/0172562 A1 | 7/2011 | Sahasrabudhe et al. |
| 2011/0172737 A1 | 7/2011 | Davis et al. |
| 2011/0172743 A1 | 7/2011 | Davis et al. |
| 2011/0184337 A1 | 7/2011 | Evans et al. |
| 2011/0184488 A1 | 7/2011 | De Ridder |
| 2011/0218593 A1 | 9/2011 | Rubinstein et al. |
| 2011/0224665 A1 | 9/2011 | Crosby et al. |
| 2011/0230893 A1 | 9/2011 | Barker |
| 2011/0257707 A1 | 10/2011 | Kothandaraman |
| 2011/0264163 A1 | 10/2011 | Tracey et al. |
| 2011/0301670 A1 | 12/2011 | Gross et al. |
| 2011/0301687 A1 | 12/2011 | Van Waalwijk Van Doorn |
| 2011/0307032 A1 | 12/2011 | Goetz et al. |
| 2012/0004708 A1 | 1/2012 | Chen et al. |
| 2012/0004709 A1 | 1/2012 | Chen et al. |
| 2012/0012630 A1 | 1/2012 | Lui et al. |
| 2012/0016439 A1 | 1/2012 | Alataris et al. |
| 2012/0029597 A1 | 2/2012 | Keacher |
| 2012/0041497 A1 | 2/2012 | Pianca |
| 2012/0041508 A1 | 2/2012 | Rousso et al. |
| 2012/0109256 A1 | 5/2012 | Meskins et al. |
| 2012/0179071 A1 | 7/2012 | Skelton |
| 2012/0221074 A1 | 8/2012 | Funderburk et al. |
| 2012/0283800 A1 | 11/2012 | Perryman et al. |
| 2012/0290041 A1 | 11/2012 | Kim et al. |
| 2012/0296271 A1 | 11/2012 | Yomtov et al. |
| 2012/0296329 A1 | 11/2012 | Ng |
| 2012/0296444 A1 | 11/2012 | Greenberg et al. |
| 2013/0004925 A1 | 1/2013 | Labbe et al. |
| 2013/0012866 A1 | 1/2013 | Deem et al. |
| 2013/0053767 A1 | 2/2013 | Pivonka et al. |
| 2013/0096642 A1 | 4/2013 | Wingeier |
| 2013/0096650 A1 | 4/2013 | Aghassian |
| 2013/0110194 A1 | 5/2013 | Wei |
| 2013/0150925 A1 | 6/2013 | Vamos et al. |
| 2013/0197609 A1 | 8/2013 | Moore et al. |
| 2013/0204321 A1 | 8/2013 | Alataris et al. |
| 2013/0215979 A1 | 8/2013 | Yakovlev et al. |
| 2013/0310706 A1 | 11/2013 | Stone et al. |
| 2013/0310901 A1 | 11/2013 | Perryman et al. |
| 2013/0317564 A1 | 11/2013 | Lin et al. |
| 2013/0331638 A1 | 12/2013 | Cameron et al. |
| 2013/0345202 A1 | 12/2013 | Amselem |
| 2014/0018788 A1 | 1/2014 | Engelman et al. |
| 2014/0025140 A1 | 1/2014 | Lui et al. |
| 2014/0046413 A1 | 2/2014 | Kane et al. |
| 2014/0058467 A1 | 2/2014 | Hamann et al. |
| 2014/0094876 A1 | 4/2014 | Wingeier et al. |
| 2014/0100636 A1 | 4/2014 | Mashiach et al. |
| 2014/0107709 A1 | 4/2014 | Schmitz et al. |
| 2014/0107752 A1 | 4/2014 | Parramon et al. |
| 2014/0163580 A1 | 6/2014 | Tischendorf et al. |
| 2014/0163638 A1 | 6/2014 | Marnfeldt et al. |
| 2014/0163645 A1 | 6/2014 | Dinsmoor et al. |
| 2014/0163646 A1 | 6/2014 | Tischendorf et al. |
| 2014/0172047 A1 | 6/2014 | Spitaels et al. |
| 2014/0180365 A1 | 6/2014 | Perryman et al. |
| 2014/0194771 A1 | 7/2014 | Parker et al. |
| 2014/0222106 A1 | 8/2014 | Sharma et al. |
| 2014/0257428 A1 | 9/2014 | Zhu |
| 2014/0275847 A1 | 9/2014 | Perryman et al. |
| 2014/0277281 A1 | 9/2014 | Grandhe |
| 2014/0277282 A1* | 9/2014 | Jaax .................... A61N 1/36139 607/59 |
| 2014/0288393 A1 | 9/2014 | Grevious et al. |
| 2014/0288616 A1 | 9/2014 | Rawat et al. |
| 2014/0304773 A1 | 10/2014 | Woods et al. |
| 2014/0336727 A1 | 11/2014 | Perryman et al. |
| 2014/0346078 A1 | 11/2014 | Chang |
| 2014/0358197 A1 | 12/2014 | Mashiach et al. |
| 2014/0364714 A1 | 12/2014 | Ameri et al. |
| 2014/0364919 A1 | 12/2014 | Doan |
| 2014/0371515 A1 | 12/2014 | John |
| 2015/0012057 A1 | 1/2015 | Carlson et al. |
| 2015/0018699 A1 | 1/2015 | Zeng et al. |
| 2015/0018728 A1 | 1/2015 | Gross et al. |
| 2015/0035378 A1 | 2/2015 | Calhoun et al. |
| 2015/0080982 A1 | 3/2015 | Van Funderburk |
| 2015/0100109 A1 | 4/2015 | Feldman et al. |
| 2015/0100110 A1 | 4/2015 | Towe et al. |
| 2015/0119673 A1 | 4/2015 | Pellinen et al. |
| 2015/0164401 A1 | 6/2015 | Toth et al. |
| 2015/0224326 A1 | 8/2015 | Toth et al. |
| 2015/0321000 A1 | 11/2015 | Rosenbluth et al. |
| 2015/0321002 A1 | 11/2015 | Khalil et al. |
| 2015/0335285 A1 | 11/2015 | Poon et al. |
| 2015/0360037 A1 | 12/2015 | Hahn et al. |
| 2015/0380972 A1 | 12/2015 | Fort |
| 2016/0008604 A1 | 1/2016 | Doan et al. |
| 2016/0015980 A1 | 1/2016 | Biele et al. |
| 2016/0022988 A1 | 1/2016 | Thieme et al. |
| 2016/0023022 A1 | 1/2016 | Zarins et al. |
| 2016/0030666 A1 | 2/2016 | Lozano et al. |
| 2016/0036261 A1 | 2/2016 | Lenive |
| 2016/0045746 A1 | 2/2016 | Jiang et al. |
| 2016/0082254 A1 | 3/2016 | Moffitt et al. |
| 2016/0106994 A1 | 4/2016 | Crosby et al. |
| 2016/0113671 A1 | 4/2016 | Berger |
| 2016/0121102 A1 | 5/2016 | Tockman et al. |
| 2016/0121124 A1 | 5/2016 | Johanek et al. |
| 2016/0135917 A1 | 5/2016 | Mickle et al. |
| 2016/0136438 A1 | 5/2016 | Perryman et al. |
| 2016/0136443 A1 | 5/2016 | Grandhe et al. |
| 2016/0144184 A1 | 5/2016 | Marnfeldt |
| 2016/0157769 A1 | 6/2016 | Min et al. |
| 2016/0166835 A1 | 6/2016 | De Ridder |
| 2016/0199657 A1 | 7/2016 | Jiang et al. |
| 2016/0199658 A1 | 7/2016 | Nassif et al. |
| 2016/0218433 A1 | 7/2016 | Nghiem et al. |
| 2016/0331956 A1 | 11/2016 | Yakovlev et al. |
| 2016/0346546 A1 | 12/2016 | Zhu |
| 2016/0361545 A1 | 12/2016 | Kaula et al. |
| 2016/0375237 A1 | 12/2016 | Hahn et al. |
| 2017/0001003 A1 | 1/2017 | Pivonka et al. |
| 2017/0028199 A1 | 2/2017 | Roehrlein et al. |
| 2017/0050021 A1 | 2/2017 | Cosman, Sr. |
| 2017/0054324 A1 | 2/2017 | Pivonka et al. |
| 2017/0054332 A1 | 2/2017 | Pivonka et al. |
| 2017/0087353 A1 | 3/2017 | Thota et al. |
| 2017/0095667 A1 | 4/2017 | Yakovlev et al. |
| 2017/0113046 A1 | 4/2017 | Fried et al. |
| 2017/0165491 A9 | 6/2017 | De Ridder |
| 2017/0189683 A1 | 7/2017 | Perryman et al. |
| 2017/0197082 A1 | 7/2017 | Pang et al. |
| 2017/0216602 A1 | 8/2017 | Waataja et al. |
| 2017/0239483 A1 | 8/2017 | Mathur et al. |
| 2017/0252552 A1 | 9/2017 | Cook et al. |
| 2017/0319855 A1* | 11/2017 | Kramer .............. A61N 1/36139 |
| 2017/0368339 A1 | 12/2017 | De Ridder |
| 2018/0028824 A1 | 2/2018 | Pivonka et al. |
| 2018/0064944 A1 | 3/2018 | Grill et al. |
| 2018/0070841 A1 | 3/2018 | Honore et al. |
| 2018/0071512 A1 | 3/2018 | Feldman et al. |
| 2018/0071536 A1 | 3/2018 | Skelton et al. |
| 2018/0083668 A1 | 3/2018 | Yakovlev et al. |
| 2018/0085593 A1 | 3/2018 | Fayram et al. |
| 2018/0140843 A1 | 5/2018 | Kent et al. |
| 2018/0169423 A1 | 6/2018 | Perryman et al. |
| 2018/0193651 A1 | 7/2018 | Annoni et al. |
| 2018/0200520 A1 | 7/2018 | Tranchina et al. |
| 2018/0214699 A1 | 8/2018 | Kothandaraman et al. |
| 2018/0214700 A1 | 8/2018 | Vansickle et al. |
| 2018/0236237 A1 | 8/2018 | Kent et al. |
| 2018/0243563 A1 | 8/2018 | Vallejo et al. |
| 2018/0256906 A1 | 9/2018 | Pivonka et al. |

(56) References Cited

U.S. PATENT DOCUMENTS

| | | |
|---|---|---|
| 2018/0289965 A1 | 10/2018 | Nelson et al. |
| 2018/0296834 A1 | 10/2018 | John et al. |
| 2018/0326220 A1 | 11/2018 | Kaula et al. |
| 2018/0333578 A1* | 11/2018 | Mock et al. |
| 2018/0345019 A1 | 12/2018 | Greenberg et al. |
| 2018/0368875 A1 | 12/2018 | Castillo et al. |
| 2018/0369573 A1 | 12/2018 | Cholette et al. |
| 2019/0001139 A1 | 1/2019 | Mishra et al. |
| 2019/0008556 A1 | 1/2019 | Perryman et al. |
| 2019/0009097 A1 | 1/2019 | Hartley et al. |
| 2019/0030339 A1 | 1/2019 | Baru et al. |
| 2019/0143124 A1 | 5/2019 | Perryman et al. |
| 2019/0151659 A1 | 5/2019 | Mishra et al. |
| 2019/0209844 A1 | 7/2019 | Esteller et al. |
| 2019/0247198 A1 | 8/2019 | Zellmer et al. |
| 2019/0262610 A1 | 8/2019 | Kent et al. |
| 2019/0269913 A1 | 9/2019 | Pivonka et al. |
| 2019/0366094 A1 | 12/2019 | Esteller et al. |
| 2019/0374776 A1 | 12/2019 | Mishra et al. |
| 2019/0388692 A1 | 12/2019 | Dinsmoor et al. |
| 2020/0038660 A1 | 2/2020 | Torgerson |
| 2020/0101291 A1 | 4/2020 | Yakovlev et al. |
| 2020/0108253 A1 | 4/2020 | Crowder et al. |
| 2020/0129108 A1 | 4/2020 | Parker et al. |
| 2020/0132434 A1 | 4/2020 | Riahi et al. |
| 2020/0139138 A1 | 5/2020 | Sit et al. |
| 2020/0147388 A1 | 5/2020 | Huertas Fernandez et al. |
| 2020/0171313 A1 | 6/2020 | Dinsmoor et al. |
| 2020/0204209 A1 | 6/2020 | Yakovlev et al. |
| 2020/0206511 A1 | 7/2020 | Goedeke et al. |
| 2020/0222000 A1 | 7/2020 | Poon et al. |
| 2020/0305745 A1 | 10/2020 | Wagenbach et al. |
| 2020/0306528 A1 | 10/2020 | Linden et al. |
| 2020/0398058 A1 | 12/2020 | Pivonka et al. |
| 2021/0099015 A1 | 4/2021 | Pivonka et al. |
| 2021/0187300 A1* | 6/2021 | Dinsmoor ............. A61B 5/1116 |
| 2021/0196957 A1 | 7/2021 | Yakovlev et al. |
| 2021/0330981 A1 | 10/2021 | Mishra et al. |
| 2021/0399765 A1 | 12/2021 | Yakovlev et al. |
| 2022/0016103 A1 | 1/2022 | Baltcheva et al. |
| 2022/0016430 A1 | 1/2022 | Hartley et al. |
| 2022/0072300 A1 | 3/2022 | Yakovlev et al. |
| 2022/0080189 A1 | 3/2022 | Mishra et al. |
| 2022/0118251 A1 | 4/2022 | Buddha et al. |
| 2022/0126103 A1 | 4/2022 | Pivonka et al. |
| 2022/0134108 A1 | 5/2022 | Dinsmoor et al. |
| 2022/0176108 A1 | 6/2022 | Linden et al. |
| 2022/0176120 A1 | 6/2022 | Kulkarni et al. |
| 2022/0176133 A1 | 6/2022 | Buddha et al. |
| 2022/0218994 A1 | 7/2022 | Mishra et al. |
| 2022/0263346 A1 | 8/2022 | Pivonka et al. |
| 2023/0029600 A1 | 2/2023 | Pivonka et al. |
| 2023/0129373 A1 | 4/2023 | Sit et al. |
| 2023/0146724 A1 | 5/2023 | Debock et al. |
| 2024/0041399 A1 | 2/2024 | Pivonka |
| 2024/0050747 A1 | 2/2024 | Mishra et al. |
| 2024/0050758 A1 | 2/2024 | Castillo et al. |
| 2024/0226548 A1 | 7/2024 | Mishra et al. |
| 2024/0278022 A1 | 8/2024 | Mishra et al. |
| 2024/0307687 A1 | 9/2024 | Mishra et al. |
| 2025/0158657 A1 | 5/2025 | Yakovlev et al. |
| 2025/0213872 A1 | 7/2025 | Pivonka et al. |
| 2025/0325812 A1 | 10/2025 | Yakovlev et al. |
| 2025/0332408 A1 | 10/2025 | Linden et al. |

FOREIGN PATENT DOCUMENTS

| | | | |
|---|---|---|---|
| EP | 2155330 B1 | 10/2014 | |
| WO | WO-9500203 A1 | 1/1995 | |
| WO | WO-2005105201 A2 | 11/2005 | |
| WO | WO-2007051146 A1 | 5/2007 | |
| WO | WO-2007068284 A1 | 6/2007 | |
| WO | WO-2008066556 A1 | 6/2008 | |
| WO | WO-2009045297 A1 | 4/2009 | |
| WO | WO-2010051062 A1 | 5/2010 | |
| WO | WO-2010062517 A1 | 6/2010 | |
| WO | WO-2013035092 A2 | 3/2013 | |
| WO | WO-2014071079 A1 | 5/2014 | |
| WO | WO-2014089299 A2 | 6/2014 | |
| WO | WO-2014145222 A2 | 9/2014 | |
| WO | WO-2014153124 A1 | 9/2014 | |
| WO | WO-2014153219 A1 | 9/2014 | |
| WO | WO-2014153228 A1 | 9/2014 | |
| WO | WO-2014205129 A1 | 12/2014 | |
| WO | WO-2015139053 A1 | 9/2015 | |
| WO | WO-2015179177 A1 | 11/2015 | |
| WO | WO-2015196164 A2 | 12/2015 | |
| WO | WO-2015196164 A3 | 2/2016 | |
| WO | WO-2016028608 A1 | 2/2016 | |
| WO | WO-2016113832 A1 | 7/2016 | |
| WO | WO-2016127130 A1 | 8/2016 | |
| WO | WO-2016191055 A1 | 12/2016 | |
| WO | WO-2017044904 A1 | 3/2017 | |
| WO | WO-2017142948 A1 | 8/2017 | |
| WO | WO-2017165410 A1 | 9/2017 | |
| WO | WO-2017205675 A1 | 11/2017 | |
| WO | WO-2018017463 A1 | 1/2018 | |
| WO | WO-2018023057 A1 | 2/2018 | |
| WO | WO-2018126062 A1 | 7/2018 | |
| WO | WO-2018144631 A1 | 8/2018 | |
| WO | WO-2018156953 A1 | 8/2018 | |
| WO | WO-2018170141 A1 | 9/2018 | |
| WO | WO-2018208992 A1 | 11/2018 | |
| WO | WO-2019226557 A1 | 11/2019 | |
| WO | WO-2019226568 A1 | 11/2019 | |
| WO | WO-2020070492 A1 | 4/2020 | |
| WO | WO-2021003439 A1 | 1/2021 | |
| WO | WO-2021067873 A1 | 4/2021 | |
| WO | WO-2021133947 A1 | 7/2021 | |
| WO | WO-2021262762 A1 | 12/2021 | |
| WO | WO-2022047077 A1 | 3/2022 | |
| WO | WO-2022103774 A1 | 5/2022 | |
| WO | WO-2022197748 A1 | 9/2022 | |
| WO | WO-2025158408 A1 | 7/2025 | |

OTHER PUBLICATIONS

Butson, C. et al., "Current steering to Control the Volume of Tissue Activated During Deep Brain Stimulation" Brain Stimul. (2008) (1): 7-15.

EP14813206 Examination Report dated Apr. 23, 2020. 2 pages.

EP15809379.9 European Search Report dated Mar. 9, 2018. 7 pages.

European Search Report and Written Opinion in EP Application No. 16845235.7, mailed Apr. 24, 2019, 8 pages.

European Search Report and Written Opinion in EP Application No. 13852295.8, mailed May 12, 2016, 10 pages.

European Search Report and Written Opinion in EP Application No. 16747389.1, mailed Jul. 5, 2018, 8 pages.

European Search Report and Written Opinion in EP Application No. 17753756.0, mailed Nov. 11, 2019, 9 pages.

European Search Report and Written Opinion in EP Application No. 17770982.1, mailed Sep. 26, 2019, 7 pages.

European Search Report and Written Opinion in EP Application No. 17831624.6, mailed Feb. 20, 2020, 9 pages.

European Search Report and Written Opinion in EP Application No. 18756643.5, mailed Dec. 3, 2020, 10 pages.

European Search Report and Written Opinion in EP Application No. 18797777.2, mailed Jan. 14, 2021, 7 pages.

Extended European Search Report for European Application No. EP23186171.7 dated Jan. 5, 2024, 7 pages.

Extended European Search Report mailed on Jan. 3, 2024, for EP Application No. 20871125.9, 15 pages.

Final Office Action for U.S. Appl. No. 16/111,868 mailed on Mar. 11, 2021, 24 pages.

Final Office Action for U.S. Appl. No. 17/372,095 dated Jun. 16, 2023, 31 pages.

Final Office Action for U.S. Appl. No. 17/379,928 dated Jul. 17, 2023, 13 pages.

(56) References Cited

OTHER PUBLICATIONS

Final Office Action mailed on Aug. 18, 2023, for U.S. Appl. No. 17/240,629, filed Apr. 26, 2021, 11 pages.

Final Office Action mailed on Nov. 1, 2023, for U.S. Appl. No. 17/726,378, filed Apr. 21, 2022, 15 pages.

Final Office Action for U.S. Appl. No. 16/222,959 mailed on Nov. 21, 2022, 21 pages.

International Preliminary Report on Patentability for International Application No. PCT/US2021/047815, mailed Mar. 9, 2023, 6 pages.

International Search Report and Written Opinion for PCT/US2014/043023; Oct. 6, 2014, 13 pages.

International Search Report and Written Opinion for PCT/US2015/020808, Jun. 24, 2015, 8 pages.

International Search Report and Written Opinion for PCT/US2015/036821, Dec. 18, 2015, 13 pages.

International Search Report and Written Opinion for PCT/US2016/016888, Apr. 14, 2016, 8 pages.

International Search Report and Written Opinion for PCT/US2016/051177, Nov. 10, 2016, 18 pages.

International Search Report and Written Opinion for PCT/US2017/017978, May 5, 2017, 7 pages.

International Search Report and Written Opinion for PCT/US2017/023400, May 23, 2017, 8 pages.

International Search Report and Written Opinion for PCT/US2017/042351, Sep. 26, 2017, 9 pages.

International Search Report and Written Opinion for PCT/US2018/019522, Jun. 15, 2018, 12 pages.

International Search Report and Written Opinion for PCT/US2018/031904, Jul. 26, 2018, 10 pages.

International Search Report and Written Opinion for PCT/US2020/054150, Jan. 6, 2021, 11 pages.

International Search Report and Written Opinion for PCT/US2020/066901, Mar. 15, 2021, 7 pages.

International Search Report and Written Opinion for PCT/US2021/038545, Mar. 15, 2021, 7 pages.

International Search Report and Written Opinion mailed on Jan. 31, 2022 for PCT/US2021/058673, 8 pages.

International Search Report and Written Opinion mailed on May 18, 2022, for PCT Application No. PCT/US2022/020452, filed Mar. 15, 2022, 8 pages.

Lee et al, "Predicted effects of pulse width programming in spinal cord stimulation: a mathematical modeling study" Med Biol Eng Comput 49:765-774 (2011). https://doi.org/1 0.1007 /s11517-011-0780-9.

Lenssen, Anneke et al., "Bimodal listeners are not sensitive to interaural time differences in unmodulated low-frequency stimuli," The Journal of the Acoustical Society of America, American Institute of Physics for the Acoustical Society of America, New York, NY, vol. 129, No. 6, Jun. 1, 2011, pp. 3457-3460.

Non-Final Office Action for U.S. Appl. No. 14/975,358 dated Aug. 8, 2019. 12 pages.

Non-Final Office Action for U.S. Appl. No. 16/111,868 mailed on Jul. 8, 2021, 30 pages.

Non-Final Office Action for U.S. Appl. No. 17/726,378 dated Apr. 14, 2023, 15 pages.

Non-Final Office Action for U.S. Appl. No. 18/046,042 dated Aug. 23, 2023, 13 pages.

Non-Final Office Action mailed on Feb. 24, 2023, for U.S. Appl. No. 17/240,629, filed Apr. 26, 2021, 12 pages.

Non-Final Office Action mailed on Mar. 22, 2023, for U.S. Appl. No. 17/489,580, filed Sep. 29, 2021, 16 pages.

Notice of Allowance for U.S. Appl. No. 16/222,959 dated May 22, 2023, 11 pages.

Notice of Allowance for U.S. Appl. No. 17/487,535 dated Jul. 20, 2023, 9 pages.

Notice of Allowance for U.S. Appl. No. 17/489,580 dated Nov. 22, 2023, 9 pages.

Office Action dated Oct. 20, 2017 for U.S. Appl. No. 15/264,864, 14 pages.

Partial Supplementary European Search Report mailed on Sep. 18, 2023, for EP Application No. 20871125.9, 14 pages.

PCT/US2017/034553 International Search Report and Written Opinion dated Oct. 10, 2017, 9 pages.

U.S. Appl. No. 14/975,358 Office Action dated Dec. 5, 2019, 9 pages.

U.S. Appl. No. 14/975,358 Office Action dated Jul. 27, 2020, 12 pages.

U.S. Appl. No. 14/975,358 Office Action dated May 15, 2018, 9 pages.

U.S. Appl. No. 14/975,358 Office Action dated Nov. 2, 2020, 18 pages.

U.S. Appl. No. 14/975,358 Office Action dated Nov. 20, 2018, 9 pages.

U.S. Appl. No. 15/664,231 Office Action dated Aug. 6, 2020, 14 pages.

U.S. Appl. No. 15/664,231 Office Action dated Jan. 24, 2020, 15 pages.

U.S. Appl. No. 15/664,231 Office Action dated Jul. 10, 2020, 14 pages.

U.S. Appl. No. 15/664,231 Office Action dated Mar. 8, 2021, 25 pages.

U.S. Appl. No. 16/104,829 Notice of Allowance dated Jul. 6, 2021, 5 pages.

U.S. Appl. No. 16/104,829 Office Action dated Jan. 8, 2021, 20 pages.

U.S. Appl. No. 16/104,829 Office Action dated May 21, 2020, 15 pages.

U.S. Appl. No. 16/672,921 Notice of Allowance dated Apr. 23, 2021, 7 pages.

U.S. Appl. No. 16/672,921 Office Action dated Feb. 16, 2021, 10 pages.

U.S. Appl. No. 16/672,921 Office Action dated Mar. 22, 2021, 11 pages.

Yakovlev, Anatoly et al., "Implantable Biomedical Devices: Wireless powering and communication," IEEE Communications Magazinem, IEEE Service Center, vol. 50, No. 4, Apr. 1, 2012, pp. 152-159.

Crosby et al., "Burst and Tonic Spinal Cord Stimulation Differentially Activate GABAergic Mechanisms to Attenuate Pain in a Rat Model of Cervical Radiculopathy" IEEE Transactions on Biomedical Engineering Jun. 2015; 62(6):1604-1613.

U.S. Appl. No. 17/726,378, Ex Parte Quayle Action mailed May 29, 2025; Inventor Pivonka, Daniel et al; 5 pages.

EP Application No. 21862769.3, Extended European Search Report mailed Jul. 25, 2024; Applicant Nalu Medical, Inc.; 6 pages.

EP Application No. 21892687.1, Extended European Search Report mailed Sep. 18, 2024; Applicant Nalu Medical, Inc., 6 pages.

EP Application No. 22772095.0, Extended European Search Report mailed Dec. 23, 2024; Applicant Nalu Medical, Inc.; 9 pages.

EP Application No. 24167314.4, Extended European Search Report mailed Sep. 23, 2024; Applicant Nalu Medical, Inc.; 8 pages.

EP Application No. 24193745.7, Extended European Search Report mailed Feb. 11, 2025; Applicant Nalu Medical, Inc.; 9 pages.

EP Application No. 25170468.0, Extended European Search Report mailed Aug. 21, 2025; Applicant Nalu Medical, Inc.; 7 pages.

EP Application No. 21827905.7, Extended European Search Report mailed Jun. 18, 2024; Applicant Nalu Medical, Inc.; 5 pages.

EP Application No. 24157465.6, Extended European Search Report mailed Jun. 27, 2024; Applicant Nalu Medical, Inc.; 7 pages.

U.S. Appl. No. 17/372,095, Final Office Action mailed Oct. 2, 2024; Inventor Mishra, Lakshmi Narayan et al.; 30 pages.

U.S. Appl. No. 17/384,020, Final Office Action mailed Oct. 11, 2024; Inventor Buddha, Rushidev et al.; 36 pages.

U.S. Appl. No. 17/726,378, Final Office Action mailed Dec. 16, 2024; Inventor Pivonka, Daniel et al.; 15 pages.

U.S. Appl. No. 18/490,419, Final Office Action mailed Apr. 18, 2025; Inventor Mishra, Lakshmi Narayan et al.; 21 pages.

He et al., "The Electrically Evoked Compound Action Potential: From Laboratory to Clinic" Frontiers in Neuroscience Jun. 2017; 11:339, 20 pages.

U.S. Appl. No. 17/372,095, Non-Final Office Action mailed Mar. 11, 2024; Inventor Mishra, Lakshmi Narayan et al.; 32 pages.

(56)         References Cited

OTHER PUBLICATIONS

U.S. Appl. No. 17/379,928, Non-Final Office Action mailed Jan. 29, 2024; Inventor Linden, Christopher et al.; 16 pages.
U.S. Appl. No. 17/383,972, Non-Final Office Action mailed Dec. 3, 2024; Inventor Kulkarni, Gaurav Gajanan et al.; 23 pages.
U.S. Appl. No. 17/383,985, Non-Final Office Action mailed Dec. 27, 2024; Inventor Mishra, Lakshmi Narayan et al.; 14 pages.
U.S. Appl. No. 17/384,020, Non-Final Office Action mailed Jan. 23, 2024; Inventor Buddha, Rushidev et al.; 28 pages.
U.S. Appl. No. 17/412,044, Non-Final Office Action mailed Feb. 2, 2024; Inventor Pivonka, Daniel et al.; 12 pages.
U.S. Appl. No. 18/174,557, Non-Final Office Action mailed Sep. 10, 2025; Inventor Mishra, Lakshmi Narayan et al.; 9 pages.
U.S. Appl. No. 18/453,154, Non-Final Office Action mailed Oct. 16, 2025; Inventor Mishra, Lakshmi Narayan et al.; 9 pages.
U.S. Appl. No. 18/463,225, Non-Final Office Action mailed Aug. 20, 2025; Inventor Mishra, Lakshmi Narayan et al.; 9 pages.
U.S. Appl. No. 18/490,419, Non-Final Office Action mailed Jul. 18, 2024; Inventor Mishra, Lakshmi Narayan et al.; 13 pages.
U.S. Appl. No. 18/490,419, Non-Final Office Action mailed Oct. 22, 2025; Inventor Mishra, Lakshmi Narayan et al.; 42 pages.
U.S. Appl. No. 17/726,378, Non-Final Office Action mailed May 20, 2024; Inventor Pivonka, Daniel et al.; 11 pages.
U.S. Appl. No. 17/372,095, Notice of Allowance mailed Oct. 7, 2025; Inventor Mishra, Lakshmi Narayan et al.; 5 pages.
U.S. Appl. No. 17/379,928, Notice of Allowance mailed Sep. 18, 2024; Inventor Linden, Christopher et al.; 7 pages.
U.S. Appl. No. 17/726,378, Notice of Allowance mailed Aug. 26, 2025; Inventor Pivonka, Daniel et al.; 7 pages.
Stack Exchange, "Can the saturation of an OPA influence its input?" https://electronics.stackexchange.com/questions/174179/can-the-saturation-of-an-opa-influence-its-input, Jun. 6, 2015, accessed Jul. 15, 2025, 2 pages.
U.S. Appl. No. 19/399,426, filed Nov. 24, 2025; Inventor Pivonka, Daniel et al.
Wheatley and Lehmann, "Electrically evoked compound action potential (ECAP) stimulus-artefact (SA) blanking low-power low-noise CMOS amplifier," 2007 50th Midwest Symposium on Circuits and Systems, Montreal, QC, Canada, Sep. 2007; pp. 41-44.
Wikipedia, "Negative-feedback amplifier," https://en.wikipedia.org/wiki/Negative-feedback_amplifier, accessed Jul. 24, 2025, 8 pages.

* cited by examiner

APPARATUS FOR DELIVERING ENHANCED STIMULATION WAVEFORMS

CROSS REFERENCE TO RELATED APPLICATIONS

The present application is a continuation of International PCT Application No. PCT/US2021/058673, titled "Apparatus For Delivering Enhanced Stimulation Waveforms", filed Nov. 9, 2021, which claims priority to: U.S. Provisional Patent Application No. 63/112,055, titled "Apparatus for Delivering Enhanced Stimulation Waveforms", filed Nov. 10, 2020; and U.S. Provisional Patent Application No. 63/218,159, titled "Apparatus for Delivering Enhanced Stimulation Waveforms", filed Jul. 2, 2021; the contents of each of which is incorporated herein by reference in its entirety for all purposes.

The subject matter of this application is related to that in: U.S. patent application Ser. No. 16/222,959, titled "Methods and Systems for Treating Pelvic Disorders and Pain Conditions", filed Dec. 17, 2018; U.S. patent application Ser. No. 16/266,822, titled "Method and Apparatus for Versatile Minimally Invasive Neuromodulators", filed Feb. 4, 2019; U.S. patent application Ser. No. 16/453,917, titled "Stimulation Apparatus", filed Jun. 26, 2019; U.S. patent application Ser. No. 16/505,425, titled "Wireless Implantable Sensing Devices", filed Jul. 8, 2019; U.S. patent application Ser. No. 16/993,999, titled "Apparatus for Peripheral or Spinal Stimulation", filed Aug. 14, 2020; U.S. patent application Ser. No. 17/081,351, titled "Methods and Systems for Insertion and Fixation of Implantable Devices", filed Oct. 27, 2020; U.S. patent application Ser. No. 17/187,654, titled "Method and Apparatus for Neuromodulation Treatments of Pain and Other Conditions", filed Feb. 26, 2021; U.S. Provisional Patent Application No. 63/161,757, titled "Apparatus for Delivering Enhanced Stimulation Waveforms", filed Mar. 16, 2021; U.S. patent application Ser. No. 17/240,629, titled "Method and Apparatus for Minimally Invasive Implantable Modulators", filed Apr. 26, 2021; U.S. patent application Ser. No. 17/372,095, titled "Apparatus with Enhanced Stimulation Waveforms", filed Jul. 9, 2021; U.S. patent application Ser. No. 17/379,928, titled "Stimulation Apparatus", filed Jul. 19, 2021; U.S. patent application Ser. No. 17/383,915, titled "Stimulation Apparatus", filed Jul. 23, 2021; U.S. patent application Ser. No. 17/383,972, titled "Systems with Implanted Conduit Tracking", filed Jul. 23, 2021; U.S. patent application Ser. No. 17/383,985, titled "Stimulation Energy Systems with Current Steering", filed Jul. 23, 2021; U.S. patent application Ser. No. 17/384,020, titled "Stimulation Apparatus", filed Jul. 23, 2021; U.S. patent application Ser. No. 17/412,044, titled "Medical Apparatus Including an Implantable System and an External System", filed Aug. 25, 2021; International PCT Patent Application No. PCT/US2021/047815, titled "Apparatus for Delivering Customized Stimulation Waveforms", filed Aug. 26, 2021; U.S. patent application Ser. No. 17/487,535, titled "Apparatus with Sequentially Implanted Stimulators", filed Sep. 28, 2021; U.S. patent application Ser. No. 17/489,580, titled "Devices and Methods for Positioning External Devices in Relation to Implanted Devices", filed Sep. 29, 2021; and U.S. Provisional Patent Application No. 63/273,068, titled "Apparatus for Delivering Enhanced Stimulation Waveforms", filed Oct. 28, 2021; the contents of each of which is incorporated herein by reference in its entirety for all purposes.

TECHNICAL FIELD

The present inventive concept relates generally to medical apparatus for a patient, and in particular, apparatus that deliver enhanced stimulation to effectively deliver a therapy while avoiding undesired effects.

BACKGROUND

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g. to treat pain). Most implants are relatively large devices with batteries and long conduits, such as implantable leads configured to deliver electrical energy or implantable tubes (i.e. catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices and methods that provide one or more implantable devices and are designed to provide enhanced treatment of pain and other enhanced benefits.

SUMMARY

According to an aspect of the present inventive concepts, an apparatus for delivering stimulation energy to a patient, comprises: a controller and a memory coupled to the controller, wherein the memory stores instructions for the controller to perform an algorithm, wherein the algorithm is configured to determine a stimulation paradigm comprising one or more stimulation parameter settings; and an implantable system comprising an implantable device. The implantable device comprises: at least one sensor for measuring a neural response, such as evoked compound action potentials (eCAPs) and/or muscle responses (e.g. an electromyography measured response, referred to as "EMG response" or "EMG" herein); and multiple stimulation elements configured to deliver the stimulation energy to tissue based on the stimulation paradigm. The algorithm is configured to determine the stimulation paradigm based on the measured evoked compound action potentials.

In some embodiments, the multiple stimulation elements comprise the at least one sensor. The at least one sensor can comprise one or more electrodes.

In some embodiments, the stimulation energy delivered to tissue comprises energy delivered at a rate greater than 100 Hz. The stimulation energy delivered can comprise energy delivered at a rate greater than 500 Hz, 1000 Hz, and/or 10,000 Hz.

In some embodiments, the stimulation energy delivered comprises multiple pulse trains, and the algorithm is configured to optimize the delivery of the multiple pulse trains. The multiple pulse trains can comprise trains with a rate of at least 100 Hz.

In some embodiments, the at least one sensor is configured to record the neural response (e.g. eCAPs and/or EMGs) during a trialing session and/or during an implantation procedure of the implantable device.

In some embodiments, the stimulation energy delivered comprises a stimulation waveform including a refractory waiting period. The stimulation energy can be delivered to one or more neurons, and the refractory waiting period comprises a time period that is of sufficient length to avoid delivering energy to neurons that are still in their refractory period. The refractory waiting period can comprise a time period of at least 0.5 msec, 1 msec, 5 msec, and/or 10 msec.

In some embodiments, the stimulation energy delivered comprises a first pulse train and a subsequent second pulse train, and the algorithm is configured to determine a refractory waiting period based on the measurement of a first neural response (e.g. a first eCAP or a first EMG), and the second pulse train is delivered at a time when the magnitude of the first neural response has decreased to a threshold level. The threshold level can comprise a level corresponding to at least a 50% decrease in the first neural response magnitude (e.g. eCAP magnitude or EMG magnitude). The threshold level can comprise a level corresponding to at least a 90% decrease in the first neural response magnitude (e.g. eCAP magnitude or EMG magnitude). The threshold level can comprise a level corresponding to at least a 99% decrease in the first neural response magnitude. The threshold level can be heuristically assigned by the apparatus. The threshold can comprise a level of between 20% and 100% of a maximum neural response level.

In some embodiments, the neural response is measured during a time period in which the patient is receiving therapy from the apparatus.

In some embodiments, the apparatus is configured to maintain the neural response at a relatively constant magnitude.

In some embodiments, the apparatus is configured to provide increased neural response magnitudes by increasing the amplitude of stimulation pulses delivered by the apparatus.

In some embodiments, the apparatus is configured to provide increased neural response magnitudes by increasing the pulse width of stimulation pulses delivered by the apparatus.

In some embodiments, the apparatus is configured to provide increased neural response magnitudes by increasing the amplitude and pulse width of stimulation pulses delivered by the apparatus.

In some embodiments, the apparatus is configured to increase the gap between stimulation pulses to allow a larger recovery of neural response magnitudes.

In some embodiments, the amplitude and/or the inter-pulse-interval are changed to keep neural response magnitudes constant.

In some embodiments, the apparatus is configured to steer the stimulation energy delivered by the multiple stimulation elements. The apparatus can be configured to steer the stimulation energy to a location in which target neural structures are relatively (e.g. most) dense.

In some embodiments, the apparatus is configured to deliver the stimulation energy to at least two target areas simultaneously. At least two overlapping fields can be generated by the stimulation energy delivery. The at least two overlapping fields can result in a summative signal delivered to target tissue that approaches being stochastic. The summative signal can avoid causing paresthesia.

In some embodiments, the neural response comprises one or more eCAP responses, one or more EMG responses, or both at least one eCAP response and at least one EMG response.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference. The content of all publications, patents, and patent applications mentioned in this specification are herein incorporated by reference in their entirety for all purposes.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

DETAILED DESCRIPTION OF THE DRAWINGS

Figure 1:
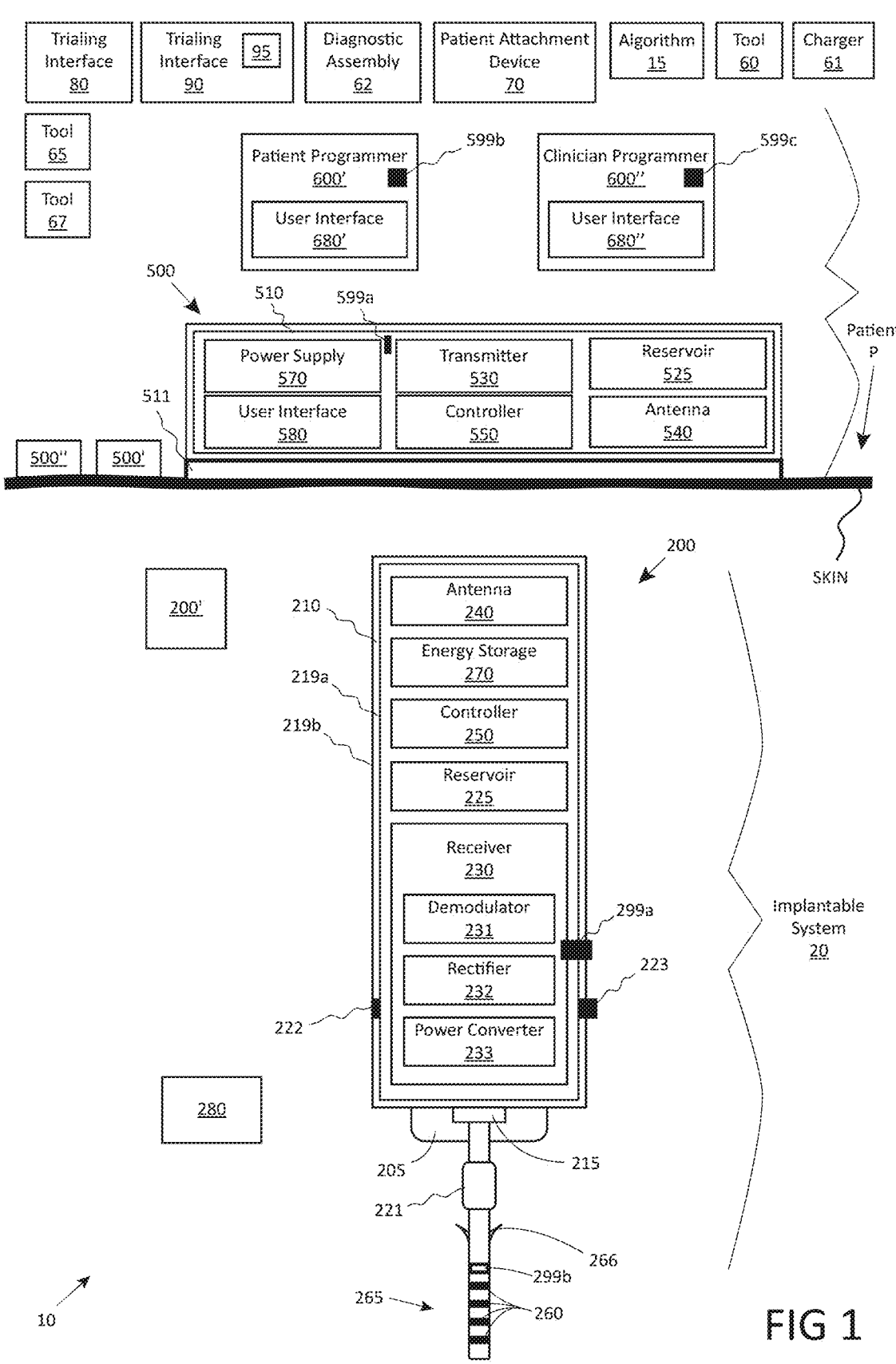
FIG. 1 is a schematic anatomical view of a medical apparatus comprising an external system and an implantable system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers, and/or sections, these limitations, elements, components, regions, layers, and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.). A first component (e.g. a device, assembly, housing or other component) can be "attached", "connected" or "coupled" to another component via a connecting filament (as defined below). In some embodiments, an assembly comprising multiple components connected by one or more connecting filaments is created during a manufacturing process (e.g. pre-connected at the time of an implantation procedure of the apparatus of the present inventive concepts). Alternatively or additionally, a connecting filament can comprise one or more connectors (e.g. a connectorized filament comprising a connector on one or both ends), and a similar assembly can be created by a user (e.g. a clinician) operably attaching the one or more connectors of the connecting filament to one or more mating connectors of one or more components of the assembly.

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

As used herein, the term "proximate" shall include locations relatively close to, on, in, and/or within a referenced component or other location.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross-sectional area as the cross section of the component being described.

The terms "major axis" and "minor axis" of a component where used herein are the length and diameter, respectively, of the smallest volume hypothetical cylinder which can completely surround the component.

The term "functional element" where used herein, is the be taken to include a component comprising one, two or more of: a sensor; a transducer; an electrode; an energy delivery element; an agent delivery element; a magnetic field generating transducer; and combinations of one or more of these. In some embodiments, a functional element comprises a transducer selected from the group consisting of: light delivery element; light emitting diode; wireless transmitter; Bluetooth device; mechanical transducer; piezoelectric transducer; pressure transducer; temperature transducer; humidity transducer; vibrational transducer; audio transducer; speaker; and combinations of one or more of these. In some embodiments, a functional element comprises a needle, a catheter (e.g. a distal portion of a catheter), an iontophoretic element or a porous membrane, such as an agent delivery element configured to deliver one or more agents. In some embodiments, a functional element comprises one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; orientation sensor; motion sensor; and combinations of one or more of these.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy, mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); thermal energy to tissue (e.g. heat energy and/or cryogenic energy); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include one or more signals transmitted using body conduction. Alternatively or additionally, a transmission signal can comprise reflected energy, such as energy reflected from any power and/or data signal.

The term "data signal" where used herein is to be taken to include a transmission signal including at least data. For example, a data signal can comprise a transmission signal including data and sent between a component external to the patient and one or more components implanted in the patient. Alternatively, a data signal can comprise a transmission signal including data sent from an implanted component to one or more components external to the patient. A data signal can comprise a radiofrequency signal including data (e.g. a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

The terms "attachment", "attached", "attaching", "connection", "connected", "connecting" and the like, where used herein, are to be taken to include any type of connection between two or more components. The connection can include an "operable connection" or "operable attachment" which allows multiple connected components to operate together such as to transfer information, power, and/or material (e.g. an agent to be delivered) between the components. An operable connection can include a physical connection, such as a physical connection including a connection between two or more: wires or other conductors (e.g. an "electrical connection"), optical fibers, wave guides, tubes such as fluid transport tubes, and/or linkages such as translatable rods or other mechanical linkages. Alternatively or additionally, an operable connection can include a non-physical or "wireless" connection, such as a wireless connection in which information and/or power is transmitted between components using electromagnetic energy. A connection can include a connection selected from the group consisting of: a wired connection; a wireless connection; an electrical connection; a mechanical connection; an optical connection; a sound propagating connection; a fluid connection; and combinations of one or more of these.

The term "connecting filament" where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term "connectorized" where used herein is to be taken to refer to a filament, housing or other component that includes one or more connectors (e.g. clinician or other user-attachable connectors) for operably connecting that component to a mating connector (e.g. of the same or different component).

The terms "stimulation parameter", "stimulation signal parameter" or "stimulation waveform parameter" where used herein can be taken to refer to one or more parameters of a stimulation waveform (also referred to as a stimulation signal). A "stimulation paradigm SP" can represent one or more sets of stimulation parameters to be used in delivering stimulation energy. Applicable stimulation parameters of the present inventive concepts shall include but are not limited to: amplitude (e.g. amplitude of voltage and/or current); average amplitude; peak amplitude; frequency; average frequency; pulse width (also referred to as "pulse pattern on time"); period; phase; polarity; pulse shape; a duty cycle parameter (e.g. frequency, pulse width, and/or off time); inter-pulse gap (also referred to as "pulse pattern off time", or "inter-pulse interval"); polarity; burst-on (also referred to as "dosage on") period; burst-off (also referred to as "dosage off") period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations of one or more of these. A stimulation parameter can refer to a single stimulation pulse, multiple stimulation pulses, or a portion of a stimulation pulse. The term "amplitude" where used herein can refer to an instantaneous or continuous amplitude of one or more stimulation pulses (e.g. the instantaneous voltage level or current level of a pulse). The term "pulse" where used herein can refer to a period of time during which stimulation energy is relatively continuously being delivered. In some embodiments, stimulation energy delivered during a pulse comprises energy selected from the group consisting of: electrical energy; magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, stimulation energy comprises electrical energy and a pulse comprises a phase change in current and/or voltage. In these embodiments, an "inter-phase gap" can be present within a single pulse. The term inter-phase gap where used herein can refer to a period of time between two portions of a pulse comprising a phase change during which zero energy or minimal energy is delivered. The term "quiescent period" where used herein can refer to a period of time during which zero energy or minimal energy is delivered (e.g. insufficient energy to elicit an action potential and/or other neuronal response). The term "inter-pulse gap" where used herein can refer to a quiescent period between the end of one pulse to the onset of the next (sequential) pulse. The terms "pulse train" or "train" where used herein can refer to a series of pulses. The terms "burst", "burst of pulses" or "burst stimulation" where used herein can refer to a series of pulse trains, each separated by a quiescent period. The term "train-on period" where used herein can refer to a period of time from the beginning of the first pulse to the end of the last pulse of a single train. The term "train-off period" where used herein can refer to a quiescent period between the end of one train and the beginning of the next train. The term "burst-on period" where used herein can refer to a period of time from the beginning of the first pulse of the first train to the end of the last pulse of the last train of a single burst. The term "burst-off period" where used herein can refer to a quiescent period between the end of one burst and the beginning of the next burst. The term "inter-train period" where used herein can refer to a quiescent period between the end of one train and the beginning of the next train. The term "inter-burst period" where used herein can refer to a quiescent period between the end of one burst and the beginning of the next burst. The term "train envelope" where used herein can refer to a curve outlining the amplitude extremes of a series of pulses in a train. The term "burst envelope" where used herein can refer to a curve outlining the amplitude extremes of a series of pulses in a burst. The term "train ramp duration" where used herein can refer to the time from the onset of a train until its train envelope reaches a desired target magnitude. The term "burst ramp duration" where used herein can refer to the time from the onset of a burst until its burst envelope reaches a desired target magnitude.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, such as to treat pain. The patient can comprise a human or other mammalian patient. The medical apparatus can comprise a stimulation apparatus. The medical apparatus can comprise an implantable system and an external system. The implantable system can comprise one or more similar and/or dissimilar implantable devices. Each implantable device comprises a housing surrounding one or more stimulation producing components. A lead comprising one or more stimulation elements can be pre-attached to the housing, or attachable to the housing (e.g. attached in a clinical procedure in which the implantable device is implanted in a patient).

The apparatus can include a trialing interface which provides energy to the stimulation elements during the implantation procedure (e.g. during a "trialing session" performed during the implantation procedure), such as to confirm proper placement of the stimulation elements and/or to titrate the stimulation delivered. In embodiments in which the lead is pre-attached to the housing of the implantable device, the trialing interface can be configured to provide power (e.g. wireless power) to the implantable device, the implantable device providing stimulation energy to the stimulation elements derived from the power provided by the trialing interface. In embodiments in which the lead is attachable to the housing of the implantable device, the trialing interface can attach to the lead (prior to its attachment to the housing of the implantable device), and the trialing interface can then provide the stimulation energy directly to the stimulation elements.

In some embodiments, the implantable system comprises a first implantable device that delivers stimulation energy via energy received wirelessly from one or more external devices, and a second implantable device that delivers stimulation energy via an integral (e.g. implanted) battery. In these embodiments, the first implantable device can be configured to deliver stimulation energy during a limited period of time (e.g. a trial period in which stimulation parameter settings are determined and/or acceptability of the apparatus is determined), and the second implantable device can be configured to deliver stimulation energy for a prolonged period of time in which long-term stimulation therapy is provided to a patient. In these embodiments, a single implantable lead comprising one or more stimulation energy delivery elements (e.g. electrodes) can be connected to the first implantable device and then the second implantable device. In some embodiments, a first implantable device can be configured to remain implanted in the patient for a limited period of time, such as to reduce cost of manufacture, and a second implantable device is configured for a longer implant life. The first implantable device can be used in a trialing procedure (also referred to as a "trialing session" herein) in which the stimulation apparatus is assessed for acceptable use (e.g. by the patient and/or clinician) and/or one or more stimulation parameter settings are optimized or otherwise determined.

Each implantable device can comprise one or more implantable antennas configured to receive power and/or data. Each implantable device can comprise an implantable receiver configured to receive the power and/or data from the one or more implantable antennas. Each implantable device can comprise one or more implantable functional elements (e.g. an implantable stimulation element). An implantable functional element can be configured to interface with the patient (e.g. interface with tissue of the patient or interface with any patient location). Alternatively or additionally, an implantable functional element can interface with a portion of an implantable device (e.g. to measure an implantable device parameter). In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g. patient physiologic or patient environment information).

Each implantable device can comprise an implantable controller configured to control (e.g. modulate power to, send a signal to, and/or receive a signal from) the one or more implantable functional elements. In some embodiments, an implantable controller of a first implantable device is configured to control one or more other implantable devices. Each implantable device can comprise an implantable energy storage assembly (e.g. a battery and/or a capacitor) configured to provide power to the implantable controller (e.g. a controller comprising a stimulation waveform generator), the implantable receiver and/or the one or more implantable functional elements. In some embodiments, an implantable energy storage assembly is further configured to provide power to an assembly that transmits signals via the implantable antenna (e.g. when the implantable device is further configured to transmit data to one or more external devices). Each implantable device can comprise an implantable housing surrounding the implantable controller and the implantable receiver. In some embodiments, one or more implantable antennas are positioned within the implantable housing. Alternatively or additionally, one or more implantable antennas and/or implantable functional elements can be positioned outside the implantable housing, and tethered (e.g. electrically tethered) to one or more electrical components of the implantable device positioned within the implantable housing. In some embodiments, one or more implantable functional elements are positioned on an implantable lead, such as a flexible lead mechanically fixed or attachable to the implantable housing and operably connected (e.g. electrically, fluidly, optically and/or mechanically) to one or more components internal to the implantable housing. The implantable lead can be inserted (e.g. tunneled) through tissue of the patient, such that its one or more functional elements are positioned proximate tissue to be treated and/or positioned at an area in which data is to be recorded. In some embodiments, the implantable lead is configured to operably attach to and/or detach from, multiple implantable devices.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external programmer configured to control the external transmitter and/or an implantable device (e.g. when an external power transmitter is not included in the apparatus or otherwise not present during use). Each external device can comprise an external housing that surrounds at least the external transmitter. In some embodiments, the external housing surrounds the one or more external antennas, the external power supply and/or the external programmer.

The external programmer can comprise a discrete controller separate from the one or more external devices, and/or a controller integrated into one or more external devices. The external programmer can comprise a user interface, such as a user interface configured to set, adjust, and/or otherwise modify one or more treatment and/or data recording settings of the medical apparatus of the present inventive concepts. In some embodiments, the external programmer is configured to collect and/or diagnose recorded patient information, such as to provide the information and/or diagnosis to a clinician of the patient, to a patient family member and/or to the patient themselves. The collected information and/or diagnosis can be used to modify treatment or other operating parameters of the medical apparatus. In some embodiments, at least two external programmers are included, such as a first external programmer configured for use by the patient, and a second external programmer configured for use by a clinician of the patient.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue" or "nervous system tissue"). The stimulation apparatus comprises an external system configured to transmit power, and an implanted system configured to receive the power from the external system and to deliver stimulation energy to tissue. The delivered stimulation energy can comprise one or more stimulation waveforms, such as a stimulation waveform configured to enhance treatment of pain while minimizing undesired effects. The stimulation signal (also referred to as "stimulation energy" herein) delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Referring now to FIG. 1, a schematic anatomical view of a stimulation apparatus for providing a therapy to a patient is illustrated, consistent with the present inventive concepts. Apparatus 10 comprises implantable system 20 and external system 50. External system 50 transmits transmission signals to one or more components of implantable system 20. These transmission signals can comprise power and/or data. Implantable system 20 comprises implantable device 200 shown implanted beneath the skin of patient P.

In some embodiments, implantable system 20 comprises multiple similar or dissimilar implantable devices 200 (singly or collectively implantable device 200), such as is described in applicant's co-pending U.S. patent application Ser. No. 17/372,095, titled "Apparatus with Enhanced Stimulation Waveforms", filed Jul. 9, 2021. Each implantable device 200 can be configured to receive power and data from a transmission signal transmitted by external system 50, such as when stimulation energy delivered to the patient (e.g. to nerve or other tissue of the patient) by implantable device 200 is provided via wireless transmissions signals from external system 50. In some embodiments, implantable system 20 comprises at least two implantable devices, such as implantable device 200 and implantable device 200' shown in FIG. 1. Implantable device 200' can be of similar construction and arrangement to implantable device 200, and it can include components of a different configuration. Each implantable device 200 comprises one or more housings, housing 210 shown, which surrounds various other components of device 200. Each implantable device 200 comprises one or more stimulation and/or other functional elements, such as stimulation element 260 shown, where stimulation elements 260 are configured to deliver stimulation energy, a stimulating drug or other agent, and/or another form of stimulation (e.g. another form of tissue stimulation) to the patient. In some embodiments, one or more stimulation elements 260 are further configured as a sensor (e.g. when comprising an electrode configured to both deliver electrical energy and record electrical signals). Each implantable device 200 can include one or more leads, lead 265 shown, and each lead 265 can include one or more stimulation elements 260. Alternatively or additionally, one or more stimulation elements 260 can be positioned on housing 210 or one or more other components of implantable device 200. Each lead can include one or more elements configured to anchor lead 265 to tissue, such as anchor element 221 shown. Anchor element 221 can be configured to slidingly receive the shaft of lead 265 (e.g. to position anchor element 221 about lead 265 in manufacturing and/or in an implantation procedure). Anchor element 221 can include one or more fixation points, such as one or more circumferential recesses. Surgical clips or sutures can be placed around a recess and into tissue, such as to fixate anchor element 221 and an inserted lead 265 to tissue.

Each implantable device 200 can comprise one or more other types of functional elements, such as functional element 299a shown positioned proximate housing 210 (e.g. within and/or on the external surface of housing 210) and/or functional element 299b shown positioned on lead 265. Functional element 299a and/or 299b (singly or collectively functional element 299) can comprise a transducer, a sensor, and/or other functional element as described herein. In some embodiments, a functional element 299 comprises a visualizable marker, such as a radiopaque marker, an ultrasonically visible marker, and/or a magnetic marker.

External system 50 can comprise an external device 500, which includes one or more housings, housing 510 shown, which surrounds various other components of device 500. In some embodiments, external system 50 comprises multiple external devices 500 (singly or collectively external device 500), such as an external device as is described in applicant's co-pending U.S. patent application Ser. No. 17/372, 095, titled "Apparatus with Enhanced Stimulation Waveforms", filed Jul. 9, 2021. In some embodiments, external system 50 comprises at least two, or at least three external devices (e.g. at least two external devices configured to deliver power and/or data to one or more implantable devices 200), such as external device 500, external device 500', and external device 500" shown in FIG. 1. External device 500' and/or 500" can be of similar construction and arrangement to external device 500, and these devices can include components of a different configuration.

External system 50 can comprise one or more programming devices, programmer 600, such as patient programmer 600' and clinician programmer 600" shown. Patient programmer 600' and clinician programmer 600" (singly or collectively programmer 600) each comprise a user interface, such as user interfaces 680' and 680" shown (singly or collectively user interface 680). Programmer 600 can be configured to control one or more external devices 500. Alternatively or additionally, programmer 600 can be configured to control one or more implantable devices 200 (e.g. when no external device 500 is included in apparatus 10 or at least no external device 500 is available to communicate with an implantable device 200). Patient programmer 600' can be configured to be used by the patient, patient caregiver (e.g. clinician of the patient), and/or a family member of the patient.

Clinician programmer 600" can be of similar construction and arrangement to patient programmer 600'. In some embodiments, clinician programmer 600" provides additional functions not available using patient programmer 600'. In some embodiments, clinician programmer 600" can modify the programming of patient programmer 600' (e.g. modify the programming options available to the patient or family member of the patient).

Patient programmer 600' can be further configured as a smart phone and/or a music playing device (e.g. an mp3 player). For example, patient programmer 600' can comprise a smart phone or other commercial device onto which a software program of apparatus 10 is embedded to cause the commercial device to function as patient programmer 600'. Clinician programmer 600" can comprise a tablet-like device. For example, clinician programmer 600" can comprise a commercial tablet device onto which a software program of apparatus 10 is embedded to cause the commercial tablet to function as clinician programmer 600".

Clinician programmer 600" can configure multiple (e.g. all) external devices 500 used by a patient, as well as patient programmer 600', so that the set of devices are configured as a "trusted" network. After this configuration, patient programmer 600' can safely and effectively communicate with the one or more external devices 500 of the patient. The patient programmer 600' can upload (e.g. automatically upload) configuration information from an external device 500 (e.g. stimulation parameter settings and the like). In some embodiments, patient programmer 600' and/or clinician programmer 600" uploads configuration information from an external device 500 any time certain information (e.g. stimulation information) on that external device 500 has changed (e.g. a change is detected by the programmer 600 or otherwise).

External system 50 can comprise one, two, three, or more functional elements, such as functional elements 599a, 599b, and/or 599c (singly or collectively functional element 599), shown positioned in external device 500, patient programmer 600', and clinician programmer 600", respectively.

Apparatus 10 can be configured to stimulate tissue (e.g. stimulate nerve tissue such as tissue of the central nervous system or tissue of the peripheral nervous system, such as to neuromodulate nerve tissue), such as by having one or more implantable devices 200 deliver and/or otherwise provide energy (hereinafter "deliver energy") and/or deliver an agent (e.g. a pharmaceutical compound or other agent) to one or more tissue locations, such as via one or more stimulation elements 260. In some embodiments, one or more implantable devices 200 deliver energy and/or an agent while receiving power and/or data from one or more external devices 500. In some embodiments, one or more implantable devices 200 deliver energy and/or an agent (e.g. continuously or intermittently) using energy provided by an internal power source (e.g. a battery and/or capacitor) without receiving externally supplied power, such as for periods of at least 1 hour, at least 1 day, at least 1 month or at least 1 year. In some embodiments, one or more stimulation parameters are varied (e.g. systematically and/or randomly), during that period.

In some embodiments, apparatus 10 is further configured as a patient diagnostic apparatus, such as by having one or more implantable devices 200 record a patient parameter (e.g. a patient physiologic parameter) from one or more tissue locations, such as while receiving power and/or data from one or more external devices 500. In some embodiments, during its use, one or more implantable devices 200 at least receives power from one or more external devices 500 (e.g. with or without also receiving data). Alternatively or additionally, one or more patient parameters can be recorded by an external device of apparatus 10, such as via a programmer 600 and/or an external device 500.

Apparatus 10 can be configured as a patient information recording apparatus, such as by having one or more implantable devices 200 and/or one or more external devices 500 record patient information (e.g. patient physiologic information and/or patient environment information). In some embodiments, one or more implantable devices 200 and/or one or more external devices 500 further collect information (e.g. status information or configuration settings) of one or more of the components of apparatus 10.

In some embodiments, apparatus 10 is configured to deliver stimulation energy to tissue to treat pain. In particular, apparatus 10 can be configured to deliver stimulation energy to tissue of the spinal cord and/or tissue associated with the spinal cord ("tissue of the spinal cord", "spinal cord tissue" or "spinal cord" herein), the tissue including roots, dorsal root, dorsal root ganglia, spinal nerves, ganglia, and/or other nerve tissue. The delivered energy can comprise energy selected from the group consisting of: electrical energy; magnetic energy; electromagnetic energy; light energy such as infrared light energy, visible light energy and/or ultraviolet light energy; mechanical energy; thermal energy such as heat energy and/or cryogenic energy; sound energy such as ultrasonic sound energy (e.g. high intensity focused ultrasound and/or low intensity focused ultrasound) and/or subsonic sound energy; chemical energy; and combinations of one or more of these. In some embodiments, apparatus 10 is configured to deliver to tissue energy in a form selected from the group consisting of: electrical energy such as by providing a controlled (e.g. constant or otherwise controlled) electrical current and/or voltage to tissue; magnetic energy (e.g. magnetic field energy) such as by applying controlled current or voltage to a coil or other magnetic field generating element positioned proximate tissue; and/or electromagnetic energy such as by providing both current to tissue and a magnetic field to tissue. A coil or other magnetic field generating element can surround (e.g. at least partially surround) the target nerve. Alternatively, or additionally, the magnetic energy can be applied externally and focused to specific target tissue via an implant comprising a coil and/or ferromagnetic materials. In some embodiments, the magnetic energy is configured to induce the application of mechanical energy. Delivered energy can be supplied in one or more stimulation waveforms, each waveform comprising one or more pulses of energy, as described in detail herebelow.

In some embodiments, apparatus 10 is configured as a stimulation apparatus in which external system 50 transmits a power signal to one or more implantable devices 200, and the one or more implantable devices 200 deliver stimulation energy to tissue with a stimulation signal (also referred to as a stimulation waveform), with the power signal and the stimulation signal having one or more different characteristics (e.g. as described herebelow). The power signal can be modulated with data (e.g. configuration or other data to be sent to one or more implantable devices 200). In these embodiments, the characteristics of the stimulation signal delivered (e.g. amplitude, frequency, duty cycle and/or pulse width), can be independent (e.g. partially or completely independent) of the characteristics of the power signal transmission (e.g. amplitude, frequency, phase, envelope, duty cycle and/or modulation). For example, the frequency and modulation of the power signal can change without affecting those or other parameters of the stimulation signal, and/or the parameters of the stimulation signal can be changed (e.g. via programmer 600), without requiring similar or any changes to the power signal. In some embodiments, implantable system 20 is configured to rectify the received power signal, and to produce a stimulation waveform with entirely different characteristics (e.g. amplitude, frequency and/or duty cycle) from the rectified power signal. Each implantable device 200 can comprise an oscillator and/or controller configured to produce the stimulation signal. In some embodiments, one or more implantable devices 200 is configured to perform frequency multiplication, in which multiple signals are multiplexed, mixed, added, and/or combined in other ways to produce a broadband stimulation signal.

In some embodiments, apparatus 10 is configured such that external system 50 transmits data (e.g. data and power) to implantable system 20, and implantable system 20 recovers (e.g. decodes, demodulates or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL); phase locked loop (PLL); high frequency clock; and/or crystal oscillator needed to perform the synchronization. Avoiding these components can also be correlated to reduced package size of each implantable device 200 (e.g. avoidance of a relatively large sized crystal oscillator). Asynchronous data transfer between external system 50 and implantable system 20 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591,188, titled "Method of Making and Using an Apparatus for a Locomotive Micro-Implant using Active Electromagnetic Propulsion", filed Aug. 21, 2012. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013.

Apparatus 10 can be configured to treat pain, such as back pain and/or limb pain treated by stimulating dorsal root ganglia and/or other nerves or locations of the spinal cord or other nervous system locations. In some embodiments, apparatus 10 is configured to treat a type of pain selected from the group consisting of: back pain; joint pain; neuropathic pain; tennis elbow; muscle pain; shoulder pain; chronic, intractable pain of the back and/or limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these.

In some embodiments, apparatus 10 is configured to treat a patient disease or disorder selected from the group consisting of: chronic pain; acute pain; migraine; cluster headaches; urge incontinence; pelvic dysfunction such as overactive bladder; fecal incontinence; bowel disorders; tremor; obsessive compulsive disorder; depression; epilepsy; inflammation; tinnitus; hypertension; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

In some embodiments, apparatus 10 is configured to treat one or more diseases or disorders by delivering stimulation to perform renal modulation. In some embodiments, apparatus 10 is configured to treat hypertension, such as when apparatus 10 is configured to deliver stimulation to perform renal neuromodulation.

Apparatus 10 can be configured to treat heart disease, such as heart failure of a patient. In these embodiments, stimulation of the spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more stimulation elements 260 of one or more implantable devices 200 can be implanted at one or more spinal cord locations, such as to deliver stimulation to tissue proximate those locations. In some embodiments, stimulation elements 260 comprise two or more stimulation elements (e.g. electrodes) that span multiple vertebra of the spinal column (e.g. multiple stimulation elements that span at least T-8 to T-9 and/or T-9 to T-10). Power and/or data can be transmitted to the one or more implantable devices 200 via one or more external devices 500 of external system 50. One or more stimulation signals can be delivered to spinal cord tissue, such as to treat heart failure or other cardiac disease or disorder. In some embodiments, one or more stimulation elements 260 are configured to deliver energy (e.g. electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g. one or more stimulation elements 260, functional elements 299, functional elements 599 and/or other functional elements of implantable system 20) are configured (e.g. further configured) to record a patient parameter (e.g. stimulation element 260, functional element 299, functional element 599, and/or another functional element of apparatus 10 are configured as a sensor), such as a patient heart or spine parameter, and the information recorded is used to modify the delivered stimulation signals. The at least one heart parameter can comprise a parameter selected from the group consisting of: EKG; blood oxygen; blood pressure; heart rate; ejection fraction; wedge pressure; cardiac output; and combinations of one or more of these.

Apparatus 10 can be configured to pace and/or defibrillate the heart of a patient. One or more stimulation elements 260 can be positioned proximate cardiac tissue and deliver a stimulation signal as described herein (e.g. based on power and/or data received by implantable system 20 from external system 50). The stimulation signal can be used to pace, defibrillate and/or otherwise stimulate the heart. Alternatively or additionally, apparatus 10 can be configured to record cardiac activity (e.g. by recording EKG, blood oxygen, blood pressure, heart rate, ejection fraction, wedge pressure, cardiac output, lung impedance and/or other properties or functions of the cardiovascular system via a sensor-based element 260, and/or other sensor of apparatus 10), such as to determine an onset of cardiac activity dysfunction or other undesired cardiac state. In some embodiments, apparatus 10 is configured to both record cardiac or other information and deliver a stimulation signal to cardiac tissue (e.g. stimulation varied or otherwise based on the recorded information). For example, apparatus 10 can be configured such that external system 50 transmits power and/or data to implantable system 20, and implantable system 20 can monitor cardiac activity, and upon detection of an undesired cardiovascular state, implantable system 20 delivers a pacing and/or defibrillation signal to the tissue that is adjacent to one or more stimulation elements 260 configured to deliver a cardiac stimulation signal.

Apparatus 10 can be configured to perform a diagnostic procedure including measuring one or more patient parameters (e.g. patient physiologic or other patient parameters), such as are described in detail herebelow. In some embodiments, apparatus 10 is configured to measure a physiologic parameter that can be sensed from one or more sensor-based stimulation elements 260, functional elements 299, and/or functional elements 599 positioned in subcutaneous tissue. In these embodiments, external system 50 can comprise an external device 500 configured for placement proximate an implantable device 200 implanted in a position to record data from subcutaneous tissue (e.g. blood glucose data). External device 500 can comprise a wrist band, a wristwatch, and/or an arm band configuration such as when the implantable device 200 is positioned in subcutaneous tissue proximate the patient's wrist or upper arm. The external device 500 can comprise a leg, knee or ankle band configuration, such as when one or more implantable devices 200 are positioned in subcutaneous tissue proximate the patient's ankle, knee, and/or thigh. In some embodiments, external device 500 comprises a band or other attachment device for positioning about the thorax, neck, groin, and/or head of the patient. Power and/or data can be sent to the implantable device 200 from the external device 500, and data (e.g. blood glucose data) can be sent to external device 500 (or another component of external system 50) by implantable device 200, such as using a wireless communication configuration known to those of skill in the art. In some embodiments, external system 50 comprises a functional element 599 (e.g. functional element 599*a*, 599*b*, and/or 599*c*) configured to deliver an agent (e.g. insulin or glucose delivered by a needle-based functional element 599), based on the information received from implantable device 200. Alternatively, or additionally, implantable device 200 comprises a stimulation element 260 configured to deliver an agent (e.g. insulin or glucose delivered by a needle-based stimulation element 260), based on the information recorded by implantable device 200. Various closed loop sensing and agent delivery combinations and configurations should be considered within the spirit and scope of the present inventive concepts, including but not limited to: sensing a blood parameter such as white blood cell count and delivering a chemotherapeutic or other agent based on the blood parameter;

sensing a hormone level and delivering a hormone or a hormone affecting agent; sensing blood pressure and delivering stimulation energy and/or a blood pressure affecting agent; sensing neural activity and delivering stimulation energy and/or a neural affecting agent or other agent based on the neural activity, such as for treating epilepsy; and combinations of one or more of these.

As described hereabove, external system 50 can be configured to transmit power and/or data (e.g. implantable system 20 configuration data) to one or more implantable devices 200 of implantable system 20. Implantable system 20 configuration data provided by external system 50 (e.g. via one or more antennas, antenna 540 shown, of one or more external devices 500) can include when to initiate stimulation delivery (e.g. energy delivery), and/or when to stop stimulation delivery, and/or it can include data related to the value or change to a value of one or more stimulation parameters as described hereabove. The configuration data can include a stimulation parameter such as an agent (e.g. a pharmaceutical agent) delivery stimulation parameter selected from the group consisting of: initiation of agent delivery; cessation of agent delivery; amount of agent to be delivered; volume of agent to be delivered; rate of agent delivery; duration of agent delivery; time of agent delivery initiation; and combinations of one or more of these. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

As described hereabove, external system 50 can comprise one or more external devices 500. External system 50 can comprise one or more antennas 540, such as when a single external device 500 comprises one or more antennas 540, and/or when multiple external devices 500 each comprise one or more antennas 540. The one or more antennas 540 can transmit power and/or data to one or more antennas 240 of implantable system 20, such as when a single implantable device 200 comprises one or more antennas 240, and/or when multiple implantable devices 200 each comprise one or more antennas 240. In some embodiments, one or more antennas 540 define a radiation footprint (e.g. a footprint defining a volume, such as a volume of tissue, in which electromagnetic transmissions radiated by antennas 540 can be properly received by antennas 240), such as is described in applicant's co-pending U.S. patent application Ser. No. 17/412,044, titled "Medical Apparatus Including an Implantable System and an External System", filed Aug. 25, 2021.

External system 50 transmits power and/or data with a transmission signal comprising at least one wavelength, $\lambda$. External system 50 and/or implantable system 20 can be configured such that the distance between an external antenna 540 transmitting the power and/or data and one or more implantable antennas 240 receiving the power and/or data transmission signal is equal to between $0.1\lambda$ and $10.0\lambda$, such as between $0.2\lambda$, and $2.0\lambda$. In some embodiments, one or more transmission signals are delivered by a transmitter, transmitter 530, at a frequency range between 10 MHz and 10.6 GHz, such as between 0.1 GHz and 10.6 GHz, between 10 MHz and 3.0 GHz, between 40 MHz and 1.5 GHz, between 10 MHz and 100 MHz, between 0.902 GHz and 0.928 GHz, in a frequency range proximate to 40.68 MHz, in a frequency range proximate to 866 MHz, or approximately between 863 MHz and 870 MHz. Transmitter 530 can comprise a transmitter that produces a transmission signal with a power level between 0.01 W and 4.0 W, such as a transmission signal with a power level between 0.01 W and 2.0 W or between 0.2 W and 1.0 W.

In addition to transmitting power and/or data to implantable system 20, external system 50 can be further configured to provide information (e.g. patient information and/or apparatus 10 performance information) to one or more other components of apparatus 10, such as tool 60 shown in FIG. 1 and described in detail herebelow.

One or more external devices 500 (singly or collectively external device 500) can be configured to transmit power and/or data (e.g. implantable system 20 configuration data) to one or more implantable devices 200 (singly or collectively implantable device 200). In some embodiments, one or more external devices 500 are configured to transmit both power and data (e.g. simultaneously and/or sequentially) to one or more implantable devices 200. In some embodiments, one or more external devices 500 are further configured to receive data from one or more implantable devices 200 (e.g. via data transmitted by one or more antennas 240 of one or more implantable devices 200). Each external device 500 can comprise housing 510, power supply 570, a transmitter 530, a controller 550, and/or one or more antennas 540, each shown in FIG. 1 and described in detail herebelow. Each external device 500 can further comprise one or more functional elements 599*a*, such as a functional element comprising a sensor, electrode, energy delivery element, a magnetic-field-generating transducer, and/or any transducer, also described in detail herebelow. In some embodiments, a functional element 599*a* comprises one or more sensors configured to monitor performance of external device 500 (e.g. to monitor voltage of power supply 570, quality of transmission of power and/or data to implantable system 20, temperature of a portion of an external device 500, and the like).

One or more housings 510 (singly or collectively housing 510) of each external device 500 can comprise one or more rigid and/or flexible materials which surround various components of external device 500 such as antenna 540, transmitter 530, controller 550, and/or power supply 570 shown in FIG. 1. In some embodiments, a single external device 500 comprises multiple discrete (i.e. separate) housings 510, two or more of which can each transfer data and/or other signals via a wired or wireless connection to the other, to an implantable device 200, and/or to another component of apparatus 10. In some embodiments, a housing 510 further surrounds a programmer 600 (e.g. programmer 600' or 600") and/or a power supply 570. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g. shielded to prevent transmission of electromagnetic waves), and an unshielded portion, such as an unshielded portion surrounding antenna 540.

Housing 510 can comprise an adhesive element (e.g. a spacer 511 configured as an adhesive element), such as an adhesive element configured to temporarily attach an external device 500 to the patient's skin. Alternatively or additionally, housing 510 can be constructed and arranged to engage (e.g. fit in the pocket of) a patient attachment device, such as patient attachment device 70 described herebelow.

One or more antennas 540 (singly or collectively antenna 540) can each comprise one, two, three, or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240, such as to adjust for movement of the array of the antennas 540 relative to the implanted antennas 240. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material. For antenna 540 to operate effectively at higher frequencies, the shield material can comprise a ferrite material that has a low conductivity and low magnetic loss tangent at a frequency of interest, and whereby a higher permeability is achieved. By placing a material with a high magnetic permeability ($\mu'$), low magnetic loss tangent ($\mu''/\mu'$), and low conductivity at the operating frequency (such as a high frequency ferrite) between the antenna and other elements of the transmitter, the losses or loading effects due to these elements can be dramatically reduced. In some cases, the magnetic field magnification of this shielding layer will enhance the overall performance Additionally, this layer shields the outside environment from unwanted radiation from the antenna, and it protects the antenna from radiation originating in the environment.

In some embodiments, a spacing layer is positioned between antenna 540 and the shield material. The spacing layer can comprise a thickness of between 0 mm and 5 mm, such as between 0.25 mm and 1 mm. The spacing layer can comprise non-conductive dielectric materials, air, or other materials that have minimal impact on antenna performance. The spacing layer can also be incorporated into a board thickness, with the antenna being constructed on the opposite side of the board in relation to the shielding layer. The shielding layer can comprise a ferrite material as described hereabove, or any material with the desired permeability, magnetic loss, and conductivity at the frequency of interest. The thickness of the shielding layer can be dependent on its specific material properties and the application. In some embodiments, a conductive layer on the side of the shielding layer is positioned opposite the antenna to further shield unwanted radiation. To reduce weight, the shielding layer material can be porous or incorporate holes or slots spaced in a way to minimize the reduction in performance. The holes and spacings can be sized smaller than a wavelength of the RF signal. If no spacing layer is used, the shielding layer can extend inside the antenna. Additionally or alternatively, the shielding layer can be positioned on the other side or both sides of the antenna because of the field magnification effect. In some embodiments, the shielding layer is constructed to increase the directivity of the antenna or focus the electromagnetic energy.

One or more antennas 540 can be positioned in a housing 510 that is otherwise void of other components (e.g. void of power supply 570, controller 550 and/or transmitter 530), such as when an antenna 540 is positioned within a first housing 510 and communicates with components positioned in a second housing 510.

In some embodiments, one or more spacers, spacer 511 shown, is positioned between antenna 540 and the patient's skin, such as a spacer comprising a thickened portion of housing 510 or a discrete spacer 511 placed on a side of housing 510 (as shown) or on a side of antenna 540. Spacer 511 can comprise one or more materials that match the impedance of antenna 540 to the impedance of the patient's tissue. Spacer 511 can comprise a thickness of between 0.1 cm to 3 cm, such as a thickness between 0.2 cm and 1.5 cm. Spacer 511 can comprise materials which isolate heat (e.g. a spacer 511 comprising thermally insulating material). Alternatively, or additionally, housing 510 can comprise a heat insulating and/or dissipating material. Spacer 511 can comprise a soft or otherwise compressible material (e.g. foam) for patient comfort. Spacer 511 can be inflatable, such as to control the separation distance of an external antenna 540 from the patient's skin. An inflatable spacer 511 can be compartmentalized into several sections with independently controlled air pressure or volume to adjust the separation distance of an external antenna 540 and the patient's skin and/or its angle (e.g. tilt) with respect to the tissue surface.

In some embodiments, antenna 540 comprises a multi-feed point antenna, such as a multi-feed point antenna configured to: support beam shaping and/or focusing; allow modification of amplitude and/or phase of a transmission signal; increase the radiation footprint; and combinations of one or more of these.

In some embodiments, antenna 540 comprises one or more antennas selected from the group consisting of: patch antenna; slot antenna; array of antennas; a loop antenna (e.g. a concentric loop antenna); antenna loaded with reactive elements; dipole antenna; polarizable antenna; selectable conductors that form an antenna; and combinations of one or more of these.

Antenna 540 can comprise a major axis between 1 cm and 10 cm, such as a major axis between 2 cm and 5 cm, and/or a major axis of approximately 4 cm. Antenna 540 can be further configured to receive a signal, such as when an antenna 240 is configured to transmit data to an external device 500. Antenna 540 can be positioned on (e.g. fabricated onto) a substrate, such as a flexible printed circuit board or other printed circuit board (e.g. a single or multiple layer printed circuit board comprising electrical traces connecting components).

A single external antenna 540 can be configured to transmit power and/or data to multiple implantable devices 200 (e.g. each containing one or more antennas 240). In some embodiments, a single external device 500, comprising one or more antennas 540 can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g. within housing 510). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200 operation depth; polarization; power efficiency; a radiation footprint; directional gain; beam shaping and/or focusing; sensitivity to implantable device 200 placement; patient comfort; patient usability; data transfer; and combinations of one or more of these. In some embodiments, the first antenna 540 is optimized for a different design parameter than the second antenna 540, and each antenna 540 can be activated independently or simultaneously to realize both benefits. In some embodiments, the first antenna 540 is similar to the second antenna 540 and placed in an array to increase the radiation footprint or placed in different external locations to operate with multiple implantable devices 200 implanted at different sites.

In some embodiments, a first external antenna 540 and a second external antenna 540 transmit power and/or data to a single implantable antenna 240. In some embodiments, a first antenna 540 and a second antenna 540 transmit power and/or data to one or more antennas 240, the transmissions performed simultaneously or sequentially. In sequential power and/or data transfers, a first external device 500 comprising a first one or more antennas 540 can be replaced (e.g. swapped) with a second external device 500 comprising a second one or more antennas 540. Alternatively or additionally, sequential power and/or data transfer can be initiated by one or more of the following conditions: when a first external antenna 540 moves (e.g. moves relative to an implanted antenna 240); when a second external device 500 comprising a second antenna 540 is turned on or otherwise activated; when a second antenna 540 provides improved power and/or data transfer to antenna 240 than that which is provided by a first antenna 540; and/or when power received from a first antenna 540 decreases (e.g. decreases below a threshold). In some embodiments, an antenna 240 receives power from a first antenna 540 and a second antenna 540, but only receives data from the first antenna 540. In some embodiments, a first antenna (e.g. an antenna 240 or an antenna 540) is driven with a different carrier signal than a second antenna (e.g. an antenna 240 or an antenna 540). The two carrier signals can comprise differences in amplitudes and/or relative phases as compared to each other. Each carrier signal can include a data transmission signal (e.g. data to be transmitted to an implantable device 200 from an external device 500 or to an external device 500 from an implantable device 200).

External device 500 can comprise an electronics module, controller 550 shown, configured to control one or more other components of external device 500. Controller 550 can comprise one or more electronic elements, electronic assemblies, and/or other electronic components, such as components selected from the group consisting of: memory storage components; analog-to-digital converters; rectification circuitry; state machines; microprocessors; microcontrollers; filters and other signal conditioners; sensor interface circuitry; transducer interface circuitry; and combinations thereof. In some embodiments, controller 550 comprises a memory storage component that includes instructions, such as instructions used by controller 550 to produce a stimulation waveform and/or perform an algorithm, each as described herein.

One or more transmitters 530 (singly or collectively external transmitter 530) can each comprise one or more external transmitters that drive one or more antennas 540 (e.g. one or more antennas 540 positioned in a single external device 500 or multiple external devices 500). Transmitter 530 is operably attached to antenna 540 and is configured to provide one or more drive signals to antenna 540, such as one or more power signals and/or data signals transmitted to one or more implantable devices 200 of implantable system 20. Transmitter 530 can be configured to perform multi-level amplitude shift keying. The amplitude shift-keying can be configured to provide adjustable-depth modulation between 0-100% depth, such as between 5-75% depth, or such as between 10-50% depth.

As described herein, one or more external devices 500 can be configured to transmit data (e.g. configuration data) to one or more implantable devices 200, such as via a data transmission produced by transmitter 530 and sent to one or more antennas 540. In some embodiments, a transmitter 530 is configured to perform data modulation comprising amplitude shift keying with pulse width modulation. In these embodiments, the transmitter can be configured to perform multi-level amplitude shift keying. The amplitude shift-keying can be configured to provide adjustable-depth modulation between 0-100% depth, such as between 5-75% depth, or such as between 10-50% depth. In some embodiments, one or more external devices 500 transmit data to one or more implantable devices 200 using time division multiple access (TDMA). In some embodiments, one or implantable devices 200 are independently addressable through unique identification (ID) codes. Alternatively or additionally, transmitter 530 can be configured to transmit one or more data signals with a bandwidth between 1 kHz and 100 MHz, between 0.1 MHz and 100 MHz, or between 1 MHz and 26 MHz.

As described herein, one or more external devices 500 can be configured to transmit power to one or more implantable devices 200, such as via a power transmission produced by transmitter 530 and set to one or more antennas 540. One or more transmitters 530 can deliver power to one or more implantable devices 200 simultaneously or sequentially. In some embodiments, one or more transmitters 530 are configured to modify the level of power transmitted to one or more implantable devices 200, such as by modifying one or more duty cycling parameters. In these embodiments, power transmitted can be modified to: set a power transfer based on a stimulation level produced by implantable system 20; prevent oversaturation; to reduce interference with implantable system 20 data transmissions (e.g. when one or more implantable devices 200 are further configured to transmit data to external system 50); set a power transfer based on charge information and/or discharge information related to an implantable device 200 (e.g. charge rate and/or discharge rate of implantable energy storage assembly 270 described herebelow); and combinations of one or more of these. In some embodiments, implantable system 20 comprises a first receiver 230 (e.g. of a first implantable device 200) and a second receiver 230 (e.g. of a second implantable device 200'). One or more transmitters 530 can be configured to transmit a first power transmission to the first receiver 230, and a second power transmission to the second receiver 230. The first power transmission and the second power transmission can be modified or otherwise be different, such as to prevent oversaturation.

In some embodiments, transmitter 530 (and/or another component of external system 50) is further configured as a receiver (e.g. can further include a receiver, in addition to a transmitter or include a transmitter that further functions as a receiver), such as to receive data from implantable system 20. For example, a transmitter 530 can be configured to receive data via one or more antennas 240 of one or more implantable devices 200. Data received can include patient information (e.g. patient physiologic information, patient environment information or other patient information) and/or information related to an implantable system 20 parameter (e.g. an implantable device 200 stimulation parameter and/or another configuration parameter as described herein).

In some embodiments, transmitter 530 comprises a first transmitter to transmit power and/or data to one or more implantable devices 200, and a second transmitter to transmit data to a different device, as described herein. In these embodiments, a second transmitter of transmitter 530 can be configured to transmit data to tool 60 or another device such as a programmer 600; cell phone; computer; tablet; computer network such as the internet or a LAN; and combinations of one or more of these. In some embodiments, the second transmitter of transmitter 530 comprises a wireless transmitter; a Bluetooth transmitter; a cellular transmitter; and combinations of one or more of these. In some embodiments, a functional element 599 comprises a transmitter such as a Bluetooth transmitter.

Each power supply 570 (singly or collectively power supply 570) can be operably attached to a transmitter 530, and one or more other electrical components of each external device 500. Power supply 570 can comprise a power supplying and/or energy storage element selected from the group consisting of: battery; replaceable battery (e.g. via a battery door of housing 510); rechargeable battery; AC power converter; capacitor; and combinations of one or more of these. In some embodiments, power supply 570 comprises two or more batteries, such as two or more rechargeable batteries, such as to allow the first battery to be replaced (e.g. serially replaced) by the second battery (e.g. external device 500 can function with a single battery). In some embodiments, power supply 570 is configured to provide a voltage of at least 3V. In some embodiments, power supply 570 is configured to provide a capacity between 1 Watt-hour and 75 Watt-hours, such as a battery or capacitor with a capacity of approximately 5 Watt-hours. In some embodiments, power supply 570 comprises an AC power source. Power supply 570 can include voltage and/or current control circuitry. Alternatively or additionally, power supply 570 can include charging circuitry, such as circuitry configured to interface a rechargeable battery with an external charging device. In some embodiments, apparatus 10 includes one or more charging devices, charger 61 shown, which can be configured to recharge a component of apparatus 10, such as to recharge power supply 570 of one or more external devices 500.

Each external device 500 can include one or more user interface components, user interface 580 shown, such as to allow the patient or other user to enter, adjust and/or otherwise modify ("enter", "adjust", and/or "modify" herein) one or more parameters of apparatus 10 (e.g. one or more variable stimulation parameters of apparatus 10). User interface 580 can include one or more user input components (e.g. buttons, slides, knobs, and the like) and/or one or more user output components (e.g. lights, displays and the like). In some embodiments, user interface 580 includes one or more controls configured to provide a water-ingress-resistant barrier.

Each patient programmer 600' or clinician programmer 600" (singly or collectively programmer 600) comprises a programming device configured to control one or more components of apparatus 10. Programmer 600 can comprise a user interface 680. Programmer 600 can send and/or receive commands to and/or from one or more external devices 500 via a wireless or wired connection (wired connection not shown but such as one or more insulated conductive wires). In some embodiments, one or more external devices 500 comprise all or a portion of programmer 600, such as when all or a portion of user interface 680 is integrated into housing 510 of external device 500. In some embodiments, apparatus 10 comprises multiple programmers 600, such as one or more patient programmers 600' and/or one or more clinician programmers 600".

Programmer 600 can be configured to modify one or more parameters of apparatus 10, such as a stimulation parameter (e.g. a stimulation waveform parameter as described herein); a sensing parameter; a therapy parameter; a data recording parameter (e.g. a patient data recording parameter and/or an implantable device 200 data recording parameter); power transfer; data rate; activity of one or more external transmitters 530; activity of one or more external antennas 540; a stimulation element 260 parameter; a functional element 299 and/or 599 parameter; and combinations of one or more of these, such as is described hereabove. Programmer 600 can be further configured to provide information, such as patient physiologic information recorded by apparatus 10 (e.g. by one or more implantable devices 200 and/or one or more external devices 500), or apparatus 10 information, such as performance and/or configuration information (singly or collectively "status information") of one or more components of apparatus 10 (e.g. one or more external devices 500 and/or implantable devices 200). In some embodiments, programmer 600 uses information recorded by one or more implantable devices 200, apparatus 10 information, and/or information from external devices 500 to adapt configuration parameters of one or more components of apparatus 10.

In some embodiments, programmer 600 is configured to confirm that an adequate power transmission and/or an adequate data transmission has occurred between one or more external devices 500 and one or more implantable devices 200. In these embodiments, programmer 600 can comprise diagnostic assembly 62 described herebelow, or otherwise be configured to detect one or more of: power transmission to the implantable system 20 (e.g. to detect power transmission to implantable system 20 below a threshold); power transmission to the implantable system 20 trending in an undesired direction; improper and/or inadequate data transfer to the implantable system 20; and combinations of one or more of these. In some embodiments, programmer 600 monitors power transfer in real time and modifies power transmission accordingly to optimize the rectifier efficiency (e.g. efficiency of rectifier 232 described herebelow) of one or more implantable devices 200. In some embodiments, apparatus 10 can be configured to modify (e.g. in real time) the power transmission from one or more external devices 500 of external system 50 to one or more implantable devices 200 of implantable system 20, such as to optimize or otherwise improve an efficiency of apparatus 10, such as to improve the efficiency of transmissions between an external device 500 and an implantable device 200. These modifications can include modification of one or more of: power transmission amplitude, duty cycle, frequency, phase, and periodicity.

In some embodiments, programmer 600 and/or another component of apparatus 10 comprises a matching network configured to match the impedance of one or more antennas 540 to one or more transmitters 530. The matching network can comprise an adjustable matching network. The matching network can comprise a directional coupler configured to measure a reflection coefficient. A transmitter 530 can comprise an output, and a programmer 600 can be configured to monitor a standing wave pattern at the output of the transmitter 530.

In some embodiments, programmer 600 comprises a lookup table of stimulation signal waveform patterns, such as to allow a clinician, patient and/or other operator ("user" or "operator" herein) of apparatus 10 to view and/or select a predetermined stimulation pattern (e.g. using user interface 680). In some embodiments, programmer 600 comprises a set of adjustable stimulation signal parameters configured to be varied to allow an operator to construct customized waveforms, such as to vary one or more stimulation parameters described hereabove. In some embodiments, programmer 600 is configured to allow an operator to create a customized waveform by specifying an amplitude of one or more discrete pulses or steps of a stimulation signal. In some embodiments, a clinician programmer 600" can include stimulation waveform customization options not provided by a patient programmer 600'.

In some embodiments, programmer 600 comprises a transmitter configured to transmit data to tool 60 or another device such as a cell phone; computer; tablet; computer network such as the internet or a LAN; and combinations of one or more of these. In these embodiments, programmer 600 can comprise a wireless transmitter; a Bluetooth transmitter; a cellular transmitter; and combinations of one or more of these. In some embodiments, programmer 600 comprises a receiver configured to receive data, or a transceiver configured to both transmit and receive data.

User interface 680 of programmer 600 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 599, such as functional elements 599a, 599b, and/or 599c, shown positioned in external device 500, programmer 600', and in programmer 600", respectively. Each functional element 599 can comprise a functional element as defined hereabove (e.g. a sensor, a transducer, and/or other functional element as described herein). In some embodiments, a functional element 599 comprises a needle, a catheter (e.g. a distal portion of a catheter), an iontophoretic element or a porous membrane, such as an agent delivery element configured to deliver one or more agents contained (e.g. one or more agents in a reservoir, such as reservoir 525 described herebelow) within an external device 500 and delivered into the patient (e.g. into subcutaneous tissue, into muscle tissue and/or into a blood vessel such as a vein).

In some embodiments, the functional element 599 comprises an electrode for sensing electrical activity and/or delivering electrical energy. In some embodiments, apparatus 10 is configured to cause stochastic resonance, and the addition of white noise can enhance the sensitivity of nerves to be stimulated and/or boost weak signals to be recorded by the one or more stimulation elements 260.

In some embodiments, one or more functional elements 599 comprise a sensor, such as a sensor configured to record data related to a patient parameter (e.g. a patient physiologic parameter), an external system 50 parameter and/or an implantable system 20 parameter. In some embodiments, operation of one or more implantable devices 200 (e.g. stimulation energy delivered by one or more implantable devices 200) is configured to be delivered based on the data recorded by one or more sensor-based functional elements 599, such as in a closed-loop energy delivery mode.

Functional element 599 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature; inflammation level; bacteria level; type of bacteria present; gas level; blood gas level; neural activity; neural spikes; neural spike shape; action potential; local field potential (LFP); EEG; muscular activity (e.g. as measured using electromyography, EMG); electrical activity produced by skeletal muscles (e.g. as measured using EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 599 can comprise one or more sensors configured to record data representing a parameter of external system 50 or any component of apparatus 10. Functional element 599 can comprise one or more sensors selected from the group consisting of: an energy sensor; a voltage sensor; a current sensor; a temperature sensor (e.g. a temperature of one or more components of external device 500 or programmer 600); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via controller 250 described herebelow) the data recorded by functional element 599 to assess one or more of: power transfer; link gain; power use; energy within power supply 570; performance of power supply 570; expected life of power supply 570; discharge rate of power supply 570; ripple or other variations of power supply 570; matching of antennas 240 and 540; communication error rate between implantable device 200 and external device 500; integrity of transmission between implantable device 200 and external device 500; and combinations of one or more of these.

In some embodiments, one or more functional elements 599 are positioned on a housing 510. A functional element 599 can comprise a body conduction sensor, such as a body conduction sensor configured to record and/or receive data via skin conduction. A functional element 599 can be configured to record data associated with stimulation delivered by one or more implantable devices 200 (e.g. record data associated with stimulation energy delivered by one or more stimulation elements 260), such as to provide closed loop or semi-closed loop stimulation. A functional element 599 can be configured to record temperature, such as when apparatus 10 is configured to deactivate or otherwise modify the performance of an external device 500 when the recorded temperature (e.g. patient temperature and/or external device 500 temperature) exceeds a threshold.

In some embodiments, an external device 500, programmer 600', and/or programmer 600" comprises a temperature sensor, such as when functional elements 599*a*, 599*b*, and/or 599*c*, respectively, comprise a temperature sensor. The temperature-based functional element 599 can be positioned proximate a portion of programmer 600, housing 510 and/or one or more antennas 540 (e.g. to measure the temperature of one or more portions of a programmer 600 and/or external device 500). In these embodiments, the temperature data recorded by the functional element 599 is used to modify one or more of: matching network; stimulation level (e.g. stimulation energy delivered by one or more implantable devices 200); power transmission level (e.g. level of power transmitted between one or more external devices 500 and one or more implantable devices 200); and combinations of one or more of these. In some embodiments, the temperature sensor-based functional element 599 is a part of a safety mechanism that deactivates programmer 600 and/or an external device 500 if the recorded temperature exceeds a threshold. Alternatively or additionally, a temperature sensor-based functional element 599 can be configured to measure temperature of the patient, such as when placed on housing 510, such as to modify energy and/or agent delivery performed by implantable device 200 based on the recorded patient temperature.

In some embodiments, an external device 500, programmer 600', and/or programmer 600" comprise an accelerometer, vibration sensor, and/or other motion or shock sensor, such when functional elements 599*a*, 599*b*, and/or 599*c* comprise this type of sensor. In these embodiments, the functional elements 599 can comprise a sensor configured to produce a signal used to detect when an external device 500, programmer 600', and/or programmer 600" is dropped, as well as assess the forces generated during the drop. Alternatively or additionally, this sensor can be configured to produce a signal configured to detect a tap (e.g. on a housing) of the device, such that a tap gesture can be used in place of a control (e.g. a discrete switch) on the device.

As described hereabove, implantable system 20 comprises one or more implantable devices 200, such as one or more implantable devices 200 provided sterile or configured to be sterilized for implantation into the patient. A first implantable device 200 can be of similar or dissimilar construction and arrangement to a second implantable device 200'. Each implantable device 200 can be configured to treat a patient (e.g. treat pain of the patient) and/or record patient information, such as by delivering energy and/or an agent to tissue and/or by recording one or more physiologic parameters of the patient (e.g. parameters of tissue of the patient).

One or more portions of an implantable device 200 or other component of implantable system 20 can be configured to be visualized or contain a visualizable portion or other visualizable element, such as visualizable element 222 shown. Visualizable element 222 can comprise a material selected from the group consisting of: radiopaque material; ultrasonically reflective material; magnetic material; and combinations of one or more of these. In these embodiments, each implantable device 200 can be visualized (e.g. during and/or after implantation) via an imaging device such as a CT, X-ray, fluoroscope, ultrasound imager and/or MRI.

In some embodiments, implantable system 20 comprises multiple implantable devices 200 (e.g. implantable device 200 and implantable device 200' shown in FIG. 1) and implantable system 20 comprises a "multi-point ready" system, in which the operation (e.g. energy delivery, agent deliver, data recording and/or other function) of the multiple implantable devices 200 is performed simultaneously, asynchronously, and/or sequentially. The implantable devices 200 can be part of a network including one or more external devices 500 (e.g. external device 500 and external device 500' shown in FIG. 1) in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single external device 500 and/or by multiple external devices 500, which can further be synchronized (e.g. to a single clock). Each implantable device 200 of implantable system 20 can receive a power signal and/or a data signal from one or more external devices 500. In some embodiments of the multipoint ready implantable system 20, each implantable device 200 comprises a unique ID, such that each implantable device 200 is individually addressed (e.g. receive unique signals from external system 50). In some embodiments, external system 50 transmits high-bandwidth signals to implantable system 20, such that time-domain multiple access communication is performed while operating in near real time. In some embodiments, implantable system 20 is configured as a multi-point ready system such that stimulation energy delivered by implantable system 20 is independent of power received by implantable system 20 from external system 50.

Two implantable devices 200, or two discrete components of a single implantable device 200 (e.g. two components comprising or positioned in different housings), can be attached to each other by a connecting filament as defined hereabove. In some embodiments, a connecting filament comprises a user-attachable (e.g. clinician-attachable) connector on at least one end. The filament connector is configured to operably attach to a mating connector on a component (e.g. a housing 210) of an implantable device 200.

Each implantable device 200 is configured to receive power and/or data (e.g. implantable system 20 configuration data) from one or more external devices 500. In some embodiments, one or more implantable devices 200 are configured to receive both power and data (e.g. simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (generally "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

Each implantable device 200 can comprise one or more stimulation elements 260, configured to stimulate, deliver energy to, deliver an agent to, record information from and/or otherwise interface with the patient. Alternatively or additionally, the one or more stimulation elements 260 can be configured as a sensor, such as to record patient information. Each implantable device 200 can comprise housing 210, receiver 230, controller 250, energy storage assembly 270 and/or one or more antennas 240, each described in detail herein. Each stimulation element 260 can comprise a sensor and/or any transducer, as described in detail herein. One or more stimulation elements 260 can be positioned on a lead, lead 265 shown (e.g. a flexible filament including wires or other conductors that connect each stimulation element 260 to electronics within housing 210). Each implantable device 200 can comprise one or more leads 265, such as two leads attached to a single housing 210, or a first lead 265 attached to a first housing 210 and a second lead 265 attached to a second housing 210. Each implantable device 200 can comprise one or more other functional elements, such as functional elements 299a and 299b described herein. Each implantable device 200 can further comprise one or more anchoring or other fixation elements, anchor element 223 shown, as described in detail herebelow.

In some embodiments, one or more implantable devices 200 are further configured to transmit data to one or more external devices 500, such as via one or more antennas 240 transmitting a signal to one or more antennas 540, or otherwise. Data transmitted by an implantable device 200 can comprise patient information (e.g. patient physiologic information recorded by one or more stimulation elements 260 configured as a physiologic sensor), or implantable device 200 information (e.g. data recorded by one or more stimulation elements 260 configured as a sensor and positioned in implantable device 200, or other implantable device 200 configuration and/or performance data).

Housing 210 of each implantable device 200 can comprise one or more rigid and/or flexible materials which surround various components, such as antenna 240, energy storage assembly 270, controller 250 and/or receiver 230 as shown in FIG. 1. In some embodiments, one or more stimulation elements 260 are positioned in, on and/or within housing 210. In some embodiments, housing 210 surrounds a substrate, such as a flexible and/or foldable printed circuit board, such as multiple discrete or continuous printed circuit boards positioned in different planes (e.g. a flexible or foldable printed circuit board). In some embodiments, one or more antennas 240 and/or other components (e.g. a functional element 299) are positioned outside of housing 210, such as when at least one antenna 240 or other component is operably connected to one or more components (e.g.

electrical components) positioned within housing 210 via a tether comprising one or more electrical conduits.

Housing 210 can comprise one or more shapes or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210 can comprise a major axis and a minor axis, defined hereabove. In some embodiments, housing 210 comprises a major axis less than or equal to 20 mm, such as a major axis less than or equal to 15 mm, 12 mm or 10 mm. In some embodiments, housing 210 comprises a minor axis less than or equal to 8 mm, such as a minor axis less than or equal to 6 mm, or less than or equal to 5 mm Housing 210 can comprise a wall thickness between 0.1 mm and 1.0 mm, such as a wall thickness between 0.2 mm and 0.5 mm, such as a wall thickness of approximately 0.3 mm Housing 210 can comprise a displacement volume less than or equal to 2000 $mm^3$, such as less than or equal to 600 $mm^3$.

Housing 210 can comprise one or more portions that are transmissive to radiofrequency (RF) signals. In some embodiments, housing 210 comprises glass. In some embodiments, housing 210 comprises a material selected from the group consisting of: glass; ceramic; stainless steel; titanium; polyurethane; an organic compound; liquid crystal polymer (LCP); gold; platinum; platinum iridium; tungsten; epoxy; a thermoplastic; a thermoset plastic; and combinations of one or more of these. In some embodiments, one or more portions of housing 210 comprises one or more coatings, such as one or more coatings configured to cause or prevent a physiologic reaction and/or a coating configured to block (e.g. shield) an electromagnetic transmission.

Housing 210 can comprise one or more passageways or other feedthroughs, such as for the passage of a lead, wire, optical fiber, fluid delivery tube, mechanical linkage and/or other conduit through a wall of housing 210, such as is described in applicant's co-pending U.S. patent application Ser. No. 17/412,044, titled "Medical Apparatus Including an Implantable System and an External System", filed Aug. 25, 2021.

In some embodiments, one or more inner or outer surfaces (or portions of surfaces) of housing 210 includes an insulating and/or shielding layer (e.g. a conductive electromagnetic shielding layer), such as inner coating 219a and/or outer coating 219b shown (singly or collectively coating 219). Coating 219 can comprise an electrically insulating and/or a thermally insulating layer or other coating. In some embodiments, one or more portions of housing 210 comprise an electrically shielding coating, coating 219, while other portions are transmissive to electromagnetic signals such as radiofrequency signals.

In some embodiments, housing 210 comprises an array of feedthroughs, not shown. In some embodiments, housing 210 is surrounded (e.g. partially or fully surrounded) by a covering, such as a flexible and/or non-conductive covering, such as a covering made of an elastomer.

In some embodiments, implantable device 200 and/or another component of apparatus 10 can include one or more features to prevent or at least reduce migration of implant 200 within the patient's body. In some embodiments, one or more implantable devices 200 comprises one or more anchor elements configured to secure one or more portions of implantable device 200 to tissue (e.g. anchor element 223 described hereabove and/or an anchor element in an overmold positioned about a portion of housing 210). Anchor element 223 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these. While anchor element 223 is shown proximate housing 210 (e.g. to fixedly attach housing 210 to tissue), in some embodiments anchor element 223 surrounds or is otherwise proximate lead 265 (e.g. to fixedly attach lead 265 to tissue). In some embodiments, anchor element 223 comprises a porous mesh that surrounds all or a portion of housing 210. The porous mesh can be configured to promote tissue ingrowth, such as to prevent or at least limit ("prevent" herein) migration of housing 210 when implantable device 200 is implanted in the patient. In some embodiments, anchor element 223 comprises a mesh that is attached to the top side of implantable device 200 (side in closest proximity to the patient's skin), such as to prevent housing 210 from migrating away from the patient's skin (e.g. prevent from migrating deeper into the patient).

One or more antennas 240 (singly or collectively antenna 240) can be configured to receive power and/or data, and receiver 230 can receive the power and/or data from the one or more antennas 240. Each antenna 240 can comprise one or more implantable antennas, such as one or more antennas positioned within housing 210, and/or one or more antennas electrically attached to a connecting filament. In some embodiments, one or more implantable devices 200 comprise at least two antennas 240, or at least three antennas 240. Antenna 240 can be configured to receive power and/or data from one or more external devices 500, such that an attached receiver 230 receives the power and/or data. In some embodiments, implantable system 20 comprises at least two implantable devices 200, each of which comprise one or more (e.g. two or three) antennas 240 which are positioned within a housing 210 and/or electrically tethered to a housing 210. In some embodiments, an implantable device 200 comprises a first antenna 240 positioned in a first plane and a second antenna 240 positioned in a second plane. The first plane and second plane can be relatively orthogonal planes, or planes oriented between 30° and 90° relative to each other, such as between 40° and 90°, approximately 30°, approximately 45° and/or approximately 60° relative to each other. In some embodiments, an implantable device 200 comprises a first antenna 240 positioned in a first plane, a second antenna 240 positioned in a second plane, and a third antenna 240 positioned in a third plane.

In some embodiments, implantable device 200 comprises one or more antennas 240 positioned on a substrate, such as a printed circuit board (PCB), a flexible printed circuit board and/or a foldable substrate (e.g. a substrate comprising rigid portions and hinged portions). In some embodiments, the substrate is folded or otherwise pivoted to position the various antennas 240 on differently oriented planes, such as multiple planes oriented between 5° and 90° relative to each other, such as two antennas 240 positioned on two planes oriented between 30° and 90° or between 40° and 90° relative to each other, or three antennas 240 positioned on three planes oriented between 5° and 60° relative to each other. Two or more antennas 240 can be positioned on two or more different planes that are approximately 45° relative to each other, or approximately 60° or approximately 90° relative to each other.

Implantable device 200 can comprise three antennas 240. In some embodiments, a first antenna 240 comprises an electrical dipole antenna, and the second and third antennas 240 can be positioned in different planes than the first antenna 240. In some embodiments, the three antennas 240 each comprise a loop antenna, such as when each loop antenna is positioned on a different plane. In some embodiments, a first antenna 240 comprises an electrical dipole antenna, and a second antenna 240 and a third antenna 240 each comprise a loop antenna. In these embodiments, the second antenna 240 and the third antenna 240 can be positioned relatively orthogonal to each other (e.g. positioned on two relatively orthogonal planes). In some embodiments, a first antenna (e.g. an electrical dipole antenna) is positioned outside of housing 210, while a second antenna (e.g. a loop antenna) and a third antenna (e.g. a loop antenna) are each positioned on, in and/or within housing 210. In some embodiments, implantable device 200 comprises one or more antennas 240 in which any combination of antenna types (as described herein) are used in combination.

One or more antennas 240 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240 can comprise a loop antenna, such as an elongated loop antenna or a multiple-turn loop antenna.

One or more antennas 240 can comprise a multi-turn spiral loop antenna, such as a multi-turn spiral loop antenna configured to desensitize coupling sensitivity and/or boost input voltage. In some embodiments, one or more antennas 240 comprise multiple concentric loops with varied dimensions, such as concentric loops configured to desensitize coupling sensitivity. In these embodiments, the multiple concentric loops can be arranged as follows: connected in parallel and driven from the same feed point; driven from the same feed point and connected using one or more of a capacitor, inductor, varactor, and combinations of one or more of these; and/or driven from multiple feed points.

One or more antennas 240 can comprise a minor axis and a major axis. In some embodiments, one or more antennas 240 comprise a minor axis between 1 mm and 8 mm, such as between 2 mm and 5 mm. In some embodiments, one or more antennas 240 comprise a major axis between 3 mm and 15 mm, such as between 4 mm and 8 mm. In some embodiments, one or more antennas 240 comprise a major axis above 3 mm, such as between 3 mm and 15 mm, such as when the antenna 240 is positioned outside of housing 210.

One or more antennas 240 can comprise a foldable and/or unfoldable antenna, such as is described in applicant's co-pending U.S. patent application Ser. No. 17/240,629, titled "Method and Apparatus for Minimally Invasive Implantable Modulators", filed Apr. 26, 2021.

One or more antennas 240 can be positioned inside of housing 210. Alternatively or additionally, one or more antennas 240 can be positioned outside of housing 210.

Implantable system 20, one or more implantable devices 200 and/or one or more antennas 240 can be configured to be positioned at a desired depth beneath the patient's skin, such as at a depth between 0.5 cm and 7.0 cm, such as a depth of between 1.0 cm and 3.0 cm.

One or more energy storage assemblies 270 (singly or collectively energy storage assembly 270) can comprise one or more implantable energy storage components, such as one or more batteries (e.g. rechargeable batteries) and/or capacitors (e.g. a supercapacitor). Energy storage assembly 270 can be configured to provide power to one or more of: one or more stimulation elements 260; controller 250; receiver 230; and combinations of one or more of these. In some embodiments, energy storage assembly 270 further provides power to one or more antennas 240 and/or circuitry configured to transmit data via antenna 240. In some embodiments, energy storage assembly 270 includes digital control for charge/discharge rates, voltage outputs, current outputs, and/or system power distribution and/or management.

Energy storage assembly 270 can comprise one or more capacitors with a single or collective capacitance between 0.01 µF and 10F, such as a capacitance between 1 µF and 1.0 mF, or between 1 µF and 10 µF. The energy storage assembly 270 can comprise one or more capacitors with capacitance between 1 mF and 10 F, such as when energy storage assembly 270 comprises a super-capacitor and/or an ultra-capacitor. Such large capacitance can be used to store sufficient charge to maintain operation (e.g. maintain delivery of stimulation energy and/or delivery of an agent) without the use (e.g. sufficient proximity) of an associated external device 500. A capacitor or other energy storage element (e.g. a battery) can be chosen to provide sufficient energy to maintain operation for at least 30 seconds, at least 2 minutes, at least 5 minutes, at least 30 minutes, and up to several hours or more (e.g. during showering, swimming or other physical activity). In some embodiments, energy storage assembly 270 is configured to provide continuous and/or intermittent stimulation energy for at least one charge-balanced pulse (e.g. for the duration of at least one charge-balanced pulse). In some embodiments, a capacitor, battery or other energy storage element is configured to provide stimulation energy without receiving externally supplied power for periods of at least 1 hour, at least 1 day, at least 1 month or at least 1 year. Energy storage assembly 270 can comprise one or more capacitors with a breakdown voltage above 1.0V, such as a breakdown voltage above 1.5V, 4.0V, 10V, or 15V. In some embodiments, energy storage assembly 270 can comprise capacitors distributed outside of housing 210, such as when one or more capacitors are distributed along lead 265. Energy storage assembly 270 can comprise one or more capacitors with low self-leakage, such as to maintain stored energy for longer periods of time.

In some embodiments, energy storage assembly 270 comprises a temporary energy storage component, such as a super-capacitor, configured to store a sufficient quantity of energy to provide uninterrupted stimulation, such as during time periods in which the link gain may be of poor quality or it may be temporarily unavailable (e.g. an external device 500 not being in place such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more stimulation elements 260 to deliver stimulation energy during subsequent (intended or unintended) unavailability of one or more external devices 500 (e.g. an external device 500 is intentionally removed or unintentionally falls off or otherwise loses its position sufficiently proximate one or more implantable devices 200). An energy storage assembly 270 comprising one or more high capacity energy storage components can be beneficial in applications where therapy interruption provides a significant risk or is otherwise relatively unacceptable, such as for life support therapies, cardiac resynchronization therapies, and the like. The high capacity energy storage components of energy storage assembly 270 can be positioned in an assembly positioned within housing 210, on an inner or outer surface of housing 210, within a separate housing, and/or within lead 265.

In some embodiments, during use (e.g. during period of providing stimulation or other function) implantable device 200 receives power regularly from external system 50 (e.g. relatively continuously while implantable device 200 delivers stimulation energy), and energy storage assembly 270 comprises a relatively small battery or capacitor, such as a battery or capacitor that has an energy storage capacity of less than or equal to 0.6 Joules, 7 Joules or 40 Joules.

One or more controllers 250 (singly or collectively controller 250) can be configured to control one or more stimulation elements 260, such as a stimulation element 260 comprising a stimulation-based transducer (e.g. an electrode or other energy delivery element) and/or a sensor (e.g. a physiologic sensor and/or a sensor configured to monitor an implantable device 200 parameter). In some embodiments, controller 250 is configured to transmit a stimulation signal (e.g. transmit stimulation energy configured in one or more stimulation waveforms) to one or more stimulation elements 260 (e.g. one or more stimulation elements 260 comprising an electrode and/or other energy delivery element), independent of the power signal received by one or more antennas 240 (e.g. independent of power transmitted by external system 50), such as by using energy stored in energy storage assembly 270. In these embodiments, the power signal and/or the RF path for the power signal can be modified to optimize power efficiency (e.g. by tuning matching network on transmitter 530 and/or receiver 230; configuring antennas 540 and/or 240 in an array; tuning operating frequency; duty cycling the power signal; adjusting antenna 540 and/or 240 position; and the like), and a stimulation signal can be precisely delivered (e.g. by using energy stored on energy storage assembly 270 and generating stimulation signal locally on the implantable device 200) to ensure clinical efficacy. Also, if the power signal transmission (also referred to as "power link") is perturbed unexpectedly, the stimulation signal can be configured so that it is not significantly affected (e.g. unaffected). In some configurations, the stimulation signal being delivered by one or more implantable devices 200 is insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250 can receive commands from receiver 230, such as one or more commands related to one or more implantable device 200 configuration parameters selected from the group consisting of: stimulation parameter; data rate of receiver; data rate of data transmitted by the first implantable device 200 at least one implantable antenna 240; stimulation element 260 configuration; state of controller 250; antenna 240 impedance; clock frequency; sensor configuration; electrode configuration; power management parameter; energy storage assembly parameter; agent delivery parameter; sensor configuration parameter; and combinations of one or more of these. Controller 250 can comprise one or more electronic elements, electronic assemblies, and/or other electronic components, such as components selected from the group consisting of: memory storage components; analog-to-digital converters; rectification circuitry; state machines; microprocessors; microcontrollers; filters and other signal conditioners; sensor interface circuitry; transducer interface circuitry; and combinations thereof. In some embodiments, controller 250 comprises a memory storage component that includes instructions, such as instructions used by controller 250 to produce a stimulation waveform and/or perform an algorithm, each as described herein.

In some embodiments, one or more stimulation elements 260 comprise a stimulation element configured to deliver energy (e.g. one or more electrodes configured to deliver monopolar or bipolar electrical energy) to tissue, and controller 250 is configured to control the energy delivery, such as to control (e.g. provide, determine, and/or adjust) one or more stimulation parameters. Each of these stimulation parameters can be held relatively constant, and/or varied, such as a variation performed in a continuous or intermittent manner. In some embodiments, one or more stimulation parameters are varied in a random or pseudo-random (hereinafter "random") manner, such as a variation performed by apparatus 10 using a probability distribution as described in applicant's co-pending U.S. patent application Ser. No. 17/372,095, titled "Apparatus with Enhanced Stimulation Waveforms", filed Jul. 9, 2021. In some embodiments, stimulation (e.g. stimulation comprising high frequency and/or low frequency signal components) is varied randomly to eliminate or at least reduce synchrony of neuronal firing with the stimulation signal (e.g. to reduce paresthesia or other patient discomfort). In some embodiments, one or more stimulation elements 260 comprise a stimulation element configured to stimulate a target (e.g. nerve tissue such as spinal nerve tissue and/or peripheral nerve tissue). The amount of stimulation delivered to the target can be controlled by varying a parameter selected from the group consisting of: stimulation element 260 size and/or configuration (e.g. electrode size and/or configuration); stimulation element 260 shape (e.g. electrode shape, magnetic field generating transducer shape or agent delivering element shape); shape of a generated electric field; shape of a generated magnetic field; stimulation signal parameters; and combinations of one or more of these.

In some embodiments, one or more stimulation elements 260 comprise an element configured to deliver electrical energy to tissue (e.g. one or more electrodes configured to deliver monopolar or bipolar electrical energy), and controller 250 is configured to control charge balance, such as to actively and/or passively control charge balance, as described herebelow. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.01 mA to 15 mA (such as between 0.1 mA and 15 ma, between 0.1 mA and 12 mA, or between 0.1 mA and 10 mA), depending on the treatment, the error in charge balance can be on the order of 0.001% to 0.01%. Alternatively or additionally, controller 250 can comprise AC coupling capacitors that are configured to balance stimulation waveforms passively. The AC coupling capacitance can be fairly large (e.g. greater than 10 μF), in order to pass the stimulation waveform with minimal filtering. In some embodiments, apparatus 10 is configured to perform active charge balancing. In some embodiments, an implantable device 200 comprises a precise resistor in series with a stimulation electrode-based stimulation element 260. The precise resistor can be used to measure outflow and inflow currents, such as when controller 250 comprises an analog to digital converter (ADC). Controller 250 can integrate current over time during a first phase in which stimulation energy is delivered, and during a second phase in which a reverse current is applied (e.g. a reverse current used to balance charge). Controller 250 can be configured to balance the total charge in the two phases, to ensure that the net DC current is approximately zero. The integration can be achieved using an analog integrator and/or a digital summer of controller 250, with controller 250 keeping track of one or more parameters of the pulses delivered (e.g. pulses delivered within a train or a burst). Implantable device 200 can comprise a precise series resistance comprising an "on-chip" trimmed resistor or an "off-chip" resistor. In some embodiments, implantable device 200 comprises a bank of trimmed resistors that are used to control the net series resistance, such as to adjust resistance based on stimulation amplitude requirements (e.g. to take advantage of the full dynamic range of an ADC of controller 250). In some embodiments, controller 250 comprises a shunt path with an RC-based low pass filter used for both outflow and inflow of current. RC elements of controller 250 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse. The ADC resolution can be high enough to ensure the residual error is less than what would cause an undesired charge accumulation. ADC resolution requirements can be further reduced by reducing the net capacitance in a shunt RC circuit, to cause accelerated charging of the capacitor. The capacitor can be discharged every time the voltage exceeds a certain predefined threshold, while controller 250 keeps track of the number of times the capacitor has been charged and reset. By resetting the capacitor through a low resistance path, the discharge time can be insignificant compared to the charge time, reducing the error due to the discharge period. Since the net charge equivalent to full scale voltage on the ADC can be divided into multiple cycles, the required resolution of the ADC to achieve the same residual error can be divided by the number of cycles.

In some embodiments, controller 250 is configured to produce a stimulation signal comprising a waveform or a waveform pattern (hereinafter stimulation waveform), for one or more stimulation elements 260 configured as a stimulation element (e.g. such that one or more stimulation elements 260 deliver stimulation energy comprising or at least resembling that stimulation waveform). Controller 250 can produce a stimulation signal comprising a waveform selected from the group consisting of: square wave; rectangle wave; sine wave; sawtooth; triangle wave (e.g. symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to produce a stimulation signal comprising a waveform including a combination of two or more waveforms selected from the group consisting of: square wave; rectangle wave; sine wave; triangle wave (symmetric or asymmetric); ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to construct a custom waveform (e.g. an operator customized waveform), such as by adjusting amplitude at specified time steps (e.g. for one or more pulses). In some embodiments, controller 250 is configured to generate a waveform including one or more random parameters (e.g. random timing of pulses or random changes in frequency, rate of change or amplitude).

In some embodiments, controller 250 is configured to provide a stimulation signal comprising waveforms and/or pulses repeated at a frequency (e.g. includes a frequency component) between 1.0 Hz and 50 KHz, such as between 10 Hz and 500 Hz, between 40 Hz and 160 Hz and/or between 5 KHz and 15 KHz. In some embodiments, controller 250 is configured to produce a stimulation signal comprising a frequency between 1 Hz and 1000 Hz, such as a stimulation signal with a frequency between 10 Hz and 500 Hz. In some embodiments, controller 250 is configured to produce a stimulation signal comprising a duty cycle between 0.1% and 99%, such as a duty cycle between 1% and 10% or between 1% and 25%. In some embodiments, controller 250 is configured to produce a stimulation signal comprising a frequency modulated stimulation waveform, such as a stimulation waveform comprising a frequency component (e.g. signal) between 1 kHz and 20 kHz. In some embodiments, controller 250 is configured to produce a stimulation signal comprising a mix and/or modulation of low frequency and high frequency signals, which comprise any of the waveform types, shapes and other configurations. In these embodiments, the stimulation signal can comprise low frequency signals between 1 Hz and 1000 Hz, and high frequency signals between 600 Hz and 50 kHz, or between 1 kHz and 20 kHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse width and/or frequency of the pulses.

Controller 250 can comprise a clamping circuit configured to allow fast charging and/or discharging of the energy storage assembly 270, stimulation element 260 drivers (e.g. electrode drivers) of controller 250, and/or other components of implantable device 200. The clamping circuit can improve pulse shape by offering additional control and/or configuration of rise and fall times in the shape of the waveform (e.g. to create rapid rise or fall times). In some embodiments, the clamping circuit can be configured to limit the rise and/or fall time to be less than or equal to one-tenth (10%) of the pulse width of an applied stimulation pulse (e.g. less than or equal to 1 μsec rise and/or fall time for a 10 μsec stimulation pulse).

In some embodiments, controller 250 comprises a matching network configured to match the impedance of a first antenna 240 with the impedance of the receiver 230. In these embodiments, controller 250's matching network can be adjustable. Alternatively or additionally, controller 250 can comprise an adjustable loading impedance to stabilize the load seen at an antenna 240 under different operating conditions. In some embodiments, the adjustable loading impedance is controlled according to the charge rate of the energy storage assembly 270.

Controller 250 and/or any other component of each implantable device 200 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230 (singly or collectively receiver 230) can comprise one or more components, such as demodulator 231, rectifier 232, and/or power converter 233 shown in FIG. 1. In some embodiments, receiver 230 can comprise a DC-DC converter such as a boost converter. Receiver 230 can comprise a data receiver, such as a data receiver including an envelope detector and demodulator and/or an envelope averaging circuit. In some embodiments, one more antennas 240 separately connect to one or more receivers 230. In some embodiments, one or more antennas 240 connect to a single receiver 230, such as via a series connection or a parallel connection.

One or more implantable devices 200 can be configured to transmit a data signal to external system 50. In some embodiments, receiver 230 is configured to drive one or more antennas 240 to transmit data to external system 50 (e.g. to an antenna 540 of an external device 500). Alternatively or additionally, implantable device 200 can be configured to transmit a data signal by having receiver 230 adjust a load impedance to backscatter energy, such as a backscattering of energy which can be detected by external system 50. In some embodiments, data transmission is accomplished by receiver 230 manipulating a signal at a tissue interface, such as to transmit a data signal using body conduction.

In some embodiments, receiver 230 comprises a matching network, such as a matching network configured to detune to prevent oversaturation. For example, implantable system 20 can comprise two or more implantable devices 200 each of which includes a receiver 230 comprising a matching network. A first implantable device 200's receiver 230's matching network can be configured to detune based on power received by the second implantable device 200's receiver 230.

Demodulator 231 can comprise circuitry that asynchronously recovers signals modulated on the power signal provided by external system 50, and that converts the modulated signals into digital signals. In some embodiments, demodulator 231 asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, demodulator 231 recovers a digital signal that is used as timing information for an implantable device 200, similar to an on-chip clock. The recovered clock signal can also be used to synchronize an on-chip clock generator of controller 250, such as through the use of a frequency and/or phase locked loop (FLL or PLL).

Rectifier 232 can comprise a power signal rectifier, such as to provide power to the energy storage assembly 270 and/or controller 250. In some embodiments, rectifier 232 comprises one or more self-driven synchronous rectifier (SDSR) stages connected in charge-pump configuration, to boost the voltage from input RF amplitude to the rectifier to a higher voltage. The boosted voltage can directly charge energy storage assembly 270, or it can be further boosted by a DC-DC converter or boost converter. In some embodiments, rectifier 232 comprises diode-capacitor ladder stages instead of, or in addition to, SDSR stages. On-chip diodes, such as Schottky diodes, or off-chip diodes can be used in one or more rectifier 232 stages. For maximum efficiency, the rectification elements, such as diodes, can be optimized to minimize forward conduction and/or reverse conduction losses by properly sizing the components and selecting appropriate number of stages based on the input RF voltage and load current.

Power converter 233 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters 233 can interface with energy storage assembly 270 and charge up associated energy storage components to desired voltages. In some embodiments, power converter 233 receives control signals from controller 250, such as to configure voltages, currents, charge/discharge rates, switching frequencies, and/or other operating parameters of power converter 233.

One or more implantable leads 265 (singly or collectively lead 265) can be attached to one or more housings 210, such as a lead 265 comprising one or more stimulation elements 260. Lead 265 can comprise one or more stimulation elements 260 configured as a stimulation element (e.g. an electrode configured to deliver electrical energy in monopolar or bipolar mode or an agent delivery element such as an output port fluidly connected to a reservoir within housing 210). Alternatively or additionally, lead 265 can comprise one or more stimulation elements 260 and/or functional elements 299b that is configured as a physiologic sensor (e.g. an electrode configured to record electrical activity of tissue or another physiologic sensor as described herein). Alternatively or additionally, lead 265 can comprise one or more stimulation elements 260 and/or functional elements 299b that is configured to transmit signals through tissue to external system 50, such as through body conduction.

In some embodiments, implantable device 200 comprises a connector, connector 215, that operably attaches (e.g. electrically attaches) one or more stimulation elements 260 to one or more components (e.g. electronic components) internal to housing 210 (e.g. to transfer power and/or data therebetween). In some embodiments, connector 215 is operably attached (e.g. in a manufacturing process) or attachable (e.g. in a clinical procedure) to lead 265 as shown in FIG. 1. Alternatively, connector 215 can be operably attached and/or attachable to a lead connection assembly, assembly 280, which in turn can be attached to a lead 265. In some embodiments, connector 215 passes through an opening in housing 210, in a feed-through arrangement. In some embodiments, an overmold or other sealing element, sealing element 205 shown, provides a seal about connector

215, the opening in housing 210 and/or the interface between connector 215 and housing 210.

In some embodiments, lead 265 comprises a removable stylet configured to aid in the implantation of lead 265, such as is described in applicant's co-pending U.S. patent application Ser. No. 17/412,044, titled "Medical Apparatus Including an Implantable System and an External System", filed Aug. 25, 2021. In some embodiments, implantable system 20 comprises more than one lead 265, comprising one or more stimulation elements 260 and attached to one or more housings 210 of one or more implantable devices 200. In some embodiments, one or more leads 265 can be attached to a single housing 210.

In some embodiments, lead 265 comprises a diameter between 1 mm and 4 mm, such as a diameter between 1 mm and 2 mm, such as a lead with a diameter of approximately 1.35 mm. In some embodiments, lead 265 comprises a length between 3 cm and 60 cm, such as a length between 6 cm and 30 cm. One or more leads 265 can include between 2-64 stimulation elements 260, such as when a lead 265 comprises between 2 and 64 electrodes, such as between 4 and 32 electrodes. In some embodiments, lead 265 comprises a paddle lead. In some embodiments, lead 265 comprises a single or multi-lumen catheter, such as when an attached implantable device 200 is configured as an agent delivery apparatus as described herein (e.g. a stimulation element 260 configured as a catheter comprises at least a portion of lead 265).

In some embodiments, lead 265 comprises one or more tines, such as tines 266 shown. Tines 266 can be configured to anchor or otherwise stabilize ("anchor" or "stabilize" herein) lead 265 relative to patient tissue, such as to prevent undesired movement during and/or after an implantation procedure for lead 265. One or more tines 266 can be configured to biodegrade after implantation in the patient, such that the stabilization provided is temporary. Tines 266 can be configured to biodegrade over a time period of approximately 4 to 12 weeks. In some embodiments, biodegradable tines 266 are configured to be incorporated when lead stimulation elements 260 are positioned to stimulate a peripheral nerve (e.g. lead 265 is implanted such that one or more stimulation elements 260 are positioned proximate one or more peripheral nerves).

In some embodiments, one or more tines 266 are configured to be deployed, such as via an operator-accessible control.

One or more stimulation elements 260 (singly or collectively stimulation element 260) and/or functional element 299 (e.g. functional element 299a and/or 299b) can comprise one or more sensors, transducers and/or other functional elements. In some embodiments, one or more stimulation elements 260 and/or functional elements 299 comprise at least one sensor and/or at least one transducer (e.g. a single stimulation element 260 or multiple stimulation elements 260). In some embodiments, stimulation element 260 and/or functional element 299 comprises a functional element configured to provide a therapy, such as one or more stimulation elements 260 configured to deliver an agent to tissue (e.g. a needle or catheter), to deliver energy to tissue and/or to otherwise therapeutically affect tissue. In some embodiments, stimulation element 260 and/or functional element 299 comprises one or more functional elements configured to record patient information, such as when stimulation element 260 and/or functional element 299 comprises one or more sensors configured to measure a patient physiologic parameter, as described herein. In some embodiments, stimulation element 260 and/or functional element 299 comprises one or more sensors configured to record an implantable device 200 parameter, also as described herein.

One or more stimulation elements 260 can be positioned on lead 265 as shown in FIG. 1. Alternatively or additionally, one or more stimulation elements 260 can be positioned on housing 210. One or more functional elements 299 can be positioned on lead 265 (e.g. functional element 299b shown) and/or positioned on and/or within housing 210 (e.g. functional element 299a shown).

Stimulation element 260 can comprise one or more stimulation elements positioned at one or more internal body locations. Stimulation element 260 can comprise one or more stimulation elements positioned to interface with (e.g. deliver energy to and/or record a physiologic parameter from) spinal cord tissue, spinal canal tissue, epidural space tissue, spinal root tissue (dorsal or ventral), dorsal root ganglion, nerve tissue (e.g. peripheral nerve tissue, spinal nerve tissue or cranial nerve tissue), brain tissue, ganglia (e.g. sympathetic or parasympathetic) and/or a plexus. In some embodiments, stimulation element 260 comprises one or more elements positioned proximate and/or within one or more tissue types and/or locations selected from the group consisting of: one or more nerves; one or more locations along, in and/or proximate to the spinal cord; peripheral nerves of the spinal cord including locations around the back; the knee; the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; the spine; the vagus nerve; the renal nerve; an organ; the heart; the liver; the kidney; an artery; a vein; bone; and combinations of one or more of these, such as to stimulate and/or record data from the tissue and/or location in which the stimulation element 260 is positioned proximate to and/or within. In some embodiments, apparatus 10, implantable device 200 and/or stimulation element 260 are configured to stimulate spinal nerves, peripheral nerves and/or other tissue as described in applicant's co-pending U.S. patent application Ser. No. 16/993,999, titled "Apparatus for Peripheral or Spinal Stimulation", filed Aug. 14, 2020.

In some embodiments, stimulation element 260 and/or functional element 299 comprises one or more sensors configured to record data representing a physiologic parameter of the patient. Stimulation element 260 and/or functional element 299 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 (e.g. via stimulation element 260, functional element 299, and/or functional element 599) can be configured to record a patient parameter (e.g. patient physiologic and/or patient environment parameter) selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity (e.g. as measured using EMG); skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, stimulation element 260 and/or functional element 299 comprises one or more sensors configured to record data representing a parameter of implantable device 200. In these embodiments, stimulation element 260 and/or functional element 299 can comprise one or more sensors selected from the group consisting of: an energy sensor; a voltage sensor; a current sensor; a temperature sensor (e.g. a temperature of one or more components of implantable device 200); a contamination detector (e.g. to detect undesired material that has passed through housing 210); an antenna matching and/or mismatching assessment sensor; power transfer sensor; link gain sensor; power use sensor; energy level sensor; energy charge rate sensor; energy discharge rate sensor; impedance sensor; load impedance sensor;

instantaneous power usage sensor; average power usage sensor; bit error rate sensor; signal integrity sensor; and combinations of one or more of these. Apparatus 10 can be configured to analyze (e.g. via implantable controller 250, programmer 600 and/or diagnostic assembly 62 described herebelow) the data recorded by stimulation element 260 and/or functional element 299 to assess one or more of: power transfer; link gain; power use; energy within energy storage assembly 270; performance of energy storage assembly 270; expected life of energy storage assembly 270; discharge rate of energy storage assembly 270; ripple or other variations of energy storage assembly 270; matching of antenna 240 and 540; communication error rate between implantable device 200 and external device 500; integrity of transmission between implantable device 200 and external device 500; and combinations of one or more of these. A stimulation element 260 can be configured to record temperature, such as when apparatus 10 is configured to deactivate or otherwise modify the performance of an implantable device 200 when the recorded temperature exceeds a threshold.

In some embodiments, one or more stimulation elements 260 comprise a transducer configured to deliver energy to tissue, such as to treat pain and/or to otherwise stimulate or affect tissue. In some embodiments, stimulation element 260 comprises a stimulation element, such as one or more transducers selected from the group consisting of: an electrode; an energy delivery element such as an electrical energy delivery element, a light energy delivery element, a laser light energy delivery element, a sound energy delivery element, a subsonic sound energy delivery element and/or an ultrasonic sound delivery element; an electromagnetic field generating element; a magnetic field generating element; a mechanical transducer (e.g. delivering mechanical energy to tissue); a tissue manipulating element; a heat generating element; a cooling (e.g. cryogenic or otherwise heat extracting energy) element; an agent delivery element such as a pharmaceutical drug delivery element; and combinations of one or more of these.

In some embodiments, one or more stimulation elements 260 comprises a drug or other agent delivery element, such as a needle, port, iontophoretic element, catheter, or other agent delivering element that is connected to a reservoir of agent positioned within housing 210 (e.g. reservoir 225 described herebelow). In some embodiments, one or more stimulation elements 260 comprise a drug eluting element configured to improve biocompatibility of implantable system 20.

In some embodiments, one or more stimulation elements 260 comprise one or more electrodes configured to deliver energy to tissue and/or to sense a patient parameter (e.g. electrical activity of tissue or other patient physiologic parameter). In these embodiments, one or more stimulation elements 260 can comprise one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, apparatus 10 (e.g. via stimulation element 260, functional element 299, and/or functional element 599) is configured to both record one or more patient parameters, and also to perform a medical therapy (e.g. stimulation of tissue with energy and/or an agent). In these embodiments, the medical therapy can be performed in a closed-loop fashion, such as when energy and/or agent delivery is modified based on the measured one or more patient physiologic parameters.

In some embodiments, one or more stimulation elements 260 comprise an agent delivery element, such as a fluid delivery element (e.g. a catheter, a porous membrane, an iontophoretic element or a needle) in fluid communication with a reservoir of the agent positioned within housing 210, such as reservoir 225 described herebelow.

In some embodiments, apparatus 10 comprises one or more tools, tool 60 shown. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g. patient physiologic information) recorded by implantable system 20; patient environment information recorded by implantable system 20; and combinations of one or more of these. Tool 60 can be configured to receive data from wired or wireless (e.g. Bluetooth) means. Tool 60 can comprise a tool selected from the group consisting of: a data logging and/or storage tool; a data analysis tool; a network such as a LAN or the Internet; a cell phone; and combinations of one or more of these.

In some embodiments, tool 60 comprises a battery charging assembly, such as an assembly configured to recharge one or more power supplies 570 comprising a rechargeable battery or capacitor.

In some embodiments, tool 60 comprises a user interface of apparatus 10, such as a user interface configured to allow the patient, clinician, or other user to create a set of stimulation parameter settings based on various user input.

Apparatus 10 can include one or more placement tools, positioning tool 67 shown, which can be configured to aid in the positioning and/or maintenance of one or more external devices 500 on the patient's skin (e.g. at a location proximate an implanted implantable device 200).

Apparatus 10 can include one or more implantation tools, tool 65 shown. Implantation tool 65 can comprise an introducer, tunneller, and/or other implantation tool constructed and arranged to aid in the implantation of housing 210, implantable antenna 240, lead 265 and/or one or more stimulation elements 260. In some embodiments, tool 65 comprises a component configured to anchor implantable device 200 to tissue, such as a mesh or wrap that slides around at least a portion of implantable device 200 and is configured to engage tissue (e.g. via tissue ingrowth) or be engaged with tissue (e.g. via suture or clips).

In some embodiments, one or more components (and/or portions of components) of tool 65 comprises a lubricious coating and/or a lubricous material ("lubricious coating" herein), such as to reduce tissue trauma and/or reduce pain to the patient. For example, tool 65 can comprise an introducer, tunneller, pocket formation tool, needle, and/or other insertion tool with at least a portion comprising a lubricious coating configured to ease insertion of the tool. Typical coatings and materials include but are not limited to: a polytetrafluoroethylene coating or material; a hydrophilic coating or material; and combinations of these.

In some embodiments, one or more components (and/or portions of components) of tool 65 comprises one or more "visualizable portions", such as a radiopaque portion that is visible in X-ray imaging (e.g. fluoroscopy) and/or ultrasonically visible portion that is visible in ultrasound imaging. For example, tool 65 can comprise an introducer including an ultrasonically visible or otherwise visible portion that is used to position the introducer, such as during the implantation of lead 265 or another portion of implantable device 200.

In some embodiments, lead 265 comprises a paddle lead or other stimulating lead and tool 65 comprises an introducer (e.g. a needle or an extended-width introducer) configured to deliver at least a distal portion of lead 265 into an epidural space of a patient. Tool 65 can comprise an introducer comprising a Tuohy needle, such as a Tuohy needle of 12 gauge or smaller Tool 65 can comprise a handle for manipulating lead 265. Tool 65 can be configured to place lead 265 at an entry point above the lumbar spinal column (e.g. between L1 and L2 vertebrae). Tool 65 can include extension tubing used to insert lead 265. Tool 65 can further comprise a tool configured to anchor lead 265, such as when tool 65 comprises sutures, clips, other anchoring elements and/or an anchor securing tool (e.g. a needle or a stapling device), such as to secure lead 265 in subcutaneous tissue. Lead 265 and/or tool 65 can comprise extension tubing used to place lead 265, such as extension tubing that remains in place after removal of an introducer of tool 65. Tool 65 can be configured to place lead 265 against the dura of the spinal cord of the patient.

In some embodiments, tool 65 and/or lead 265 are constructed and arranged to implant lead 265 to stimulate one or more multifidus (MF) muscle fascicles, such as at least three sets of multifidus muscle fascicles. Lead 265 can be secured to a vertebra (e.g. on the transverse process, lamina or vertebral body). Lead 265 can be placed via tool 65 such that one or more stimulation elements 260 (e.g. electrodes) are positioned within the multifidus muscle structures. One or more stimulation elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Stimulation elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, stimulation elements 260 are positioned to cause transvascular stimulation (e.g. transvascular stimulation from arteries and/or veins in a leg or arm). In some embodiments, stimulation elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, stimulation elements 260 are configured to deliver stimulation energy to contract the multifidus muscle. In some embodiments, stimulation elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool 60 comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described herein. Alternatively or additionally, two more external system 50 components and/or two or more implantable system 20 components transmit information and/or power via a wireless transmitter (e.g. an RF transmitter), magnetic coupling, inductive coupling; capacitive coupling and/or other wireless transmission means.

Apparatus 10 can include one or more positioning devices, such as patient attachment device 70 shown in FIG. 1, that is used to attach one or more components of external system 50 to a location on or at least proximate the patient. In some embodiments, patient attachment device 70 is constructed and arranged as described in applicant's co-pending U.S. patent application Ser. No. 17/187,654, titled "Method and Apparatus for Neuromodulation Treatments of Pain and Other Conditions", filed Feb. 26, 2021.

Patient attachment device 70 can comprise one or more elements configured to attach one or more external devices 500 and/or programmer 600 at one or more locations on or proximate the patient's skin, that are relatively close to one or more implantable devices 200 that have been implanted in the patient. Patient attachment device 70 can comprise a component selected from the group consisting of: belt; belt with pockets; belt with adhesive; adhesive; strap; strap with pockets; strap with adhesive shoulder strap; shoulder band; shirt; shirt with pockets; clothing; clothing with pockets; epidural electronics packaging; clip; bracelet; wrist band;

wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g. at least one antenna 540 mounted to or otherwise positioned on a printed circuit board such as a flexible printed circuit board). Patient attachment device 70 can include one or more pockets, such as one or more pockets configured to collectively surround one or more of: external device 500; one or more antennas 540; power supply 570; programmer 600; and combinations of one or more of these. In some embodiments, patient attachment device 70 comprises multiple pockets, such as to allow repositioning of an external antenna 540, programmer 600, external transmitter 530 and/or external power supply 570 to various different locations, such as to improve transmission of power and/or data to one or more implantable devices 200 and/or improve patient comfort. In some embodiments, one or more antennas 540, power supplies 570, and/or transmitters 530 are connected through flexible cables positioned in patient attachment device 70. In some embodiments, the flexible cables are small coax cables that accommodate the power levels and frequencies of the carried signals. In some embodiments, the one or more antennas 540 are connected to one or more additional components of external device 500 through a single cable with a local power splitting component and/or active matching element that adjusts signal power to each of the one or more antennas 540.

In some embodiments, patient attachment device 70 and/or external device 500 can be configured to prevent adversely affecting portions of the skin contacted by either device. Alternatively or additionally, patient attachment device 70 and/or external device 500 can be configured to clean and/or to promote healing of one or more skin-contacting portions. For example, patient attachment device 70 can include an agent (e.g. a coating or other included agent) selected from the group consisting of: a bactericidal agent; an anti-fungal agent; and combinations thereof.

In some embodiments, an anchoring-based tool, patient attachment device 70, is used on a patient-by-patient basis, such as when used on overweight patients and/or to otherwise avoid migration of implantable device 200 sideways and/or downward (e.g. into fat tissue).

Apparatus 10 can comprise a device configured to operate (e.g. temporarily operate) one or more implantable devices 200, such as trialing interface 80 shown in FIG. 1. Trialing interface 80 can be configured to wirelessly deliver power to an implantable device 200, wirelessly deliver data to an implantable device 200, and/or wirelessly receive data from an implantable device 200. Trialing interface 80 can be configured to interface with one or more implantable devices 200 during an implantation procedure in which one or more implantable devices 200 are implanted in a patient (e.g. a sterile clinical procedure in which an implantable device 200 comprising a pre-attached lead 265 is implanted in a patient). Trialing interface 80 can be configured to be sterilized one or more times. Trialing interface 80 can comprise one or more antennas, such as an antenna similar to antenna 540 of an external device 500. Trialing interface 80 can comprise a transmitter, such as a transmitter similar to transmitter 530 of external device 500, and a power supply, such as a power supply similar to power supply 570 of external device 500. In some embodiments, trialing interface 80 is of similar construction and arrangement to the trialing interface described in applicant's co-pending U.S.

patent application Ser. No. 17/187,654, titled "Method and Apparatus for Neuromodulation Treatments of Pain and Other Conditions", filed Feb. 26, 2021. In some embodiments, trialing interface 80 includes a housing to be positioned proximate at least a portion of implantable device 200, such as a housing 210 that surrounds an antenna and a transmitter that is configured to operatively couple to (e.g. transmit power and/or data to) one or more antennas 240 of one or more implantable devices 200.

In some embodiments, trialing interface 80 is constructed and arranged as described an applicant's co-pending U.S. patent application Ser. No. 17/379,928, titled "Stimulation Apparatus", filed Jul. 19, 2021.

As described hereabove, trialing interface 80 can be used in clinical procedures (e.g. used in a trialing session portion of a clinical procedure) in which an implantable device 200 including a pre-attached lead 265 is implanted. In some embodiments, implantable device 200 includes an attachable lead 265, and apparatus 10 includes trialing interface 90. Trialing interface 90 can be configured to operably (e.g. electrically) attach to lead 265, such as to deliver stimulation energy via a wired connection during a trialing procedure, as described herein. For example, trialing interface 90 can deliver stimulation energy to one or more stimulation elements 260 of lead 265 during a trialing procedure in which proper position of stimulation element 260 is confirmed and/or modified, and/or one or more stimulation waveforms are tested. Trialing interface 90 can include an interface connector 95 configured to operably attach (e.g. electrically attach) trialing interface 90 to lead 265 (e.g. after lead 265 has been implanted in tissue of the patient). Connector 95 can be configured to be used in a single trialing procedure (e.g. on a single patient), while the remainder of trialing interface 90 can be reused (e.g. in multiple trialing procedures for multiple patients). Trialing interface 90 can comprise a device that is sterilized, and it can be a device that can be re-sterilized (e.g. to be used in multiple sterile clinical procedures). In some embodiments, trialing interface 80 and trialing interface 90 include similar components, (e.g. similar components used to create similar stimulation waveforms to be used in a trialing procedure).

In some embodiments, one or more implantable devices 200 of implantable system 20 comprises an implantable transmitter configured to transmit data, such as to transmit data (e.g. stimulation information, patient physiologic information, patient environment information, implantable device 200 performance and/or configuration information, and the like) to one or more external devices 500. In these embodiments, receiver 230 can be configured as both a receiver and a transmitter. One or more implantable devices 200 can be configured to transmit data by sending a signal to (i.e. "driving") one or more antennas 240 or another antenna of implantable device 200. An implantable device 200 can be configured to transmit data using one or more of: load modulation; a signal carrier; and/or body conduction. An implantable device 200 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 62 shown in FIG. 1. In some embodiments, programmer 600 and/or implantable controller 250 comprise all or a portion of diagnostic assembly 62. Diagnostic assembly 62 can be configured to assess, monitor, determine and/or otherwise analyze patient information and/or implantable device 200 information, such as when one or more stimulation elements 260, functional elements 299, and/or functional elements 599 are configured as a sensor configured to record patient information (e.g. patient physiologic information and/or patient environment information) and/or apparatus 10 information (e.g. implantable device 200 information) as described herein. Diagnostic assembly 62 can be configured to analyze communication and/or the power link between an implantable device 200 and an external device 500. In some embodiments, such a communication link analysis can be performed by measuring bit error rate (BER) of a known data stream during communication signal transmission (also referred to as "communication link") measurement phase (e.g. such as during a calibration procedure). The BER can be tracked by the implant controller 250 or programmer 600, such as to monitor and keep track of any trends in the link. This trend can be used to adjust the link and/or provide feedback to an operator of apparatus 10 (e.g. the patient), in case the link cannot be automatically adjusted to compensate for a negative trend (e.g. such that the operator can perform physical re-adjustment of the external system 50). Alternatively or additionally, a power link analysis can be performed by monitoring charge/discharge rate of the implanted energy storage assembly 270. Similar to the communication link, the power link status and/or trending can be monitored and recorded for link adjustment and/or feedback purposes. Diagnostic assembly 62 can be configured to analyze a result of stimulation energy delivered by implantable device 200, such as when a stimulation element 260 comprises an electrode to record electrical activity of tissue (e.g. in addition to delivering electrical energy to stimulate tissue). A stimulation element 260, a functional element 299, and/or a functional element 599 can comprise a sensor configured to record neural activity and/or muscular activity, and the diagnostic assembly configured to analyze the recorded sensor data. In some embodiments, diagnostic assembly 62 is configured to analyze impedance, such as when a stimulation element 260, a functional element 299, and/or functional element 599 comprises a sensor configured to record data related to impedance, such as when implantable device 200 performs a frequency sweep, performs an impulse response and/or compares voltage and current of a stimulation waveform. In some embodiments, diagnostic assembly 62 is configured to assess the impedance of one or more implantable antennas 240 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 62 is configured to test or otherwise assess the link between one or more implantable antennas 240 and one or more external antennas 540 (e.g. during a procedure in which one or more implantable devices 200 are implanted in a patient). In these embodiments, diagnostic assembly 62 can be configured to perform a test prior to anchoring housing 210 to tissue (e.g. prior to initial or final suturing into tissue such as the fascia layer). For example, lead 265 can be implanted at a location to stimulate target tissue (e.g. one or more nerves identified to treat pain or another patient condition). Prior to suturing housing 210 in its implant location, diagnostic assembly 62 can be configured to confirm that one or more external antenna 540 transmission links to one or more implantable antennas 240 are above an efficiency threshold, for example such that sufficient power will be received by the one or more implantable devices 200. Additionally, the procedure can be performed to optimize or otherwise improve the position of the one or more implantable devices 200 to be implanted and subsequently secured to tissue.

In these link testing embodiments, diagnostic assembly 62 can comprise a handheld assembly (e.g. a sterile assembly comprising a wand or other handheld housing). Diagnostic assembly 62 can be configured to send a simple signal to one or more implantable devices 200 (e.g. a diagnostic assembly 62 with similar power and/or data transmission capabilities as an external device 500). Each implantable device 200 can respond (e.g. via data sent via an implantable antenna 240 or other transmitter) with information related to the quality of the transmission link (e.g. information about the power received by the one or more implantable devices 200). Diagnostic assembly 62 could provide a user interface (e.g. a speaker, a text screen and/or a video display) that provides quality or other information (go/no go information, digital or other discrete level information, and/or analog information). Diagnostic assembly 62 can be further configured to provide information confirming detection of one or more implantable devices 200, status of one or more implantable devices 200 (e.g. parameter level and/or fault detection status), and/or self-diagnostic status (i.e. diagnostic assembly 62 status).

Each implantable device 200 can be configured to specifically identify and/or specifically reply to diagnostic assembly 62 (e.g. in a different form than communications with an external device 500). Each implantable device 200 can be configured to provide information related to one or more of: the charge and/or discharge rate of energy storage assembly 270 (e.g. the charge and/or discharge rate of a capacitor or battery of energy storage assembly 270); or the frequency of a voltage-controlled oscillator that is driven by an unregulated voltage of power converter 233. Diagnostic assembly 62 can be configured to perform numerous performance tests (e.g. of one or more implantable devices 200 or implantation locations for one or more implantable devices 200), prior to completion of the implantation procedure (e.g. prior to closing one or more incisions).

In some embodiments, apparatus 10 is configured to provide a therapy by delivering stimulation energy to tissue, such as electrical energy delivered to tissue by one or more stimulation elements 260 comprising one or more electrodes. Alternatively or additionally, apparatus 10 can be configured as an agent-delivery apparatus (e.g. a pharmaceutical or other agent delivery apparatus). In some embodiments, apparatus 10 comprises one or more reservoirs for storing the agent, such as reservoir 525 of external device 500 and/or reservoir 225 of implantable device 200, each shown in FIG. 1. Reservoirs 525 and/or 225 can be fluidly connected to one or more functional elements 599 and/or functional elements 299, respectively (e.g. via one or more tubes). Reservoirs 525 and/or 225 can comprise one or more chambers (e.g. independent chambers configured to separately contain incompatible drugs or otherwise prevent undesired multiple drug interactions). Reservoirs 525 and/or 225 can comprise a volume (e.g. a volume to store one or more agents) between 0.1 ml and 50 ml, such as between 0.1 ml and 3.0 ml, or between 0.1 ml and 1.0 ml. Reservoirs 525 and/or 225 can comprise pressurized reservoirs or otherwise comprise a fluid pumping mechanism (e.g. a peristaltic mechanism, syringe pump or other fluid pump). Reservoirs 525 and/or 225 and can comprise refillable reservoirs (e.g. when reservoir 225 of an implantable device 200 comprises a valved opening such as a silicone septum or a mechanical valve, either accessible via a needle for refilling). The fluidly attached functional elements 599 and/or functional elements 299 can comprise a fluid delivery element selected from the group consisting of: a catheter; a porous membrane; an iontophoretic element; a needle; and/or combinations of one or more of these. Delivered and/or stored (e.g. in a reservoir) agents can comprise an agent selected from the group consisting of: an analgesic agent such as morphine, fentanyl, lidocaine or other agent delivered to treat pain; a chemotherapeutic agent such as a chemotherapeutic agent delivered systemically (e.g. throughout the blood system of the patient) and/or to a location in or proximate an organ such as the liver or brain to treat cancer; an antibiotic configured to treat or prevent an infection; a hormone such as a hormone delivered intravenously in hormonal therapy; heart medications such as nitroglycerin, a beta blocker or a blood pressure lowering medication; a carbohydrate such as glucose or dextrose delivered to treat a low blood sugar condition; insulin such as to treat a high blood sugar condition; a diabetic medication; a neurological medication; an epilepsy medication; and combinations of one or more of these. In some embodiments, apparatus 10 comprises the one or more agents stored in reservoir 225 and/or 525. In some embodiments, apparatus 10 is constructed and arranged to deliver the agent (e.g. via a catheter-based functional element 599, functional element 299, and/or stimulation element 260) to a patient location selected from the group consisting of: a vessel; a blood vessel; a vein; an artery; heart; brain; liver; spine; epidural space; intrathecal space; subcutaneous tissue; bone; intraperitoneal space, intraventricular space, and combinations of one or more of these.

In some embodiments, an external device 500 is attached to the patient via a patient attachment device 70 comprising a wrist band, wrist watch, leg band, ankle band or other band configured to position an external device 500 about a limb of the patient (i.e. arm or leg of the patient). In these embodiments, one or more implantable devices 200 are implanted under the skin proximate the intended (limb) location of external device 500 and patient attachment device 70. Apparatus 10 can be configured such that external device 500 comprises one or more antennas 540; one or more implantable devices 200 each comprise one or more antennas 240; and each implantable device 200 one or more antennas 240 receive power and/or data from the one or more antennas 540 of the limb-attached external device 500. The limb-attached external device 500 can comprise one or more reservoirs 525 described hereabove and/or one or more functional elements 599 configured as agent delivery elements and/or sensors. The one or more implantable devices 200 can comprise one or more reservoirs 225 described hereabove and/or one or more stimulation elements 260 configured as agent delivery elements and/or sensors.

In some embodiments, apparatus 10 comprises an agent delivery apparatus and agent is delivered into the patient (e.g. into a blood vessel, muscle or subcutaneous tissue) by an external device 500 functional element 599 (e.g. a needle) based on signals recorded by an implantable device 200 functional element 299 and/or stimulation element 260 (e.g. a sensor). Alternatively or additionally, agent can be delivered into the patient (e.g. into a blood vessel, muscle or subcutaneous tissue) by an implantable device 200 stimulation element 260 (e.g. a needle, catheter, porous membrane or iontophoretic delivery element). The amount of agent delivered by stimulation element 260 can be based on signals recorded by an implantable device 200 stimulation element 260 (e.g. a sensor) and/or an external device 500 functional element 599a (e.g. a sensor). External device 500 can provide power to one or more implantable devices 200 and/or it can send data (e.g. sensor data from a functional element 599) to implantable device 200, such as to control agent delivery by implantable device 200.

Apparatus 10 can be configured to prevent an electromagnetic field (e.g. an electromagnetic field produced by one or more devices not included in apparatus 10 and/or other present in the patient environment) from adversely affecting and/or otherwise affecting the patient treatment and/or patient information recording (e.g. patient tissue stimulation and/or patient physiologic information gathering) performed by apparatus 10. Electromagnetic fields from one or more apparatus 10 devices and/or otherwise present in the patient environment can potentially interfere with apparatus 10. The architecture of the wireless signal transmissions of apparatus 10 can be configured to include certain unique and/or identifiable patterns in the signals transmitted by apparatus 10 to confirm (upon receipt) that the signal originated from a component of apparatus 10. Alternatively or additionally, the stimulation signal produced by an implantable device 200 can be created independent from a power signal received from an external device 500, so that any electromagnetic interference in the wireless link does not affect generation and delivery of the stimulation signal. In some embodiments, each implantable device 200 and/or external device 500 includes unique identification codes that are required to be transmitted prior to any changes in stimulation or other implantable device 200 configuration, ensuring correct operation in the presence of interference. Alternatively or additionally, the communication link can incorporate handshaking protocols, confirmation protocols, data encryption and/or scrambling, coding and other security measures to ensure that interfering signals do not adversely affect the implantable system 20 performance (e.g. stimulation). In some embodiments, external system 50 and/or implantable system 20 incorporate electromagnetic absorptive and/or reflective materials to minimize external interference from other sources and/or minimize the probability of apparatus 10 interfering with other systems. Alternatively or additionally, apparatus 10 can incorporate error detection and protocols for entering an alarm state (e.g. and shutting down normal operation) and/or otherwise ensuring safe operation.

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200, via one or more of its stimulation elements 260 (e.g. electrodes) can be configured to provide localized (e.g. targeted) magnetic and/or electrical stimulation. Combined electrical field stimulation and magnetic field stimulation can be applied by using superposition, and this combination can reduce the overall energy requirement. In some embodiments, implantable apparatus 10 comprises one or more stimulation elements 260 comprising a magnetic field generating transducer (e.g. microcoils or cuff electrodes positioned to partially surround or otherwise be proximate to one or more target nerves). Stimulation elements 260 comprising microcoils can be aligned with nerves to minimize affecting non-targeted tissue (e.g. to avoid one or more undesired effects to non-target tissue surrounding or otherwise proximate the target tissue). In some embodiments, the target tissue comprises dorsal root ganglia (DRG) tissue, and the non-target tissue comprises ventral root tissue (e.g. when the stimulation energy is below a threshold that would result in ventral root tissue stimulation).

In some embodiments, external system 50 of apparatus 10 is configured to provide mechanically adjustable alignment of one or more external antennas 540 alignment. Link gain between one or more external antennas 540 and one or more implantable antennas 240 can degrade over time due to physical misalignment of the antennas, relative orientation changes between antennas and/or relative angular misalignment between antennas. In order to compensate for misaligned antennas, electrical beam steering can be included in apparatus 10. Antennas comprising a multi-feed antenna structure and/or those comprising an array of antennas can be incorporated (e.g. into external antenna 540, implantable antenna 240 or both) for electrical beam steering. Alternatively or additionally, mechanical antenna steering can be implemented to physically realign one or more external antennas 540 with one or more implanted antennas 240 (or vice versa). A substrate of an implantable antenna 240 and/or an external antenna 540 can be flexible and/or rigid (e.g. a substrate comprising polyamide, polyimide, liquid crystal polymer (LCP), Rogers, FR4, or a similar material). One or more antennas 540 can be connected to electronics (e.g. a transmitter, receiver or transceiver) using a flexible waveguide or cable (e.g. 50 ohm 0.047 inch coaxial cable designed to provide patient comfort) and/or a flexible PCB substrate transmission line. Mechanical or physical realignment of antennas 240 and/or 540 can be accomplished using one or more of: use of motorized positioners, such as a mechanism including one or more small pulleys and/or tensioners used to translate one or more antennas 240 and/or 540 about one or more axes; an actuator (e.g. a piezoelectric actuator) with directional gears configured to translate one or more antennas 240 and/or 540 about one or more axes; a micro-pump with fluid reservoir (e.g. liquid or gas reservoir) configured to hydraulically and/or pneumatically translate one or more antennas 240 and/or 540 about one or more axes, such as by creating a local pressure difference. In some embodiments, a micro-pump with fluid reservoir is used to move one or more antennas 240 and/or 540, such as to move an external antenna 540 away from tissue to reduce specific absorption rate (SAR). In these embodiments, external antenna 540 can be positioned in mechanical contact with an expandable reservoir (e.g. a balloon) positioned between external antenna 540 and tissue. The reservoir can be inflated or deflated to control separation distance of the external antenna 540 from the patient's skin surface.

In some embodiments, implantable system 20 of apparatus 10 is configured to provide paresthesia-reduced (e.g. paresthesia-free) high frequency pain management and rehabilitation therapy (e.g. via delivery of a stimulation signal above 600 Hz or 1 kHz, or other stimulation signal resulting in minimal paresthesia). Apparatus 10 can be configured to provide both low frequency (e.g. <1 kHz) stimulation and high frequency stimulation, such as when providing low frequency stimulation to elicit feedback from a patient during intraoperative or other (e.g. post-implantation) stimulation configuration. For example, trialing interface 80 and/or 90 can be used during an intra-operative titration of stimulation configuration using low frequency stimulation (e.g. to position and/or confirm position of one or more stimulation elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intraoperative and/or post-implantation titration or other stimulation configuration procedures. Intentional elicitation of paresthesia (e.g. via low frequency stimulation and/or high frequency stimulation) is beneficial during stimulation element 260 (e.g. electrode) implantation because a patient can provide feedback to the implanting clinician to ensure that the stimulation elements 260 are positioned close to the target neuromodulation or energy delivery site. This implantation position-optimizing procedure can advantageously reduce the required stimulation energy due to stimulation elements 260 being closer to target tissue, since a minimum threshold for efficacious stimulation amplitude is proportional to the proximity of stimulation elements 260 to target tissue (e.g. target nerves). The patient can inform the clinician of the sensation of paresthesia coverage, and the clinician can adjust stimulation element 260 position to optimize stimulation element 260 location for efficacious treatment while minimizing unintentional stimulation of non-target tissue (e.g. motor nerves or other nerves which are not causing the patient's pain). These paresthesia-inducing techniques (e.g. using low frequency stimulation and/or high frequency stimulation) can be used during or after implantation of one or more implantable devices 200.

In some embodiments, apparatus 10 is configured to deliver low frequency stimulation energy (e.g. electrical energy comprising a low frequency signal) to stimulate motor nerves, such as to improve tone and structural support (e.g. physical therapy). In these embodiments, apparatus 10 can be further configured to provide high frequency stimulation, such as to treat pain (e.g. suppress and/or control pain). The combined effect can be used not only for pain management but also muscle strengthening and gradual healing of supportive structures. Alternatively or additionally, as described herein, apparatus 10 can be configured to deliver low frequency stimulation energy (e.g. electrical energy) to induce paresthesia, which can also be accompanied by the delivery of high frequency stimulation (e.g. to suppress and/or control pain). In some embodiments, apparatus 10 is configured to deliver low frequency stimulation (e.g. electrical energy comprising a low frequency signal) and burst stimulation, delivered simultaneously or sequentially. The low frequency stimulation and the burst stimulation can be delivered on similar and/or dissimilar stimulation elements 260 (e.g. similar or dissimilar electrode-based stimulation elements 260).

As described herein, apparatus 10 can be configured for treating numerous disease and disorders, such as when apparatus 10 is configured to deliver electrical or other stimulation energy to treat pain (e.g. by delivering electrical or other energy to the spine or other neural location). Apparatus 10 can be configured to stimulate tissue with various stimulation waveforms, such as those described in applicant's co-pending U.S. patent application Ser. No. 17/372,095, titled "Apparatus with Enhanced Stimulation Waveforms", filed Jul. 9, 2021.

Apparatus 10 can be configured to treat neuropathy, neuralgia and/or other nerve pain that is related to: surgery; trauma; infection (e.g. a herpetic infection); and/or diabetes (e.g. diabetic neuropathy). One or more stimulation elements 260 can be configured to deliver stimulation energy (e.g. electrical energy, magnetic energy, light energy, thermal energy, sound energy, and/or chemical energy (e.g. energy from a drug or reagent) to nerve tissue such as tissue of the central nervous system and/or peripheral nervous system. One or more leads 265 (each comprising one or more stimulation elements 260) can be implanted in and/or proximate the spinal cord, the groin and/or a joint such as the hip. For example, apparatus 10 can be configured to treat one or more of: post-surgical neuralgia (e.g. following hernia repair such as a hernia repair including an implanted mesh); headache (e.g. due to occipital neuralgia); post-herpetic neuralgia; chronic pelvic and/or hip pain; knee pain; and combinations of one or more of these.

To treat pain related to hernia or hernia repair, one or more stimulation elements 260 (e.g. on a lead 265 and/or on a housing 210) can be positioned to stimulate tissue of the peripheral nervous system and/or the central nervous system. In some embodiments, one or more stimulation elements 260 are positioned to stimulate the cutaneous branch of the ilioinguinal, inguinal and/or genital branch of the genitofemoral nerves. In some embodiments, one or more stimulation elements 260 are positioned to stimulate corresponding branches of spinal nerves correlating to one or more dermatomes related to pain associated with at least one of hernia or hernia repair.

Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these. In some embodiments, apparatus 10 is configured to treat hernia pain by delivering a low frequency stimulation signal (e.g. an electrical signal less than or equal to 1 kHz delivered by one or more electrode-based stimulation elements 260). Alternatively or additionally, apparatus 10 can treat hernia pain with a high frequency stimulation signal, such as a signal comprising a frequency greater than 1 kHz. Stimulation can be accomplished either via subcutaneous field stimulation and/or by stimulation elements 260 positioned adjacent or at least near the nerves and/or their branches. In some embodiments, stimulation is accomplished transvascularly (e.g. stimulation including low and/or high frequencies).

The apparatus of the present inventive concepts can be configured to stimulate the ilioinguinal nerve, genitofemoral nerve and/or iliohypogastric nerves, such as to ameliorate pain following hernia repair. One or more leads 265 (e.g. one or more leads 265 comprising one or more electrode-based or otherwise stimulation-based stimulation elements 260) can be inserted over the inguinal region (which may include the inguinal ring) to stimulate any or all three of these nerves (e.g. in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more stimulation elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g. the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g. transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g. percutaneous or paddle) including stimulation-based stimulation elements 260 can be placed over the dorsal columns, over the dorsal roots and/or in the dorsal root entry zone, in a unilateral, bilateral and/or midline fashion.

To treat occipital neuralgia, also known as C2 neuralgia, one or more stimulation elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more stimulation elements 260, are implanted transversely, either unilaterally or bilaterally, at the level of the appropriate target cervical nerve (C1, C2, etc.). The C1, 2, 3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more stimulation elements 260 are positioned to stimulate the trigeminal and/or occipital nerves. One or more leads 265 can be anchored to the fascia proximate the tissue to be stimulated.

To treat post-herpetic neuralgia (e.g. neuralgia associated with shingles), one or more stimulation elements 260 can be positioned to stimulate corresponding branches of the spinal nerves and/or peripheral nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; accidental bowel leakage; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain;

anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g. using bilateral and/or unilateral stimulation) one or more of the targets listed below.

In some embodiments, the stimulated targets include the sacral nerves (roots) S2, S3 and/or S4. One or more leads 265 (e.g. each including one or more stimulation-delivering stimulation elements 260) can be positioned to stimulate any or all of the three roots, on a single side or both sides, in any bilateral or unilateral combination. The roots can be accessed, with the patient lying in the prone position, by positioning one or more leads 265 (e.g. percutaneously), with or without the use of fluoroscopy, ultrasound or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal, and spanning one or more foramina.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound or other imaging modality), up to the cauda equina, where the S2, S3 and/or S4 roots can be stimulated where they enter the spinal cord, and/or the conus medullaris can be stimulated directly (e.g. in the same location).

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals and urethra. Pelvic and voiding disorders can be treated by stimulating pudendal nerve fibers. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g. fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g. through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g. fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g. voiding dysfunction). In order to provide stimulation of the tibial nerve, lead 265 can be inserted at a location close to the knee and/or at a location near the ankle. For example, the tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down procedure can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g. a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e. stimulation energy delivered from inside a blood vessel to nerve tissue proximate the blood vessel), such as via the femoral vein and/or artery, each of which provide intraluminal access to many other blood vessels (e.g. using standard interventional techniques). The tibial nerve can be transvascularly stimulated by the popliteal vein and/or artery (e.g. by placing one or more stimulation elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat pelvic dysfunction, overactive bladder, and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more stimulation elements 260 are positioned to stimulate tissue of the central nervous system or tissue and/or tissue of the peripheral nervous system to treat overactive bladder, such as to stimulate one or more nerves that control and/or are otherwise related to bladder function (e.g. to increase bladder capacity, improve bladder emptying, reduce urge incontinence and/or reduce stress incontinence). For example, one or more stimulation elements 260 are be positioned to stimulate tibial nerve tissue and/or sacral nerve tissue (e.g. at least the S3 nerve root) to treat overactive bladder. In some embodiments, one or more stimulation elements 260 can be positioned to stimulate sacral nerve tissue to treat urinary urgency, urinary frequency (e.g. urinary urgency frequency), and/or painful bladder syndrome. In some embodiments, lead 265 is constructed and arranged to be positioned along one or more locations of the tibial nerve, such as a positioning performed using percutaneous technique (e.g. when lead 265 comprises a cylindrical SCS-type lead) and/or surgical (cut-down) techniques (e.g. when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g. transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more stimulation elements 260 are positioned proximate (e.g. in contact) with the sacral nerve root(s). The housing 210 can be placed anywhere in the groin, perineum, scrotum, pelvis, hip, thigh, leg, behind the knee, buttocks, abdomen and/or low back. Lead 265 (e.g. a lead 265 comprising a lead extension) can be extended underneath the skin (e.g. tunneled) to a second incision (e.g. across the flank to the lower abdomen, across the midline to the buttocks, or low back), and a third incision can be made (e.g. in the abdomen, back or buttocks) where housing 210 can be inserted and connected to lead 265. Alternatively, housing 210 can be inserted at another internal location. If lead 265 is already connected (e.g. attached in manufacturing) to housing 210, lead 265 can be advanced in the opposite direction, such as from the third incision, to the second incision, to the first incision (if three incisions are made), or housing 210 can be advanced under the tissue from incision 1 to incision 2 or from incision 2 to incision 3. In some embodiments, only 1 or 2 incisions are performed. In some embodiments, such as when lead 265 is already connected (e.g. attached in manufacturing) to housing 210, lead 265 and housing 210 are implanted. In some embodiments, a first lead 265 and a first housing 210 (pre-attached or attachable) are utilized in a dose titration or other "trialing procedure" (also referred to as a "trialing session" herein), and a second lead 265 and housing 210 (pre-attached or attachable) are implanted in the patient for subsequent treatment of the patient.

In some embodiments, one or more stimulation elements 260 are positioned to perform posterior tibial nerve stimulation (PTNS), such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more stimulation elements 260 are positioned to perform retrograde stimulation of the sacral nerve plexus and restore the balance between bladder inhibitory and excitatory control systems of the bladder. One or more stimulation elements 260 can be positioned above the ankle, proximate and/or into the tibial nerve. Implantable device 200 can deliver stimulation energy to the stimulation elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, implantable system 20 is configured to deliver a series of repeated stimulation periods, such as a regimen of approximately: weekly thirty-minute sessions of stimulation for twelve weeks. In some embodiments, implantable system 20 is configured to provide weekly, daily and/or hourly sessions that deliver stimulation for between 10 minutes and 60 minutes. Implantable system 20 can deliver stimulation for any number of minutes per day. In some embodiments, apparatus 10 is configured to achieve an approximate 50% reduction in urinary urge incontinence and/or urinary urgency/frequency episodes.

In some embodiments, apparatus 10 is configured to provide temporary stimulation of tissue to treat overactive bladder, such as by using trialing interface 80 and/or 90 described hereabove, such as to provide power and/or data to one or more implantable devices 200 to confirm acceptable improvement of the patient's overactive bladder (e.g. successful stimulation of one or more sacral nerves, tibial nerves or other tissue), before closing an incision or otherwise fully implanting one or more implantable devices 200. In some embodiments, a temporary stimulation (for overactive bladder or in a trialing procedure for any therapy) is provided for up to one week, up to one month, more than 1 month, more than 2 months, or more than 3 months. In some embodiments, one or more implantable devices 200 are left in place if the temporary stimulation period is successful or unsuccessful (e.g. left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more stimulation elements 260 are positioned to stimulate periurethral muscles. In some embodiments, one or more stimulation elements 260 are positioned to stimulate tissue of the vagina or anus. In some embodiments, one or more stimulation elements 260 are positioned to stimulate sphincter muscles for controlling the bladder, such as two stimulation elements 260 positioned on either side of the urethral orifice. In these embodiments, housing 210 can be implanted in suprapubic region or in the perineum. In some embodiments, lead 265 comprises (e.g. on a distal portion) a pessary ring comprising two stimulation elements 260. In some embodiments, stimulation elements 260 comprise periurethral electrodes configured to stimulate pudendal afferents.

As described above, apparatus 10 can be configured for treating numerous diseases, disorders or other undesirable patient conditions, such as fecal incontinence. Injury of nerves that sense stool in the rectum can lead to fecal incontinence. In some embodiments, one or more stimulation elements 260 (e.g. one or more electrical, magnetic, light or other energy delivery elements) of one or more leads 265 and/or one or more implantable devices 200 are configured to stimulate tissue to treat fecal incontinence, such as to treat tissue selected from the group consisting of: sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more stimulation elements 260 are configured to deliver energy to sacral nerve or other tissue.

In some embodiments, apparatus 10 is configured to treat fecal incontinence, overactive bladder (i.e. overactive bladder and/or urinary incontinence), and/or pelvic disorders, and implantable device 200: comprises between 1 and 16 stimulation elements 260, such as four or more electrodes; delivers electrical stimulation energy at a range of approximately between 10 Hz and 15 Hz (or a range of between 5 Hz and 25 Hz); delivers electrical stimulation energy with a pulse width of approximately between 180 μsec and 240 μsec (or between 1 μsec and 200 μsec); provides electrical stimulation energy with an amplitude of approximately 0.1V to 8.5V (e.g. providing a current between 0.1 mA to 10 mA, which can be adjusted in increments between 0.01 mA and 0.1 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; or an on time of several hours followed by an off time of several hours (such as 8 hours of stimulation ON and 16 hours of stimulation OFF or 16 hours on and 8 hours off, and 12 hour on and 12 hours off; delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more stimulation elements 260 (e.g. small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratroclear; sphenopalantine (SPG); and combinations of one or more of these.

In some embodiments, apparatus 10 is configured to treat neuralgia, such as a neuralgia resulting from surgery (e.g. groin, shoulder, lung and/or amputation), trauma and/or phantom pain, and one or more stimulation elements 260 are positioned to stimulate nerve tissue.

In some embodiments, apparatus 10 is configured to treat neuralgia, such as a neuralgia resulting from groin surgery (e.g. hernia or other groin surgery), and one or more stimulation elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more stimulation elements 260 are positioned to stimulate axial nerve tissue (e.g. one or more stimulation elements 260 positioned on a lead 265 implanted in a suprascapular location).

In some embodiments, apparatus 10 is configured to treat neuralgia, such as a neuralgia resulting from lung surgery, and one or more stimulation elements 260 are positioned to stimulate intercostal nerve tissue.

In some embodiments, apparatus 10 is configured to treat neuralgia, such as a neuralgia associated with carpal tunnel syndrome, and one or more stimulation elements 260 are positioned to stimulate median nerve tissue.

In some embodiments, apparatus 10 is configured to treat neuralgia, such as a neuralgia associated with temporomandibular joint disorder (TMJ), and one or more stimulation elements 260 are positioned to stimulate V2 of trigeminal nerve tissue.

In some embodiments, apparatus 10 is configured to treat neuralgia, such as a facial neuralgia, and one or more stimulation elements 260 are positioned to stimulate trigeminal nerve tissue.

In some embodiments, apparatus 10 is configured to treat neuralgia, such as a leg (sciatic) neuralgia, and one or more stimulation elements 260 are positioned to stimulate nerve tissue proximal a contributing lesion.

In some embodiments, apparatus 10 is configured to treat pelvic pain, such as interstitial cystitis and/or bladder pain, and one or more stimulation elements 260 are positioned to stimulate peripheral nervous system tissue (e.g. pudendal tissue and/or S-2, S-3 and/or S-4 roots) and/or central nervous system tissue (e.g. lower spinal cord and/or S3 neural foramen).

In some embodiments, apparatus 10 is configured to treat pelvic pain, such as anal pain, and one or more stimulation elements 260 are positioned to stimulate peripheral nerve tissue such as pudendal tissue and/or S-2, S-3 and/or S-4 roots.

In some embodiments, apparatus 10 is configured to treat subcutaneous pain, and one or more stimulation elements 260 (e.g. paddle electrodes) are positioned to stimulate nerve tissue.

In some embodiments, apparatus 10 is configured to treat diabetic neuropathy, such as painful diabetic neuropathy, and one or more stimulation elements 260 are positioned proximate the lower spinal cord (e.g. to stimulate S3 nerves) or other body location to stimulate nerve tissue.

In some embodiments, apparatus 10 is configured to treat visceral pain, angina and/or other pain, and one or more stimulation elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g. such that one or more stimulation elements 260 are positioned proximate the nerve to be stimulated). In some embodiments, lead 265 is positioned to stimulate the dorsal root ganglia to treat diabetic neuropathy (e.g. diabetic neuropathy of the hand and/or foot). Lead 265 can be implanted percutaneously and/or surgically as described herein. Lead 265 and/or one or more stimulation elements 260 can comprise a paddle electrode, such as one or more paddle electrodes implanted in the foot, leg and/or arm. Lead 265 and/or one or more stimulation elements 260 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g. to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of trunk, neck, head, back, foot, leg, arm and/or hand disorders.

One or more leads 265 (e.g. each including one or more stimulation elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibular (peroneal) innervates top of both medial and lateral foot. In some embodiments, stimulation element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius and soleus muscles where it can be accessed surgically or percutaneously. It then surfaces just as it warps around the anterior aspect of the medial malleolus where it supplies the medial posterior foot in front of heel. The medial sural cutaneous nerve comes off the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more stimulation elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more stimulation elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 is configured to transvascularly stimulate at least one of a median nerve, an ulnar nerve or a radial nerve, and stimulation element 260 comprises one or more electrodes positioned in a vessel selected from the group consisting of: brachial vein; brachial artery; basilic vein; basilic artery; deep vein of the arm; deep artery of the arm; and combinations of one or more of these. In some embodiments, apparatus 10 is configured to transvascularly stimulate at least one of a median nerve or an ulnar nerve, and stimulation element 260 can comprise one or more electrodes positioned in a vessel selected from the group consisting of: brachial vein; brachial artery; and combinations of one or more of these. In some embodiments, apparatus 10 is configured to transvascularly stimulate the radial nerve, and stimulation element 260 comprises one or more electrodes positioned in a vessel selected from the group consisting of: deep vein of arm; deep artery of arm; basilic vein; radial collateral vein; radial collateral artery; medial collateral vein; medial collateral artery; radial vein;

radial artery; and combinations of one or more of these. In some embodiments, apparatus 10 can be configured to transvascularly stimulate the medial cutaneous nerve, and stimulation element 260 comprises one or more electrodes positioned in the basilic vein. In some embodiments, apparatus 10 is configured to transvascularly stimulate the ulnar nerve, and stimulation element 260 comprises one or more electrodes positioned in a vessel selected from the group consisting of: ulnar collateral vein; ulnar collateral artery; ulnar vein; ulnar artery; and combinations of one or more of these. In some embodiments, apparatus 10 is configured to transvascularly stimulate the median nerve, and stimulation element 260 can comprise one or more electrodes positioned in a vessel selected from the group consisting of: brachial vein; brachial artery; ulnar vein; ulnar artery; and combinations of one or more of these.

As described herein, one or more leads 265 can be positioned to stimulate the spinal cord, such as via percutaneous insertion of a lead 265 in the epidural space or surgical implantation of the lead 265 (e.g. a paddle lead) in the epidural space. A lead 265 can be placed such that one or more stimulation elements 260 (e.g. one or more electrodes) are positioned from T5-S5, such as to capture the area of pain or reduced circulation of the leg or foot. One or more stimulation elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more stimulation elements 260 (e.g. one or more electrodes attached to one or more leads 265) can be positioned to transvascularly stimulate one or more nerves, such as one or more nerves in the foot, leg and/or arm, such as when the one or more stimulation elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more stimulation elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more stimulation elements 260 (e.g. one or more electrodes attached to one or more leads 265) can be positioned to stimulate dorsal root ganglia that supply the following nerves (e.g. to treat the leg and/or foot): common peroneal (L4-S2); tibial (L4-S3); femoral (L2-L4); and combinations of one or more of these. One or more stimulation elements 260 (e.g. one or more electrodes attached to one or more leads 265) can be positioned to stimulate dorsal root ganglia that supply the following nerves (e.g. to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e., stump pain), such as by using a high frequency alternating current (HFAC) block approaches. In these embodiments, one or more leads 265 can be implanted such that one or more stimulation elements 260 stimulate one or more nerves in the leg, arm and/or sacrum. One or more leads 265 can be surgically implanted, such as when lead 265 comprises a paddle electrode positioned near a nerve in the foot, leg or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg or arm, such as when one or more stimulation elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g. which arise from C2 and C3); the greater and/or lesser auricular nerves (e.g. which also arise from C2/C3); the third (least) occipital nerve (e.g. which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g. a cylindrical SCS-type lead) can be inserted percutaneously either subcutaneously or under the muscle. Alternatively, surgery (e.g. direct cut-down) can be performed to insert lead 265 (e.g. a cylindrical lead, a paddle lead, a cuff or hemi-cuff electrode) proximate, one and/or around these nerves. Alternatively or additionally, the nerves can be accessed transvascularly as described herein (e.g. when one or more stimulation elements 260 are implanted in a blood vessel). Housing 210 can be implanted anywhere in the head under the skin, including: behind the ear, back of the head, the neck, in the face, and the like, where one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210 can be placed anywhere in the head under the skin, as described herein.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approaches. In these embodiments, one or more leads 265 can be implanted such that one or more stimulation elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg, torso and/or arm, such as when one or more stimulation elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these. In these embodiments, apparatus 10 can be configured to deliver stimulation to median nerve tissue; ulnar nerve tissue and/or radial nerve tissue.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations of one or more of these.

In some embodiments, apparatus 10 is configured to treat knee pain. Knee pain from joint degeneration or join replacement surgery can be treated via stimulation of the nerves innervating the knee and/or via stimulation of the tissue surrounding the knee (sometimes referred to as peripheral field stimulation). Apparatus 10 can comprise between one and eight leads 265 whose stimulation elements 260 are placed near and around the knee. In some embodiments, four leads 265 are placed, in locations medial, lateral, superior and inferior to the knee. The leads 265 can be placed subcutaneously for field stimulation, or they can be placed directly adjacent to specific nerve targets. Applicable nerve targets are as follows: medial knee can include medial femoral cutaneous and infrapatellar cutaneous branches of saphenous nerve; lateral knee can include constant articular branches of common peroneal, lateral retinacular nerve; anterior knee can include lateral, medial, and anterior cutaneous femoral nerve, infrapatellar branch of saphenous nerve, medial and lateral retinacular nerve and articular branches of peroneal nerve; posterior knee can include obturator, posterior tibial and sciatic nerves. In addition, the following nerves can be stimulated via stimulation elements 260 to treat knee pain: nerves arising from the tibial nerve such as the superior, middle and inferior genicular nerves; nerves arising from the common peroneal such as the superior lateral, inferior lateral, and recurrent genicular nerves; and nerves arising from the obturator nerve such as the genicular branch of obturator; and nerves arising from the femoral nerve such as the saphenous nerve. Each of these targets can be stimulated transvascularly by one or more stimulation elements 260.

In some embodiments, implantable device 200 has an internal battery or other power supply such that stimulation (e.g. stimulation energy and/or a stimulation agent) is delivered to one or more locations within a patient for an extended time period (e.g. at least 1 hour, at least 1 day, at least 1 month or at least 1 year), without receiving a power transmission (e.g. as described herein from an external device such as external device 500) during that time period. In some embodiments, at least a portion of a single pulse of energy (e.g. at least a single phase) is delivered by implantable device 200 using energy provided by an internal power supply 570 such as a battery or a capacitor. In these embodiments, data can be transmitted by one or more of an external device 500 and/or a programmer 600, such as to activate or modify stimulation being delivered, with or without also transmitting power.

In some embodiments, implantable device 200 comprises one or more components configured to receive transmitted power (e.g. via an external device 500), receive transmitted data (e.g. via an external device 500 and/or programmer 600) and/or deliver stimulation (e.g. deliver stimulation energy and/or a stimulation agent).

In some embodiments, one or more implantable devices 200 are configured to deliver stimulation energy (e.g. via one or more stimulation elements 260 comprising an electrode) with a stimulation waveform comprising one or more high frequency signals (e.g. a signal comprising one or more high frequency components). For example, one or more implantable devices 200 can deliver one or more stimulation waveforms comprising one or more signals above 600 Hz, such as one or more signals above 1.0 kHz, 1.2 kHz, 5 kHz, 10 kHz or 25 kHz.

In these embodiments, the delivered stimulation waveform can be configured to be void of (i.e. not include) one or more lower frequency signals, such as by not including any signals at a frequency below 100 Hz, below 500 Hz, below 1000 Hz, below 1200 Hz or below 1500 Hz.

One or more implantable devices 200 can be configured to deliver stimulation energy with a stimulation waveform that varies over time. In some embodiments, one or more stimulation parameters of the stimulation waveform are randomly varied over time, such as by using a probability distribution as described in applicant's co-pending U.S. patent application Ser. No. 17/372,095, titled "Apparatus with Enhanced Stimulation Waveforms", filed Jul. 9, 2021. Each stimulation waveform can comprise one or more pulses, such as a group of pulses that are repeated at regular and/or irregular intervals. In some embodiments, a pulse can comprise delivery of electrical energy, such as electrical energy delivered in one or more phases (e.g. a pulse comprising at least a cathodic or anodic portion followed by passive capacitive recovery with an optional open circuit time between the first portion and recovery). In some embodiments, a group of pulses is delivered, each pulse comprising an anodic or cathodic portion that can include charge recovery after each pulse, such as charge recovery comprising active (opposite polarity pulse) recovery, and/or passive (capacitive) recovery. In some embodiments, there is no recovery between pulses, but instead active or passive recovery is included at the end of the set of the first (anodic or cathodic) portions. In some embodiments, single or groups of pulses are provided at time-varying modes of repetition (e.g. regular intervals for a period, then a period of irregular intervals) or at regular intervals with occasional (random) spurious pulses inserted (creating a single irregular event in an otherwise regular series). Non-limiting examples of waveform variations include: a variation in frequency (e.g. frequency of one or more signals of the waveform); variation of a signal amplitude; variation of interval time period (e.g. at time period between pulses or a time period between pulse trains); variation of a pulse width; multiple piecewise or continuous variations of one of more stimulation parameters in a single pulse (e.g. multi-step, multi-amplitude in one "super-pulse"); variation of pulse symmetry (e.g. via active drive, passive recovery and/or active-assisted passive recovery); variation of stimulation energy over a time window and/or overlapping time windows; variation of the power in the frequency spectrum of the stimulation waveform; and combinations of one or more of these. In some embodiments, apparatus 10 and/or implantable device 200 can be configured to vary a stimulation waveform "systematically" (e.g. automatically and/or at least semi-automatically by apparatus 10) such as a variation performed temporally (e.g. on predetermined similar or dissimilar time intervals) and/or a variation performed based on a parameter, such as a measured parameter that can be based on a signal produced by a sensor of implantable device 200 or another component of apparatus 10. Alternatively or additionally, apparatus 10 and/or implantable device 200 can be configured to vary a stimulation waveform randomly. Random variation shall include discrete or continuous variations that can be selected from a distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. Random pulses or groups of pulses can be generated based on randomly varying one or more stimulation signal parameters. One or more stimulation parameters can be varied randomly through the use of one or more probability distributions, as described herebelow.

In some embodiments, the amplitude of a signal delivered by one or more implantable devices 200 is adjusted to prevent discomfort to the patient (e.g. paresthesia or other undesired condition) from the stimulation signal. In some embodiments, the amplitude of the stimulation signal can be ramped (e.g. up and/or down), a single time or multiple times (e.g. continuously or intermittently). In some embodiments, a titration procedure is performed to set (e.g. define) one or more stimulation parameters based on avoiding patient discomfort.

In some embodiments, one or more implantable devices 200 are configured to deliver stimulation energy (e.g. via one or more stimulation elements 260 comprising an electrode) with a stimulation waveform comprising one or more waveform patterns. The stimulation waveforms delivered can be configured to treat various conditions of a patient. Each stimulation waveform can comprise a series of continuous pulses, intermittent pulses, and/or spurious pulses (e.g. occasional events in an otherwise continuous stream). Each pulse can comprise a pulse train that is repeatedly delivered by implantable device 200, the train comprising one or more cathodic pulses and/or one or more anodic pulses. In some embodiments, implantable device 200 delivers a multiphasic pulse comprising at least two cathodic pulses and/or anodic pulses, with or without any time between each pulse. For example, implantable device 200 can deliver a biphasic pulse comprising a cathodic pulse followed by an anodic pulse, a triphasic pulse comprising a cathodic pulse followed by an anodic pulse followed by a second cathodic pulse, or any series of two or more cathodic and/or anodic pulses. In some embodiments, delivered pulses are exponential in nature (e.g. comprise an exponential portion), such as dynamic return pulses that exceed a minimum current (e.g. at least 1 mA, 10 mA or 50 mA) for a short duration (e.g. for approximately sec), and then decay to lower current levels (e.g. a level of approximately 100 nA), with a time constant on the order of 1 μsec to 100 μsec.

The stimulation waveforms delivered by implantable device 200 can comprise one or more high frequencies. The stimulation waveform frequency or other stimulation parameter can be set, adjusted, and/or modified ("set", "adjusted", and/or "modified" herein) to optimize therapeutic benefit to the patient and minimize undesired effects (e.g. paresthesia or other patient discomfort). In some embodiments, a stimulation waveform is adjusted based on a signal produced by a sensor of apparatus 10 (e.g. a sensor of implantable device 200, such as a stimulation element 260 configured as a sensor or other sensor of implantable device 200 as described hereabove). Adjustment of a stimulation waveform parameter can be performed automatically by the implantable device 200 and/or via an external device 500 and/or programmer 600).

In some embodiments, a pulse shape of a stimulation waveform can be varied, such as a pulse shape comprising: a sinusoidal geometry; a square geometry (e.g. a waveform comprising a square wave); a rectangular geometry; a triangular geometry; (e.g. symmetric or asymmetric); a trapezoidal geometry; a sawtooth geometry; a ramped geometry; an exponential geometry; a piece-wise step function geometry; a root-raised cosine geometry; and combinations of one or more of these.

In some embodiments, a charge recovery phase (e.g. anodal phase) of a stimulation waveform is varied by implantable device 200.

Inter-pulse gap, the time between one or more pulses (e.g. a biphasic or other multiphasic pulse that is repeated continuously), can be varied systematically and/or randomly by implantable device 200. In some embodiments, inter-pulse gap between one or more pulses comprises zero time (i.e. a first pulse is immediately followed by a similar or dissimilar second pulse). In some embodiments, inter-pulse gap is varied systematically, such as on a routine basis (i.e. temporally) and/or varied based on a signal produced by a sensor of apparatus 10. Alternatively or additionally, inter-pulse gap can be varied randomly, such as a random variation based on a distribution (e.g. a probability distribution with a pre-determined shape) as described herebelow.

In some embodiments, implantable device 200 delivers a stimulation waveform comprising a series of frequency modulated (FM) pulses, such that the frequency of stimulation varies. Implantable device 200 can be configured to deliver a frequency modulated stimulation waveform comprising a carrier signal, at a carrier frequency, that is modulated continuously between a first frequency and a second frequency. For example, implantable device 200 can deliver a stimulation waveform that modulates between 2.0 kHz and 3.0 kHz every second (e.g. comprising a carrier signal at 2.5 kHz that is modulated at 1 Hz) with a modulation range (the excursion from the carrier signal) of +/−500 Hz. In some embodiments, implantable device 200 can deliver a stimulation waveform that comprises: a carrier frequency between 1 kHz and 50 kHz, a modulation frequency between 0.1 Hz and 10 kHz and/or a modulation range between 1 Hz and the carrier frequency.

In some embodiments, implantable device 200 delivers a stimulation waveform comprising a series of amplitude modulated (AM) pulses, such that the amplitude of stimulation varies (e.g. varying the amplitude of the voltage and/or current of the stimulation signal). The amplitude of delivered current can be varied in a single amplitude modulated sweep, such as a sweep from 2 mA to 3 mA. In some embodiments, amplitude of a signal can be varied continuously, such as when current is varied between 2 mA and 3 mA every second (e.g. a signal comprising a modulation frequency of 1 Hz). In these embodiments, the depth of modulation would be 33%, where depth of modulation is equal to 1−[lower range/upper range]. In some embodiments, amplitude of delivered current fluctuates between 1 mA and 3 mA (i.e. a depth of modulation of 66%), while in other embodiments, current fluctuates between 0 mA and 10 mA (e.g. a depth of modulation of 100%). In some embodiments, implantable device 200 is configured to deliver an amplitude modulated signal comprising: a carrier frequency between 1 Khz and 50 kHz; a modulation frequency between 0.1 Hz and the carrier frequency and/or a depth of modulation between 0.1% and 100%.

In some embodiments, implantable device 200 delivers a stimulation waveform comprising delivery of continuously balanced analog current waveforms, for example from a differential Howland current source. In these embodiments, there are not independent pulses, but rather there is true analog frequency and amplitude modulation. Periods of delivering stimulation (or presence of balanced differential analog stimulation) and periods of no stimulation (e.g. a quiescent period) can be included. In some embodiments, controller 250 comprises one or more reconfigurable stimulation blocks including one or more Howland or other current sources. The one or more current sources (e.g. two or more current sources) can each be attached to a stimulation element 260 (e.g. in a monopolar configuration when the current source is also connected to housing 210 or in a bipolar configuration when the current source is connected to a pair of stimulation elements 260). Alternatively, controller 250 can comprise one or more current sources that are attached to a matrix of switches that selectively connect the one or more current sources to multiple stimulation elements 260 (e.g. connect a single current source to 2, 4, 8, 12 or 16 electrodes). In some embodiments, controller 250 is configured such that a stimulation waveform signal provided to the current source passes through a capacitor (e.g. capacitor C1 shown), the capacitor providing DC balance.

In some embodiments, implantable device 200 delivers a stimulation waveform comprising delivery of multiple trains of pulses that are delivered intermittently, a "burst stimulation" waveform as defined hereabove. For example, implantable device 200 can be configured to deliver a series or train of five pulses, each with a 1 msec pulse width. The each of the five pulses can be separated by an inter-pulse gap of 4 msec, creating a train-on period of 16 msec. These five pulses can be repeated every 25 msec (the "inter-train period"). In some embodiments, implantable device 200 can be configured to deliver a burst stimulation waveform comprising a pulse width between 5 µsec and 1 msec. Implantable device 200 can deliver a train or burst stimulation waveform comprising pulses with constant pulse widths and/or varying pulse widths, such as when the pulse widths (and/or other stimulation parameters) are varied randomly and/or systematically. Implantable device 200 can deliver a train or burst stimulation waveform with a varied or constant pulse shape selected from the group consisting of: sinusoid; square, rectangle; triangle (symmetric or asymmetric); trapezoid; sawtooth; ramp (e.g. a linear ramp); exponential curve; piece-wise step function; and combinations of one or more of these. Implantable device 200 can deliver a train or burst stimulation waveform with an inter-pulse gap less than inter-train period. The inter-pulse gap can be relatively constant, and/or it can be varied, such as when implantable device 200 randomly varies the inter-pulse gap or varies the inter-pulse gap systematically. In some embodiments, the inter-pulse gap between any two pulses within a pulse train (or burst) can be varied between 0.1 µsec and the inter-train period (or inter-burst period). Implantable device 200 can deliver a train stimulation waveform with an inter-pulse gap between 1 µsec and 1 second. Implantable device 200 can deliver a burst stimulation waveform with an inter-train period between 1 µsec and 1 second. Implantable device 200 can deliver a burst stimulation waveform with an inter-burst period between 20 µsec and 24 hours. The inter-burst period can be relatively constant, and/or it can be varied, such as when implantable device 200 randomly varies the inter-burst period or varies the inter-burst period systematically. In some embodiments, inter-burst period is varied by the user, such as via a user using programmer 600. In these embodiments, user activation can be regulated with one or more safeguards or other limits such as those incorporated into patient-controlled analgesia devices. The inter-train period can be varied between 1 µsec and 24 hours. Implantable device 200 can deliver a train or burst stimulation waveform with a train-on period (the time between the onset of a first pulse in a pulse train to the end of the last pulse in a pulse train) between 10 µsec and 24 hours. The train-on and/or burst-on period can be relatively constant, and/or it can be varied, such as when implantable device 200 randomly varies the train-on and/or burst-on period or varies the train-on and/or burst-on period systematically. Implantable device 200 can deliver a train or burst stimulation waveform with a train or burst envelope selected from the group consisting of: cosine; cosine-squared; sine; square; rectangle; triangle (symmetric or asymmetric); trapezoid: sawtooth; ramp (e.g. linear ramp); and combinations of one or more of these. Implantable device 200 can deliver a train and/or burst stimulation waveform with a train ramp duration or burst ramp duration between 1 µsec to 10 minutes. Implantable device 200 can deliver a train and/or burst stimulation waveform with a depth of modulation between train and/or bursts of between 1% and 99%. For example, between some or all of the trains and/or bursts (burst-off or train-off periods), a signal may be present and may contain the same or different elements contained in the train-on and/or burst-on period. These burst-off or train-off periods may comprise a quiescent period. The amplitude of the signal contained in these quiescent periods can be from 0% to 99% of the signal amplitude during the train-on and/or burst-on period, such as a signal with an amplitude less than 50% of the signal amplitude during the train-on and/or burst-on period or another amplitude below a neuronal excitation threshold.

In some embodiments, apparatus 10 is configured to deliver stimulation energy to dorsal root ganglion and/or spinal cord tissue to treat a condition such as pain. In these and other embodiments, apparatus 10 can be configured to provide a stimulation waveform comprising: a combination of low frequency stimulation (e.g. electrical energy comprising a low frequency signal) and burst stimulation; burst stimulation (e.g. burst stimulation alone); a combination of low frequency stimulation and high frequency stimulation; a combination of low frequency stimulation, high frequency stimulation and burst stimulation; and combinations of one or more of these. The stimulation energy provided by apparatus 10 can be delivered to tissue via one or more stimulation elements 260, such as two or more electrodes which deliver similar or dissimilar stimulation waveforms simultaneously and/or sequentially. Each of the stimulation waveforms can comprise one or more pulses comprising an entire phase or at least a portion of a phase at a superthreshold level. Alternatively or additionally, each of the stimulation waveforms can comprise one or more pulses comprising an entire phase or at least a portion of a phase at a subthreshold level.

In some embodiments, apparatus 10 is configured to vary one or more stimulation parameters. The stimulation parameters can be varied to optimize (e.g. balance the benefits of) therapeutic benefit, system efficiency, stimulation efficiency, avoidance and/or reduction of paresthesia, and/or reduction of charge.

Apparatus 10 can comprise one or more memory storage components (e.g. of an implantable device 200, external device 500, and/or other component of apparatus 10) that can store instructions for performing one or more algorithms, algorithm 15 shown. Algorithm 15 can comprise one or more algorithms that are configured to analyze data (e.g. data produced by a sensor-based functional element of apparatus 10) and produce a result. Algorithm 15 can comprise an algorithm (e.g. one or more algorithms) that are configured to steer current delivered by one or more stimulation elements 260, such as is described in applicant's co-pending U.S. patent application Ser. No. 17/383,972, titled "Systems with Implanted Conduit Tracking", filed Jul. 23, 2021. Algorithm 15 can comprise one or more algorithms configured to analyze data input by a user of apparatus 10 (e.g. a patient and/or a clinician of the patient), such as data entered via a user interface 680, and determine a stimulation paradigm SP, where paradigm SP comprises a set of stimulation parameter settings (e.g. stimulation energy settings as described herein) used to provide a therapy and/or otherwise treat a patient.

Each implantable device 200 of the present inventive concepts can be configured to deliver stimulation energy to one, two, three, four, or more anatomical locations of a patient, such as via sets of one or more stimulation elements 260 (e.g. electrodes) positioned on one or more leads 265. The stimulation energy delivered by the elements 260 can comprise tonic stimulation (e.g. a stimulation paradigm comprising a repeating pattern of pulses that are defined by pulse width, rate, and amplitude, where at the specified rate a pulse is delivered comprising a specified pulse width and a specified amplitude) and/or more complex stimulation waveforms (e.g. as represented by stimulation paradigm SP of apparatus 10). A first set of stimulation elements 260 can be positioned (e.g. implanted) and deliver and/or receive electrical current to deliver therapy (e.g. treat pain) in a first anatomical location, while a second set of stimulation elements 260 can be positioned and deliver and/or receive electrical current to deliver therapy (e.g. treat pain) in a second anatomical location. The first and second anatomical locations can include overlapping portions (e.g. the same tissue is included in each location) or they can be completely different volumes of tissue. The stimulation energy delivered to the two locations can be delivered sequentially, and/or simultaneously. In some embodiments, three, four or more anatomical locations receive therapy from corresponding sets of stimulation elements 260.

In some embodiments, one or more sets of stimulation elements 260 are configured to provide "combination waveform therapy", where the stimulation waveform defined by stimulation paradigm SP and delivered by elements 260 comprises a combination of two or more waveforms. For example, a first waveform can be delivered to a first anatomical location in which pain is present, and a second waveform can be delivered to a second anatomical location. The first waveform can comprise stimulation energy delivered at a frequency up to 100 Hz (e.g. to treat pain). The second waveform can comprise stimulation energy delivered at a higher frequency than the first waveform, such as a frequency of 1 KHz or more (e.g. for sub-threshold stimulation).

In some embodiments, one or more sets of stimulation elements 260 are configured to provide "microburst waveform therapy", where the stimulation waveform defined by stimulation paradigm SP and delivered by elements 260 comprises delivery of stimulation energy that is repeatedly turned on and off, such as to provide a therapy based on the repeated enhancement of onset of stimulation energy delivery (e.g. versus continuous stimulation energy delivery).

In some embodiments, one or more stimulation elements 260 are configured to provide "paired stimulation therapy", wherein the stimulation waveform defined by stimulation paradigm SP and delivered by elements 260 comprises at least two different types of waveforms that are delivered simultaneously, such as when the stimulation waveform comprises two or more of: a tonic stimulation waveform; a microburst stimulation waveform; and/or a waveform comprising a combination of pulses, trains, and/or bursts.

Each implantable device 200 can be configured to perform charge recovery in an "active" and/or a "passive" manner. For example, device 200 can perform active recovery by including a pulse of opposite polarity to the stimulating pulse(s) such that the net charge at the stimulation element 260 is zero (e.g. stimulating charge=recovery charge). Device 200 can perform passive charge recovery by electrically connecting the stimulation elements 260 for a period of time after delivery of stimulation energy to allow charge to dissipate (e.g. to allow the charge on included blocking capacitors to dissipate), thereby resulting in net zero charge at the stimulation elements 260. In some embodiments, implantable device 200 can perform charge recovery as described in applicant's U.S. patent application Ser. No. 17/384,020, titled "Stimulation Apparatus", filed Jul. 23, 2021. Configuration of active and/or passive charge recovery can be defined by stimulation paradigm SP.

In some embodiments, apparatus 10 (e.g. algorithm 15) is configured to apply a "pulse width constraint" when assessing the compatibility of a set of stimulation parameters, and/or when determining an acceptable range of values for a stimulation parameter to be used with a set of other stimulation parameters. For example, when a delivered stimulation includes delivery of stimulation at a relatively high rate (e.g. above 1 kHz, such as approximately 1.5 kHz), there may be parameter limitations applied due to the shorter pulse widths of stimulation pulses. Implantable device 200 can include a "minimum switching time" to account for in determining stimulation setting compatibility, such as a switching time of approximately 180 µsecs. In some embodiments, apparatus 10 is configured to deliver the pulses for each area before a subsequent stimulation cycle begins. For example, the minimum amount of time available to deliver all the pulses is determined by the highest programmed stimulation rate (i.e. the waveform including the shortest interval), while considering any associated other requirements, "overhead" herein, such as the switching time requirements (e.g. switching requirements of the current sources, such as a time requirement of approximately 180 µsecs). In other words, the minimum stimulation interval is determined (e.g. via algorithm 15) to be at least the time of the sum of all the pulse widths plus the overhead. In some embodiments, the stimulation delivered includes a high rate stimulation waveform of 1.5 kHz, and algorithm 15 limits passive recovery pulse width to a maximum of 110 µsecs, and active recovery pulse width to a maximum of 55p secs.

In some embodiments, apparatus 10 (e.g. algorithm 15) is configured to apply an envelope for stimulation based on: dosage on and dosage off times ($D_{ON}$ and $D_{OFF}$ times, respectively, each as described herein). Apparatus 10 can provide up to two dosing periods, which can be associated with the rate of stimulation. In some embodiments, apparatus 10 constrains $D_{ON}$ and/or $D_{OFF}$. $D_{ON}$ can be limited to a maximum time period, such as a maximum of 1 second. $D_{OFF}$ can be limited to a maximum time period, such as a maximum of 2 seconds, such as when the dosage period ($D_{ON}$ plus $D_{OFF}$) is limited to a time period of 2 seconds. Apparatus 10 can be configured to deliver stimulation energy at multiple rates, where a first rate (e.g. a relatively high rate) is delivered at a prescribed rate (e.g. a rate entered via user interface 680), while a second rate (e.g. a relatively low rate or otherwise lower than the first rate) is generated using a "N of M scheme" where a subset N of M pulses of the higher rate are delivered to effectively achieve the lower rate, such as is described herein in applicant's co-pending International PCT Patent Application Serial Number PCT/US2021/047815, titled "Apparatus for Delivering Customized Stimulation Waveforms", filed Aug. 26, 2021.

Figure 2A:
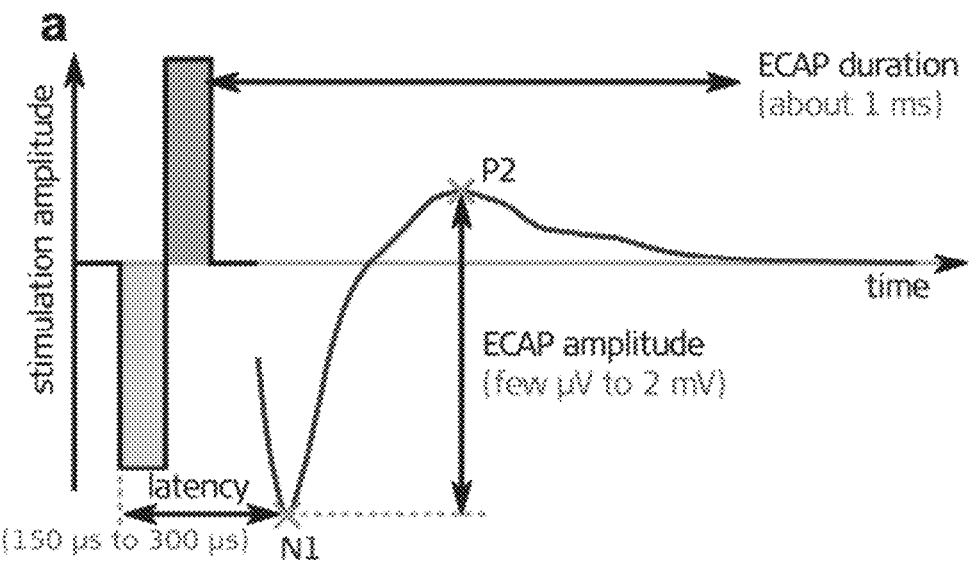
FIG. 2A illustrates a stimulation waveform and a neural response comprising an electrically evoked compound action potential (eCAP), consistent with the present inventive concepts.

Referring now to FIG. 2A, a stimulation waveform and an electrically evoked compound action potential (eCAP) are illustrated, consistent with the present inventive concepts. An electrically evoked compound action potential (eCAP) represents the synchronous firing of a population of electrically stimulated nerve fibers (e.g. as described in Gartner et al., "Fine-grain recordings of the electrically evoked compound action potential amplitude growth function in cochlear implant recipients," BioMedical Engineering OnLine, vol. 17, no. 140 (2018)). The stimulation waveform shown in FIG. 2A comprises a biphasic waveform (e.g. as provided by apparatus 10, where the stimulation energy is delivered by one or more stimulation elements 260 of an implantable device 200). In some embodiments, a monophasic waveform can be provided (e.g. as provided by apparatus 10, which can include passive charge recovery and/or accompanied by a delayed charge recovery).

Figure 3:
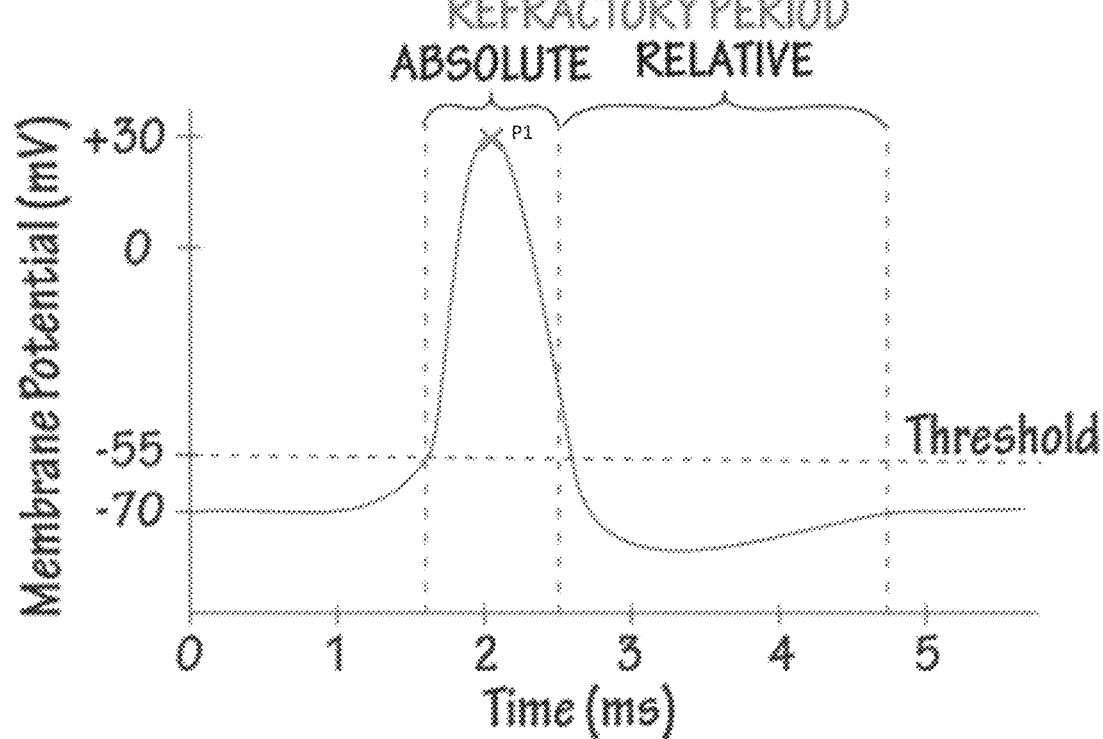
FIG. 3 illustrates a naturally occurring action potential, consistent with the present inventive concepts.

The resultant eCAP is a biphasic signal characterized by a negative peak, N1, and a positive peak P2. The magnitude of the absolute difference between N1 and P2 is referred to as the eCAP amplitude. The P1 peak of the eCAP (e.g. as shown in FIG. 3) occurs during the stimulation pulse, and it can be obscured by a stimulus artifact.

Due to the large stimulus artifact, the eCAP is usually measured by a recording element (e.g. an electrode) that is a different component than the component delivering the stimulation pulse (e.g. a stimulation element 260). The latency of the N1 peak relative to the stimulus is an indication of the distance between the recording component and one or both of: the stimulation pulse-delivering elements (e.g. elements 260) and one or more neural structures in the vicinity of the stimulation pulse-delivering delivering elements.

The eCAP of FIG. 2A can be measured in response to a provided stimulation waveform (e.g. as provided by apparatus 10 based on a stimulation paradigm SP).

Figure 2B:
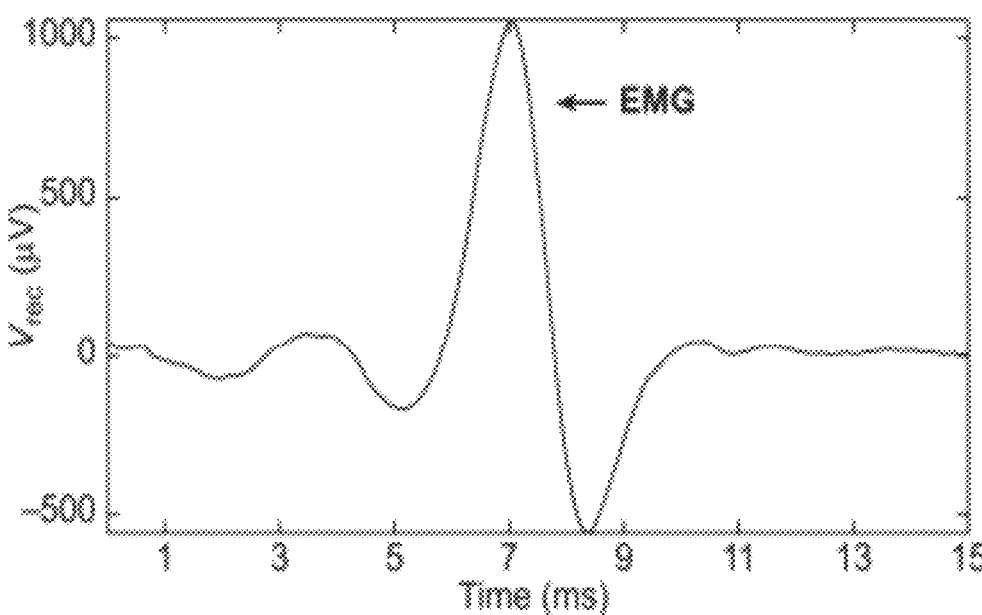
FIG. 2B illustrates a neural response comprising an electrically evoked muscle response.

Referring to FIG. 2B, a graph of an EMG response of the present inventive concepts is illustrated.

Referring to FIG. 3, a naturally occurring action potential is shown. It can be seen that after a neuron fires, it has a refractory period during which it cannot fire another action potential. This refractory period can comprise a time period between 1 msec and 5 msec.

The effect of the refractory period for electrical stimulation of nerves is that stimulus pulses that are delivered in relatively rapid succession (e.g. less than 1 msec, 3 msec, and/or 5 msec apart) may not impact the same population of neurons as stimulation pulses that are delivered less rapidly (e.g. at least 3 msec, at least 5 msec, and/or at least 7 msec apart). In other words, after a stimulation pulse is delivered by apparatus 10, the resultant population of neurons that fire may not be able to fire again for a period of time equal to their refractory period (e.g. a period of between 1 msec and 5 msec), and a subsequent stimulation pulse delivered by apparatus 10 during this refractory period will not be able to access (e.g. effectively stimulate) these neurons that are in a refractory state.

When apparatus 10 is delivering stimulation energy at relatively low rates (e.g. a rate of at most 100 Hz), issues with non-stimulation of neurons due to their being in a refractory period can potentially be avoided. When apparatus 10 is programmed to deliver higher rates (e.g. greater than 100 Hz), the efficiency of delivered stimulation pulses can be reduced (e.g. where efficiency can be defined as the number of neurons that fire for a given amount of charge delivered). However, it is known that high rates (e.g. rates greater than 100 Hz, 500 Hz, 1000 Hz, and/or 10,000 Hz) produce beneficial effects for the patient (e.g. pain relief), and high rate stimulation is especially used in sub-threshold and/or paresthesia-free and/or paresthesia-independent waveforms.

Figure 4:
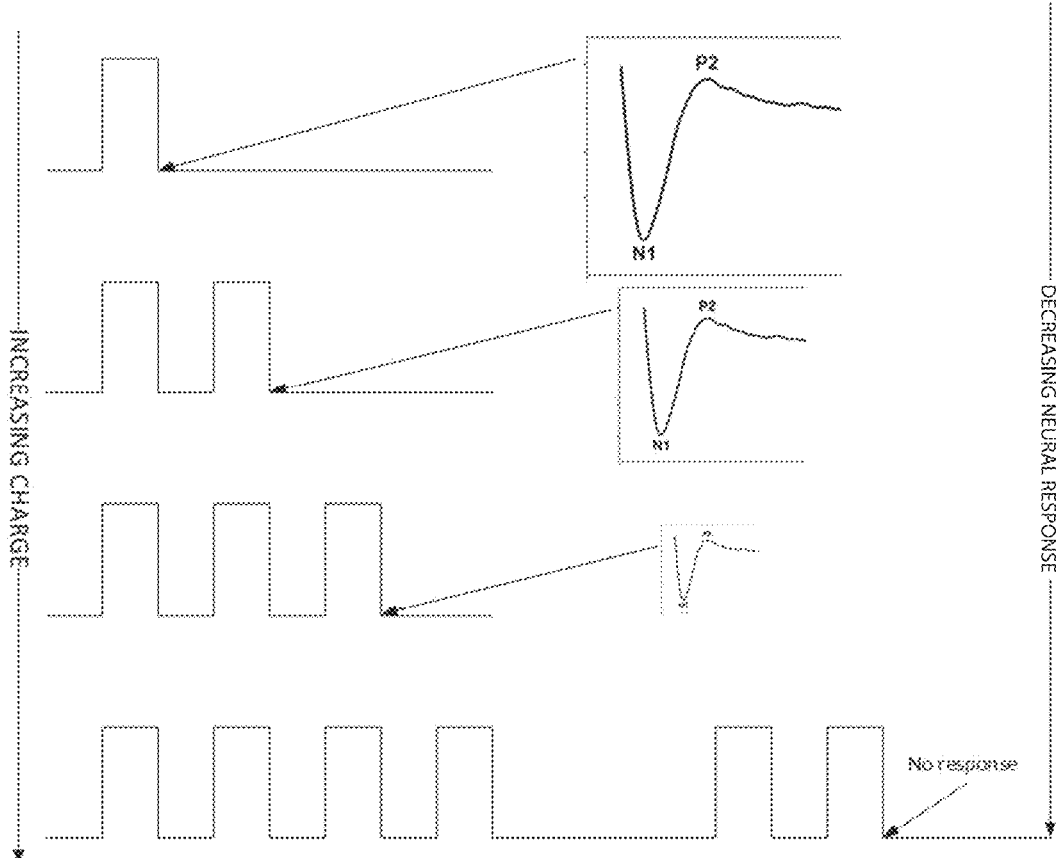
FIG. 4 illustrates the magnitude of a neural response measured at the end of a pulse train decreasing as more pulses are delivered, consistent with the present inventive concepts.

In some embodiments, apparatus 10 is configured to optimize delivery of stimulation pulse trains (e.g. high rate pulse trains, such as trains at a rate of at least 100 Hz) through the use of recorded neural response measurements (e.g. eCAP and/or EMG responses recorded via one or more sensor-based stimulation elements 260 and/or other one or more sensors of implantable device 200). During a programming session (e.g. during a trialing session) and/or during the implantation procedure of implantable device 200 (e.g. during a trialing session), neural response measurements can be made after the delivery of a train of pulses by one or more stimulation element 260. The magnitude of the neural response measured at the end of a pulse train will decrease as more pulses are delivered, the neural response magnitude decreasing until finally there is no measurable neural response, as shown in FIG. 4.

Apparatus 10, via algorithm 15, can create a stimulation paradigm SP that optimizes one or more stimulation waveforms using the neural response measurements described herein. For example, rather that deliver a continuous pulse train, a "refractory waiting period" (RWP) can be included in the stimulation waveform that would allow the subsequent pulse train to maintain its efficiency (by allowing the maximization of recruitment of neurons to the delivered stimulation energy). In some embodiments, the refractory waiting period RWP implemented by apparatus 10 is a determined time period that is long enough (e.g. at least 1 msec, 5 msec, and/or 10 msec) to avoid delivering energy to neurons that are still in their refractory period (e.g. the applicable neurons have fully repolarized). Alternatively or additionally, apparatus 10 can be configured to perform neural response measurements (e.g. eCAP and/or EMG measurements recorded from one or more stimulation elements 260 or other sensor of implantable device 200), and determine the duration of the refractory waiting period RWP to be applied based on a measurement of the neural response. For example, subsequent pulse trains can be delivered at a time when the magnitude of the neural response has decreased to a threshold level, such as a threshold in which the magnitude of the neural response has decreased at least 50%, at least 90%, or at least 99% (e.g. a percentage decrease compared to a maximum amplitude of the neural response).

Figure 5:
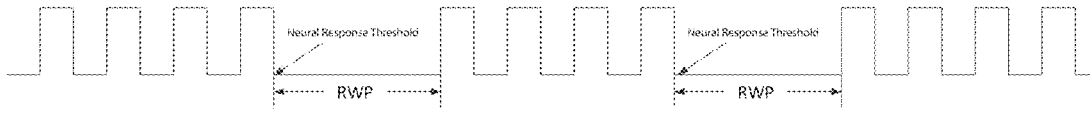
FIG. 5 illustrates a refractory waiting period that is included before a pulse train is delivered to allow each subsequent pulse train to maintain its efficiency, consistent with the present inventive concepts.

Apparatus 10 can produce a stimulation paradigm SP that includes an optimized stimulation waveform that is based on the measurement of neural response amplitudes (e.g. algorithm 15 can optimize the stimulation parameters of the waveform based on at least one or more eCAP and/or EMG measurements). As shown in FIG. 5, rather than deliver a continuous pulse train, after delivery of a pulse train (e.g. after delivery of each pulse train), a time duration equal to the refractory waiting period RWP can be included before the next pulse train is delivered, allowing each subsequent pulse train to maintain its efficiency (i.e. allowing the maximization of recruitment of neurons to the stimulus by avoiding delivery of stimulation energy to neurons that are still in their refractory period).

Figure 6:
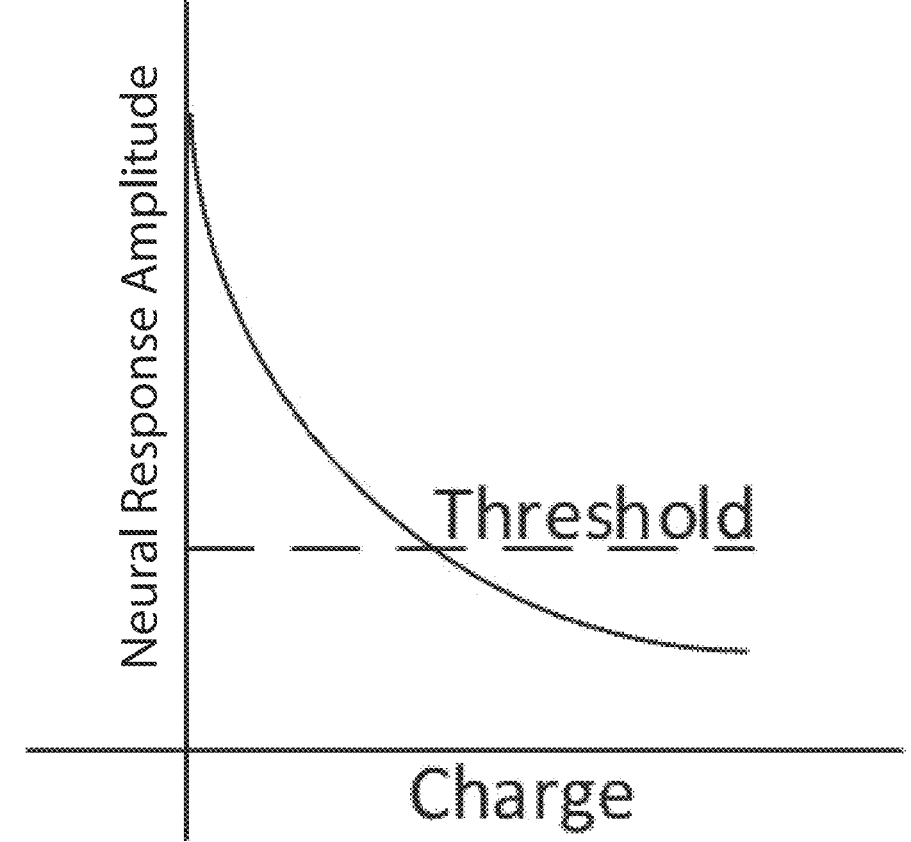
FIG. 6 illustrates the decreasing amplitude of a neural response to a level below a threshold, consistent with the present inventive concepts.

Referring now to FIG. 6, the amplitude of a neural response (e.g. an eCAP or EMG) decreasing below a threshold is illustrated. The number of pulses to be delivered by apparatus 10 before the refractory waiting period RWP is introduced can be based on criteria related to a threshold, such as the "neural response threshold criteria" illustrated in FIG. 6. In some embodiments, this threshold for the neural response amplitude is set to zero, or no response (e.g. the noise floor of the recording system of implantable device 200). In other embodiments, the threshold is set to a maximum perceptual charge summation, in other words the point at which adding more pulses does not cause stronger sensation and/or paresthesia for the patient. In yet other embodiments, the threshold can be an efficiency-derived metric, such as when the neural response is small enough that it is deemed to not justify the energy required to stimulate (e.g. a factor of the maximum neural response for instance 1%, 10%, 20%, 50% of the maximum eCAP or EMG response). In some embodiments, apparatus 10 is configured to make a limited number of neural response measurements (e.g. to minimize measurement time), where the response measurements (e.g. less than 10, or less than 5) are fitted to a trendline representing the neural response (N1-P2) magnitude.

Figure 7:
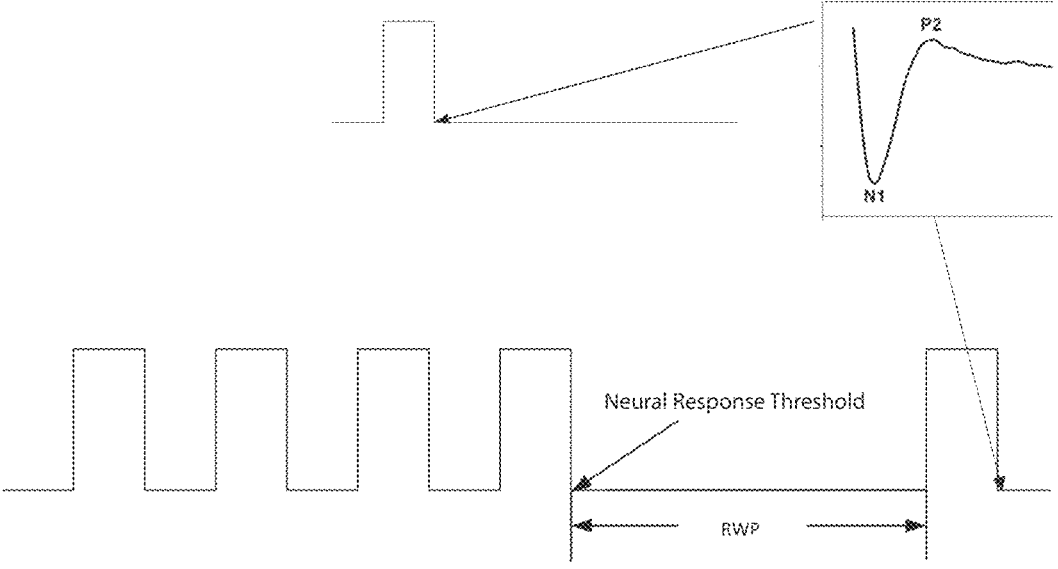
FIG. 7 illustrates a neural response to a single pulse that is used to determine an optimized refractory waiting period, consistent with the present inventive concepts.

As described herein, apparatus 10 can provide a stimulation waveform that includes a refractory waiting period RWP that is sufficiently long (e.g. at least 0.5 msec, 1 msec, 5 msec, or 10 msec) to guarantee that the neurons (e.g. the previously stimulated neurons) have fully repolarized. Apparatus 10 can be configured to determine the duration of a refractory waiting period RWP (e.g. each refractory waiting period RWP) based on neural response measurements (e.g. one or more eCAP and/or EMG measurements). In some embodiments, apparatus 10 performs a neural response measurement by increasing the refractory waiting period RWP up to the point that the neural response generated by the first pulse of a subsequent sequence matches that of that pulse when it is delivered by itself, or it is restored to a "neural response recovery threshold". A neural response recovery threshold can be a level heuristically assigned by apparatus 10 (e.g. a level of 67% of a maximum neural response level or within 20% to 100% of a maximum neural response level). As shown in FIG. 7, the neural response to a single pulse can be measured, such as in a repeating, iterative fashion, to determine an optimized refractory waiting period RWP. After the pulse train is applied (up to the point where the neural response threshold criteria are met), the refractory waiting period RWP can be applied, after which a single pulse can be delivered and the neural response measured. If the measured neural response is greater than a neural response recovery threshold as described hereabove, or relatively equal in magnitude to the single pulse, then apparatus 10 can be configured to categorize the repolarization as being complete, and the current refractory waiting period RWP as being acceptable for use. If the measured neural response magnitude is less than that measured for the single pulse by itself, then the refractory waiting period RWP can be increased (e.g. automatically by apparatus 10), and the process repeated until an optimized refractory waiting period RWP is determined.

The basic stimulation parameters that define stimulation can include: amplitude; pulse width; and or rate (i.e. frequency). Pulse width and rate in turn define the inter-pulse interval (IPI), where:

$$IPI = (1/Rate) - Pulse\ Width.$$

Figure 8:
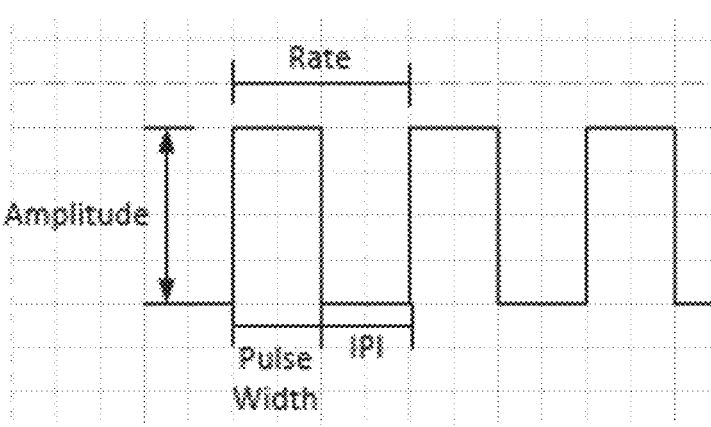
FIG. 8 illustrates a relatively high rate waveform, where an inter pulse interval is large enough that pulses do not interact in a neural fashion, consistent with the present inventive concepts.

Referring now to FIG. 8, even at relatively high rates, if the applied pulse width is low (a pulse width of 100 µsec at a rate of 500 Hz), then the IPI is large enough that the pulses do not interact in a neural fashion. In other words, each stimulation pulse delivered by apparatus 10 appears to the neural population as a distinct pulse, similar to what occurs at low frequencies. In some embodiments, apparatus 10 is configured to apply this technique per the stimulation parameter arrangement shown in FIG. 9, where the "low" frequency column can represent frequencies less than or equal to 100 Hz, the "mid" frequency column can represent frequencies between 100 Hz and 1000 Hz, and the "high" frequency column can represent frequencies of at least 1000 Hz. The pulse width "dividing line" for the mid frequency range can be between 10 µsec and 9 msec (e.g. when operating closer to 100 Hz).

Implantable device 200 can comprise a controller 250 that comprises a measurement portion that includes various electronic circuitry and other measurement components that are configured to measure a neural response (e.g. an eCAP and/or EMG as recorded by one or more stimulation elements 260 or other sensor of apparatus 10). This measurement portion of controller 250 can require a minimum amount of space within device 200 (e.g. within housing 210), and it can require a minimum amount of power for operation. The measurement portion can require a minimum sensitivity and/or a minimum gain for proper operation. In some embodiments, the measurement portion of controller 250 is of similar construction and arrangement as that described in applicant's co-pending U.S. patent application Ser. No. 17/379,928, titled "Stimulation Apparatus", filed Jul. 19, 2021 and U.S. patent application Ser. No. 17/384,020, titled "Stimulation Apparatus", filed Jul. 23, 2021. In some embodiments, the neural response measurement componentry can be included in a separate component of apparatus 10, such as trialing interface 80 and/or trialing interface 90 described herein (e.g. in addition to or as an alternative to this neural response measurement circuitry being integral to implantable device 200). In these embodiments, neural response measurements can be performed, and a refractory waiting period RWP can be determined, as described herein, during a trialing period and using a trialing device 80 and/or 90. Since the overall size of a trialing interface 80 and/or 90 is not as limited as an implantable device 200, the size and power requirements of the neural response measurement circuitry are much easier accomplished when included in an interface 80 and/or 90 versus within housing 210 of implantable device 200. In some embodiments, implantable device 200 is void of neural response measurement circuitry (e.g. to minimize size of implantable device 200, such as when trialing device 80 and/or 90 include neural response measurement circuitry used by apparatus 10 as described herein).

Undesired migration of one or more leads 265 can occur after implantation of the lead 265. If a neural response measurement was performed prior to the lead 265 migration occurring (e.g. an eCAP and/or EMG measurement performed by a trialing interface 80 and/or 90 during a trialing procedure or otherwise before the lead 265 migration occurs), the stimulation waveform delivered by apparatus 10 may need to be modified (e.g. a modification to the refractory waiting period RWP may need to be performed). In some embodiments, neural response measurements are performed at multiple lead 265 locations during an implantable device 200 implantation procedure. In some embodiments, patient posture is altered and/or various patient movements are performed during a neural response measurement (e.g. as these positions and/or movements can influence the distance between one or more stimulation elements 260 and the target neural structures to be stimulated).

Apparatus 10 can be configured to provide a broad range of available stimulation waveforms based on varying a combination of stimulation pulse parameters, such as amplitude, pulse width, and/or rate. It may not be practical to measure the number of pulses that could satisfy the neural response threshold criteria for every combination of these parameters, especially during the implantable device implantation procedure (e.g. intraoperatively). Another way for apparatus 10 to utilize a neural response measurement for determining a stimulation waveform to be delivered is in how the delivered energy handles charge, where:

$$\text{Charge Delivered} = (\text{Amplitude}) \times (\text{Pulse Width}) \times (\text{Number of Pulses})$$

Figure 9:
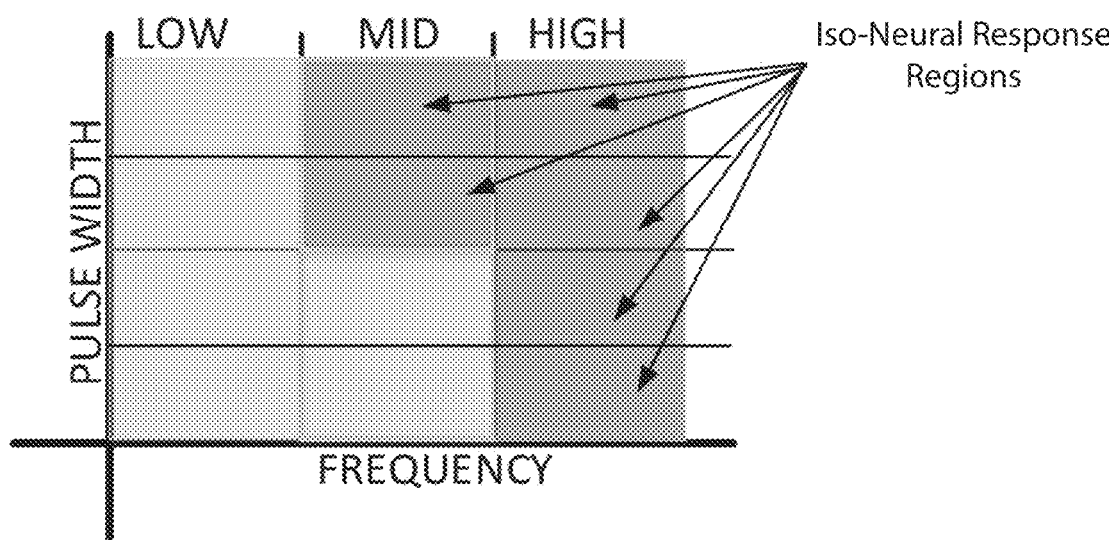
FIG. 9 illustrates a stimulation parameter arrangement, consistent with the present inventive concepts.

The neural response recorded for the Nth pulse in a train depends on the total charge delivered by pulses 1 through N. It may be sufficient to make a smaller set of measurements at charge values within the "patient's dynamic range", comprising either the "neural response dynamic range" or the "perceptual dynamic range", to cover all combinations of amplitude, pulse width and rate that may be provided by apparatus 10 (e.g. all combinations that may be used clinically). The neural response magnitude will generally be "s-shaped" (e.g. sigmoidal). The linear portion of the curve is the "neural response dynamic range", after which the neural response saturates. The "perceptual dynamic range" is the range from a paresthesia threshold to a maximum comfort (or discomfort) amplitude. Rather than using a single set of charge values, apparatus 10 can be configured to break down the usable region into smaller "Iso-neural response" regions (e.g. as shown in FIG. 9). During clinical use, as programs are applied therapeutically, apparatus 10 can determine in which region of FIG. 9 to operate, and it can provide a stimulation waveform using an appropriate charge-neural response table (e.g. a table that provides the number of pulses that can be delivered before a neural response threshold condition is met for a given amplitude, pulse width, and/or rate).

The configurations of apparatus 10 described hereabove in reference to FIGS. 2 through 9 can be used with: monophasic pulses with passive charge recovery; and/or monophasic pulses with charge recovery occurring after a group of pulses (for instance after every 2nd pulse, after all the pulses in the group are delivered, and the like). Alternatively or additionally, apparatus 10 can apply these configurations to biphasic, triphasic, and/or other multi-phasic waveshapes.

In some embodiments, measurement of an eCAP, EMG, and/or other neural response by apparatus 10 can be performed during a time period in which the patient is receiving therapy (e.g. stimulation energy is being delivered continuously and/or intermittently such as to provide pain relief). In these embodiments, the number of pulses and/or other stimulation paradigm SP parameter can be adjusted dynamically during time periods in which the patient is otherwise receiving therapy from apparatus 10 (e.g. as opposed to times of initial programming of apparatus 10). In some embodiments, apparatus 10 is configured to deliver stimulation energy at an initial set of energy delivery settings (e.g. an initial stimulation paradigm SP). During this initial stage, time between stimulation pulses can be varied, and apparatus 10 can perform one or more neural response measurements. Apparatus 10 (e.g. via algorithm 15) can automatically determine an optimized time between pulses from these neural response measurements, and adjust energy delivery accordingly (e.g. adjust stimulation paradigm SP based on these neural response measurements). In some embodiments, this varying of time between pulses and corresponding neural response measurements is performed at a particular time or times, such as when initiated: at the start of each stimulation program; at the start of each day; on a periodic basis; on a temporally determined basis; and/or when a patient change occurs such as when a patient posture change occurs (e.g. as detected by a sensor of apparatus 10).

The configurations described hereabove include measuring the neural response to determine when it decreases below a certain threshold to maximize the efficacy of stimulation. Alternatively, apparatus 10 can be configured to maintain the neural response at a relatively constant magnitude (e.g. within a percentage of 10% to 100% after each pulse). In other words, the neural response measured by apparatus 10 after a single stimulation pulse delivered by apparatus 10 is maintained after a second pulse (e.g. as measured by apparatus 10, such as when provided at a frequency of at least 100 Hz).

In some embodiments, apparatus 10 is configured to provide increased neural response magnitudes by increasing the amplitude of the stimulation pulses delivered. For example, a first pulse (P1) may be presented at a first amplitude (A1), a second pulse (P2) at a second amplitude (A2), a third pulse (P3) at a third amplitude (A3), and so on, where each subsequent amplitude is greater than the previous (e.g. A2 is greater than A1, A3 is greater than A2, and so on). In these embodiments, amplitude can be increased until an apparatus 10 threshold is reached (e.g. a threshold based on compliance voltage, available energy, and/or other apparatus 10 parameter). At such time, the stimulation pulse trains being delivered by apparatus 10 can be stopped, and a refractory waiting period RWP can be performed (e.g. included, as described herein), such that the neural response (e.g. eCAP or EMG) is restored.

In some embodiments, apparatus 10 is configured to similarly increase pulse width in successive stimulation pulses (e.g. instead of increasing the amplitude as described hereabove). In these embodiments, pulse width can be increased until an apparatus 10 threshold is reached (e.g. as describe hereabove), and a refractory waiting period RWP can be performed. In some embodiments, apparatus 10 is configured to increase both amplitude and pulse width over a set of successive pulses until an apparatus 10 threshold is reached, and a refractory waiting period RWP can be performed.

Alternatively or additionally, apparatus 10 can be configured to increase the gap between pulses, such as to allow a larger recovery of the neural response magnitude. This configuration results in a stimulation waveform that does not have a constant frequency (e.g. not a single frequency). In these embodiments, the gap between pulses can be increased until an apparatus 10 threshold is reached (e.g. as described hereabove), and a refractory waiting period RWP can be performed.

Figures 10A, 10B, 10C, 10D:
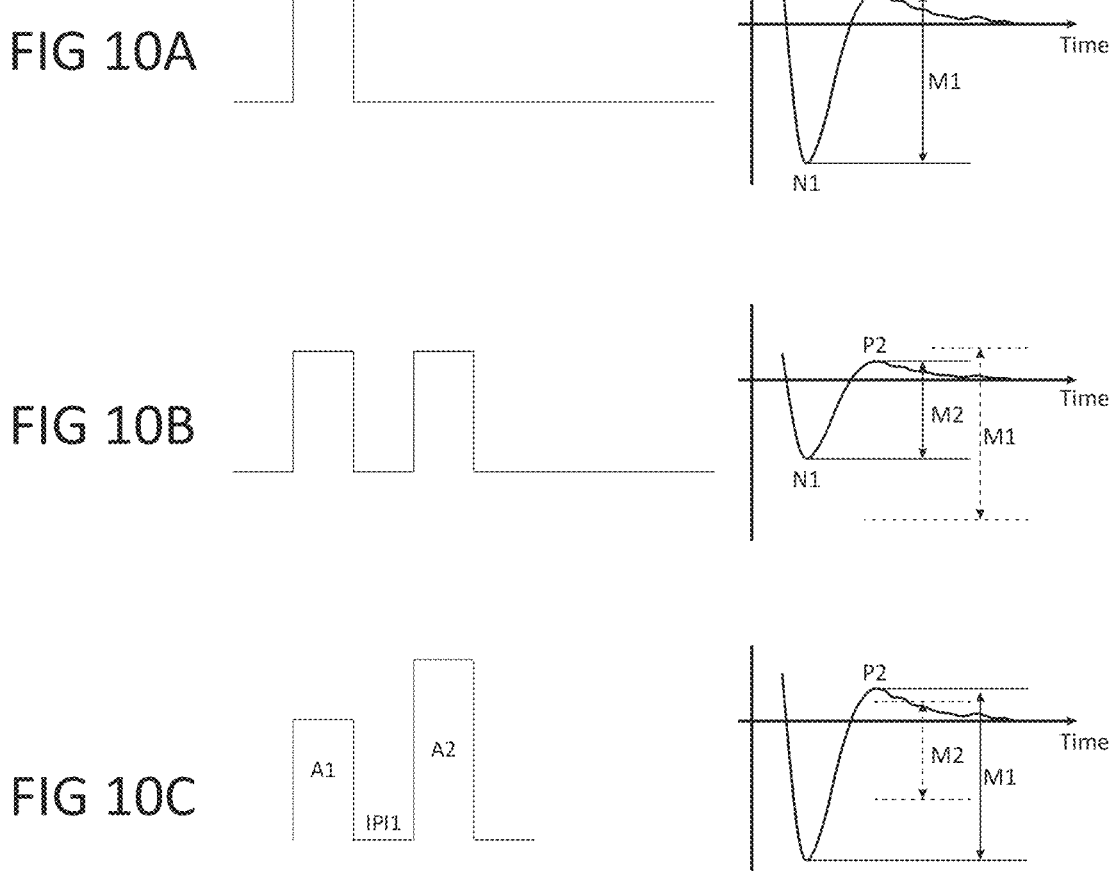
FIGS. 10A-D illustrate various stimulation waveforms and resulting neural responses, consistent with the present inventive concepts.

Referring additionally to FIGS. 10A-D, stimulation waveforms and resultant neural responses (e.g. eCAPs and/or EMGs) are shown, consistent with the present inventive concepts. FIG. 10A illustrates a first stimulation waveform including a single pulse, as well as the resultant neural response, and FIG. 10B illustrates a second stimulation waveform including two pulses, and the neural response that results after the second pulse. A comparison of the neural responses shown in FIGS. 10A and 10B indicates a reduction in neural response magnitude results after the delivery of the second pulse of FIG. 10B as compared to the neural response that results after the delivery of the single pulse of FIG. 10A (i.e. the neural response magnitude M2 of FIG. 10B is less than neural response magnitude M1 of FIG. 10A). FIGS. 10C and 10D show how the amplitude or inter-pulse-interval (IPI) can be changed to keep the neural response (e.g. eCAP or EMG) roughly constant. In FIG. 10C, amplitude is increased (A2 is greater than A1) to result in a neural response with magnitude M1 as shown (magnitude M2 of FIG. 10B shown for reference), and in FIG. 10D, IPI is increased to result in a neural response with magnitude M1 as shown (magnitude M2 of FIG. 10B shown for reference).

Figure 11:
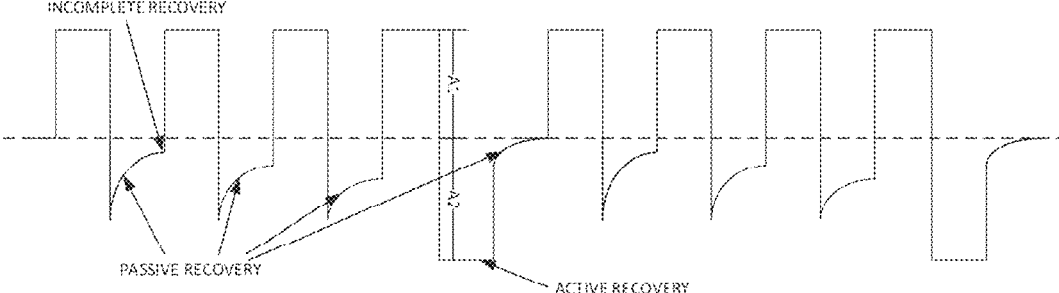
FIG. 11 illustrates a stimulation waveform including passive and active charge recovery, consistent with the present inventive concepts.

Referring now to FIG. 11, a stimulation waveform including passive and active charge recovery is illustrated, consistent with the present inventive concepts. As described herein, apparatus 10 can be configured to perform charge recovery in an active arrangement or a passive arrangement. Passive recovery can be implemented in order to reduce required energy (e.g. due to its energy efficiency). Active recovery can be implemented if the time available (e.g. time between pulses) is not sufficient to perform passive charge recovery.

In some embodiments, during delivery of stimulation energy by one or more stimulation elements 260, algorithm 15 is configured to cause implantable device 200 to automatically switch between passive charge recovery and active charge recovery. For example, after delivery of energy via one or more stimulation pulses, if there is insufficient time to perform charge recovery (e.g. before another stimulation pulse is to be delivered), algorithm 15 can be configured to cause implantable device 200 to perform active charge recovery.

In some embodiments, algorithm 15 is configured to cause implantable device 200 to perform a "partial charge recovery", for example a charge recovery in which some but not all of accumulated charge is recovered. If charge is not fully recovered, a voltage can remain on a stimulation element 260, such as a voltage that has built up across an included DC blocking capacitor that is in series with the stimulation element 260. This voltage can initially cause the compliance voltage of implantable device 200 to increase, but eventually can block the flow of current entirely. Leaving charge on the DC blocking capacitor also means that there is a DC bias on the capacitor, which can negatively impact long term reliability (e.g. due to an undesired decrease in capacitance of the blocking capacitors which adversely affects system efficiency and eventually can result in a failure condition). In these circumstances, algorithm 15 can employ a mixture of active and passive charge recovery (e.g. to avoid the undesired condition). Algorithm 15 can be configured to cause a recovery pulse of active charge recovery to be larger than the associated stimulating pulse, such as is shown in FIG. 10 where amplitude A2 is greater than amplitude A1. Amplitude A2 can have a magnitude that is selected to remove any previously accumulated charge. Alternatively or additionally, algorithm 15 can be configured to cause passive recovery to occur at the end of an active recovery pulse (e.g. an active recovery pulse of any amplitude). The various combinations of active and passive charge recovery provided by apparatus 10 (e.g. as determined by algorithm 15) can be used to accommodate higher stimulation rates (e.g. as compared with the rates achievable using passive recovery alone), as well as improved stimulation efficiency (e.g. improved power efficiency as compared to using active recovery alone).

Figure 12:
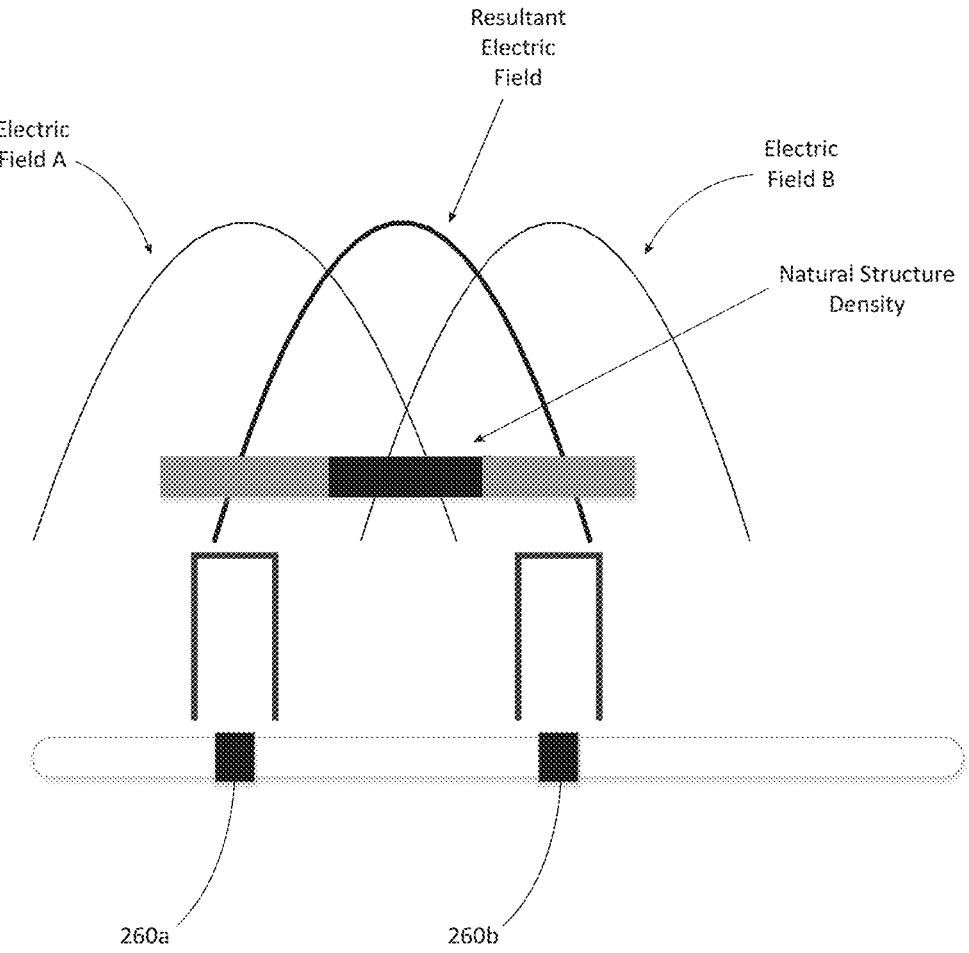
FIG. 12 illustrates an anatomic view of two electrodes delivering current to tissue, consistent with the present inventive concepts.

Referring now to FIG. 12, an anatomic schematic view of two electrodes delivering current to tissue is illustrated, consistent with the present inventive concepts. The distribution of neural structures within target tissue may be non-uniform, such as due to physiologic and/or anatomic variations normally found in mammalian patients, or to tissue variations that may result from, and/or otherwise be associated with, trauma or disease. Stimulation at an electrode-based stimulation element 260 is generally modeled as producing a gaussian electric field around the stimulating electrode. If the field generated by a single electrode stimulates only a fraction of the target neural structures to be stimulated, it may be advantageous for apparatus 10 to use current steering to shift the centroid of the electric field to optimally stimulate the targeted neural structures. In FIG. 12, the electric fields generated by two electrode-based stimulation elements 260 are shown, as well as the cumulative result of driving both elements 260 (their fields sum) to steer the field to the "middle region" of the space between the two elements 260. In this example, the middle region is where the neural structures are most dense, and this stimulation configuration presents an optimized solution. In practice, the optimal location can be anywhere along the space between the two elements 260 and the appropriate combined electric field can be generated by driving each element 260 with a fraction of the total current. In the example shown, the two elements 260 each deliver half the total stimulation current delivered to tissue.

Figure 13:
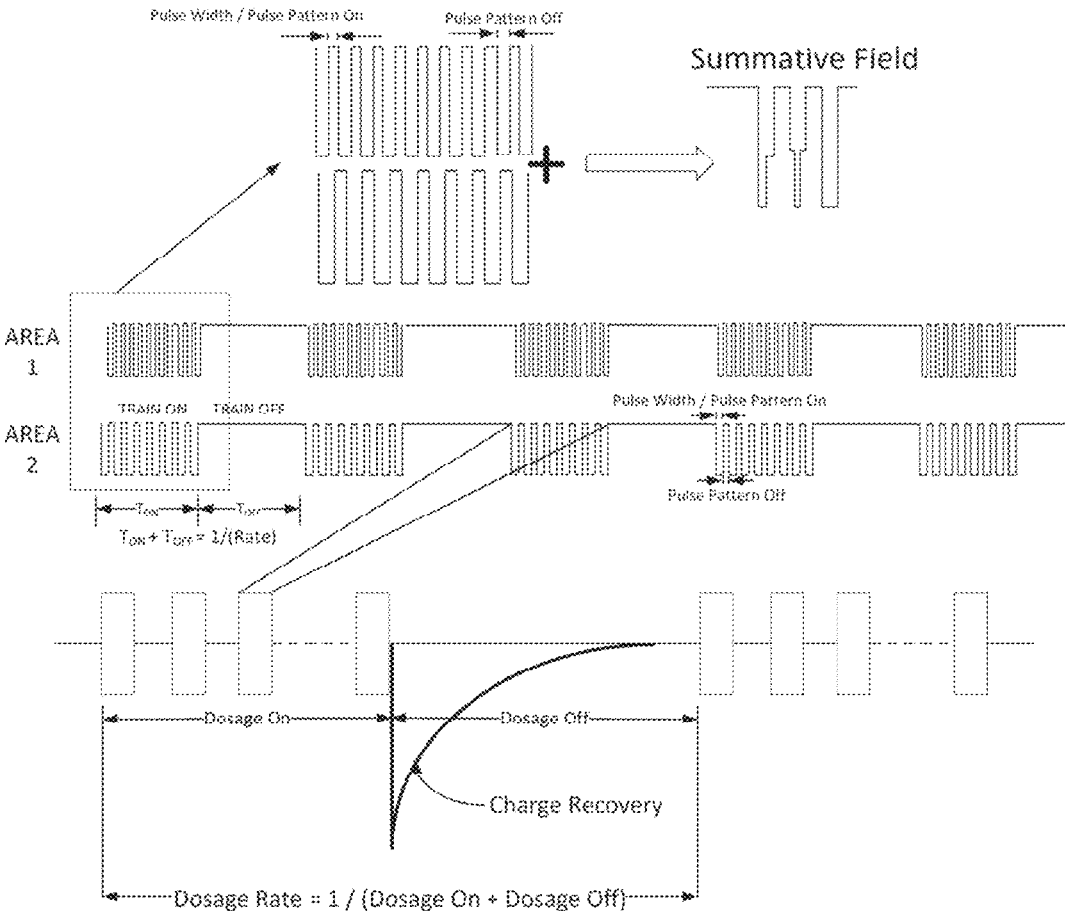
FIG. 13 illustrates stimulation waveforms for stimulating multiple target areas, consistent with the present inventive concepts.

Referring now to FIG. 13, stimulation waveforms for stimulating two target areas simultaneously is illustrated, consistent with the present inventive concepts. A stimulation paradigm SP of apparatus 10 can define various stimulation parameters that can be used to stimulate one, two, or more target areas. In some embodiments, at least two target areas can be stimulated simultaneously. A stimulation paradigm SP can define one or more stimulation parameter settings for each of multiple target areas. For each target area (e.g. multiple target areas to be stimulated simultaneously), applicable stimulation parameter settings include but are not limited to: selection of electrodes to deliver stimulation current (e.g. a subset of stimulation elements 260 of one or more leads 265); anode and/or cathode configuration of each electrode; pulse width; IPI; a train parameter (e.g. a train on and/or train off parameter); and/or a dosage parameter (e.g. a dosage on and/or dosage off parameter). In the example shown in FIG. 13, the train and dosage times are common between the two areas to be stimulated, Target Area 1 and Target Area 2 shown. Alternatively, the train and/or dosage times can be distinct. The pulse width and IPI can be different (e.g. as shown). If the electrodes are selected such that the electric fields generated by both areas overlap, then the target tissue (e.g. neurons) that are in the overlapping portion of the fields experience a resultant field that is the summation of the two drive signals. The drive signals can interact constructively and/or destructively. An example of such a summative field is shown in FIG. 13, where the result of the interaction of the first 3 pulses is shown. Depending on how the IPI and pulse width parameters are selected, the resulting summative signal experienced by the target tissue (e.g. neurons) can be very complex and can approach being stochastic. Stochastic signals may produce firing patterns that are more natural (e.g. not artificial). The stochastic pattern can also allow for the signal to be applied at a sub-paresthesia level. In some embodiments, two distinct signals are delivered, and the summation occurs in the neural structures that are being stimulated. This delivery configuration of apparatus 10 can also produce randomness.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth hereinbelow not be construed as being order-specific unless such order specificity is expressly stated in the claim.

What is claimed is:

1. A method for treating a patient, comprising:
delivering a plurality of pulses to tissue of the patient via one or more stimulation elements of an implantable device;
measuring, via a sensor of the implantable device, a first neural response induced by a first pulse of the plurality of pulses and a second neural response induced by a second pulse of the plurality of pulses, wherein the first pulse is a discrete pulse and the second pulse is an initial pulse of a pulse train;
comparing a magnitude of the second neural response to a neural response threshold, wherein the neural response threshold is defined by a percentage of the magnitude of the first neural response; and
configuring one or more stimulation parameters of a stimulation waveform for the patient based on the comparison.

2. The method of claim 1 further comprising measuring a neural response after each pulse of the pulse train.

3. The method of claim 1, wherein the neural response threshold is less than or equal to 50% of the magnitude of the first neural response.

4. The method of claim 1, wherein the one or more stimulation parameters comprises a number of pulses of the stimulation waveform, and wherein the configuring comprises setting the number of pulses such that a third, subsequent neural response is below the neural response threshold.

5. The method of claim 4 further comprising adjusting a number of pulses of the pulse train to change a magnitude of the third neural response.

6. The method of claim 1, wherein the neural response threshold is equal to or within 20% of the magnitude of the first neural response.

7. The method of claim 1, wherein the one or more stimulation parameters comprise a refractory waiting period (RWP), wherein the RWP is a time period configured to allow neurons of the tissue of the patient to repolarize.

8. The method of claim 7, wherein configuring the one or more stimulation parameters comprises increasing the RWP.

9. The method of claim 7, wherein the RWP is at least 0.5 ms.

10. The method of claim 1, wherein an external device communicably coupled to the implantable device configures the one or more stimulation parameters.

11. The method of claim 1, wherein both of the first and second neural responses comprise one or both of an eCAP measurement and an EMG measurement.

12. A method for treating a patient, comprising:
delivering energy to tissue of the patient via one or more stimulation elements of an implantable device;
measuring, via sensor of the implantable device, a plurality of neural responses induced by the delivered energy;
determining a measured neural response of the plurality of measured neural responses meets a neural response condition, wherein the neural response condition defines a threshold for a magnitude of the measured neural response; and
configuring one or more stimulation parameters of a stimulation waveform for the patient based on the determination.

13. The method of claim 12, wherein the energy comprises one or more pulse trains and one or more discrete pulses, wherein each pulse train comprises a plurality of pulses.

14. The method of claim 12, wherein delivering the energy to the tissue comprises delivering a discrete pulse and a pulse train, wherein the plurality of neural responses comprises a discrete neural response induced by the discrete pulse, wherein a first pulse of the pulse train is configured to induce the measured neural response, and wherein the threshold for the magnitude of the measured neural response is equal to a magnitude of the discrete neural response.

15. The method of claim 12, wherein the one or more stimulation parameters comprise a refractory waiting period (RWP), wherein the RWP is a time period configured to allow neurons of the tissue of the patient to repolarize.

16. The method of claim 15, wherein configuring one or more stimulation parameters comprises increasing the time period of the RWP.

17. The method of claim 15, wherein the RWP is at least 0.5 ms.

18. The method of claim 12, wherein the energy comprises a pulse train, and wherein measuring the plurality of neural responses comprises measuring a first neural response after a first pulse of the pulse train and a second neural response after a last pulse of the pulse train.

19. The method of claim 18 further comprising comparing a magnitude of the second neural response to a neural response threshold and adjusting a number of pulses of the stimulation waveform based on the comparison.

20. The method of claim 12, wherein the implantable device comprises a trial implantable device, wherein the energy is delivered and the measured neural response is determined during a trialing session for the trial implantable device.

21. The method of claim 20 further comprising delivering the stimulation waveform to the patient via one or both of the trial implantable device and a long-term implantable device based on the measured neural response determined with the trial implantable device.

22. The method of claim 12, wherein the implantable device comprises a long-term implantable device, and wherein the energy is delivered and the measured neural response is determined during an implantation procedure of the long-term device.

23. A stimulation system for a patient, comprising:
an implantable device comprising:
one or more stimulation elements configured to deliver a plurality of pulses to tissue of the patient; and a sensor configured to interface with the tissue of the patient and measure a first neural response induced by a first pulse of the plurality of pulses and a second neural response induced by a second pulse of the plurality of pulses, wherein the first pulse is a discrete pulse and the second pulse is an initial pulse of a pulse train; and an external device communicably coupled to the implantable device and configured to;

compare a magnitude of the second neural response to a neural response threshold, wherein the neural response threshold is defined by a percentage of the magnitude of the first neural response; and configure one or more stimulation parameters of a stimulation waveform for the patient based on the comparison.

24. A stimulation system for a patient, comprising:

an implantable device comprising:

one or more stimulation elements configured to deliver stimulation energy to tissue of the patient; and a sensor configured to interface with the tissue of the patient and measure a plurality of neural responses induced by the delivered energy; and an external device communicably coupled to the implantable device and configured to:

determine a measured neural response of the plurality of measured neural responses meets a neural response condition, wherein the neural response condition defines a threshold for a magnitude of the measured neural response; and configure one or more stimulation parameters of a stimulation waveform for the patient based on the determination.

\*   \*   \*   \*   \*